(12) United States Patent
Wei

(10) Patent No.: US 10,006,089 B2
(45) Date of Patent: Jun. 26, 2018

(54) MCL-1 AS A THERAPEUTIC TARGET IN SCFFBW7 DEFICIENT NEOPLASM

(75) Inventor: Wenyi Wei, Brookline, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days. days.

(21) Appl. No.: 14/001,970

(22) PCT Filed: Mar. 2, 2012

(86) PCT No.: PCT/US2012/027516
§ 371 (c)(1),
(2), (4) Date: Dec. 10, 2013

(87) PCT Pub. No.: WO2012/119091
PCT Pub. Date: Sep. 7, 2012

(65) Prior Publication Data
US 2014/0113913 A1 Apr. 24, 2014
US 2015/0005317 A9 Jan. 1, 2015

Related U.S. Application Data

(60) Provisional application No. 61/448,648, filed on Mar. 2, 2011.

(51) Int. Cl.
| C12Q 1/68 | (2018.01) |
| C12Q 1/6886 | (2018.01) |
| A61K 31/44 | (2006.01) |
| A61K 31/495 | (2006.01) |
| G01N 33/574 | (2006.01) |
| C07H 21/02 | (2006.01) |

(52) U.S. Cl.
CPC ........... *C12Q 1/6886* (2013.01); *A61K 31/44* (2013.01); *A61K 31/495* (2013.01); *G01N 33/574* (2013.01); *C12Q 2600/106* (2013.01); *C12Q 2600/156* (2013.01); *C12Q 2600/158* (2013.01)

(58) Field of Classification Search
CPC ........... C12C 1/6886; C12C 2600/106; C12C 2600/156; C12C 2600/158; G01N 33/574
See application file for complete search history.

(56) References Cited

FOREIGN PATENT DOCUMENTS

WO WO 2007/077435 A1 7/2007
WO WO 2010/030865 A2 3/2010

OTHER PUBLICATIONS

Wilding, J.L. et al., Cancer Res., vol. 74, pp. 2377-2384 (2014).*
Azmi, A.S. et al., Expert Opinion in Emerging Drugs, vol. 16, pp. 59-70 (2011).*

Akhoondi et al., Inactivation of FBXW7/hCDC4-β expression by promoter hypermethylation is associated with favorable prognosis in primary breast cancer. Breast Cancer Res. 2010;12(6):R105. doi: 10.1186/bcr2788. Epub Dec. 1, 2010.
Cheok et al., Pharmacogenetics in acute lymphoblastic leukemia. Semin Hematol. Jan. 2009;46(1):39-51. doi:10.1053/j.seminhematol.2008.09.002.
Malyukova et al., The tumor suppressor gene hCDC4 is frequently mutated in human T-cell acute lymphoblastic leukemia with functional consequences for Notch signaling. Cancer Res. Jun. 15, 2007;67(12):5611-6. Erratum in: Cancer Res. Mar. 15, 2008;68(6):2051. Akhondi, Shahab [corrected to Akhoondi, Shahab].
Matsuoka et al., Fbxw7 acts as a critical fail-safe against premature loss of hematopoietic stem cells and development of T-ALL. Genes Dev. Apr. 15, 2008;22(8):986-91. doi: 10.1101/gad.1621808. Epub Mar. 26, 2008.
Rajagopalan et al., Inactivation of hCDC4 can cause chromosomal instability. Nature. Mar. 4, 2004;428(6978):77-81.
Wei et al., Gene expression-based chemical genomics identifies rapamycin as a modulator of MCL1 and glucocorticoid resistance. Cancer Cell. Oct. 2006;10(4):331-42. Epub Sep. 28, 2006.
Wertz et al., Sensitivity to antitubulin chemotherapeutics is regulated by MCL1 and FBW7. Nature. Mar. 3, 2011;471(7336):110-4. doi: 10.1038/nature09779. Erratum in: Nature. Jul. 7, 2011;475(7354):122.
Akgul et al., Mcl-1 is a potential therapeutic target in multiple types of cancer. Cell Mol Life Sci. Apr. 2009;66(8):1326-36. doi: 10.1007/s00018-008-8637-6.
Benmaamar et al., Involvement of the SCF complex in the control of Cdh1 degradation in S-phase. Cell Cycle. Sep. 2005;4(9):1230-2. Epub Sep. 20, 2005.
Chen et al., ARF-BP1/Mule is a critical mediator of the ARF tumor suppressor. Cell. Jul. 1, 2005;121(7):1071-83.
Cragg et al., Unleashing the power of inhibitors of oncogenic kinases through BH3 mimetics. Nat Rev Cancer. May 2009;9(5):321-6. doi: 10.1038/nrc2615. Epub Apr. 3, 2009.
Ding et al., Degradation of Mcl-1 by beta-TrCP mediates glycogen synthase kinase 3-induced tumor suppression and chemosensitization. Mol Cell Biol. Jun. 2007;27(11):4006-17. Epub Mar. 26, 2007.
Gao et al., Phosphorylation by Akt1 promotes cytoplasmic localization of Skp2 and impairs APCCdh1-mediated Skp2 destruction. Nat Cell Biol. Apr. 2009;11(4):397-408. doi: 10.1038/ncb1847. Epub Mar. 8, 2009.

(Continued)

*Primary Examiner* — Teresa E Strzelecka
(74) *Attorney, Agent, or Firm* — Wolf, Greenfield & Sacks, P.C.

(57) ABSTRACT

Some embodiments are based on the discovery that proliferative diseases (e.g., neoplastic diseases, for example, tumors or cancers) having an FBW7 mutation or other FBW7 deficiency are sensitive to Mcl1 inhibiting agents, but resistant to pro-apoptotic drugs that do not inhibit Mcl1. Some embodiments provide methods of treating a proliferative disease based on an assessment of FBW7 expression level or mutation status. Some embodiments provide methods of classifying a hyperproliferative cell or cell population, for example, a malignant cell or cell population based on an assessment of FBW7 expression level or mutation status. Some embodiments provide methods of selecting a treatment regimen for treating a proliferative disease, for example, a malignant disorder, based on an assessment of FBW7 expression level or mutation status.

2 Claims, 23 Drawing Sheets

(56) References Cited

OTHER PUBLICATIONS

Gupta-Rossi et al., Functional interaction between SEL-10, an F-box protein, and the nuclear form of activated Notch1 receptor. J Biol Chem. Sep. 14, 2001;276(37):34371-8. Epub Jun. 25, 2001.

Koepp et al., Phosphorylation-dependent ubiquitination of cyclin E by the SCFFbw7 ubiquitin ligase. Science. Oct. 5, 2001;294(5540):173-7. Epub Aug. 30, 2001.

Konopleva et al., Mechanisms of antileukemic activity of the novel Bcl-2 homology domain-3 mimetic GX15-070 (obatoclax). Cancer Res. May 1, 2008;68(9):3413-20. doi: 10.1158/0008-5472.CAN-07-1919.

Maser et al., Chromosomally unstable mouse tumours have genomic alterations similar to diverse human cancers. Nature. Jun. 21, 2007;447(7147):966-71. Epub May 21, 2007.

Maurer et al., Glycogen synthase kinase-3 regulates mitochondrial outer membrane permeabilization and apoptosis by destabilization of MCL-1. Mol Cell. Mar. 17, 2006;21(6):749-60.

Muller et al., Concurrent inhibition of PI3K and mTORC1/mTORC2 overcomes resistance to rapamycin induced apoptosis by down-regulation of Mcl-1 in mantle cell lymphoma. Int J Cancer. Oct. 15, 2013;133(8):1813-24. doi: 10.1002/ijc.28206. Epub Jun. 15, 2013.

Nijhawan et al., Elimination of Mcl-1 is required for the initiation of apoptosis following ultraviolet irradiation. Genes Dev. Jun. 15, 2003;17(12):1475-86. Epub Jun. 3, 2003.

Onoyama et al., Conditional inactivation of Fbxw7 impairs cell-cycle exit during T cell differentiation and results in lymphomatogenesis. J Exp Med. Nov. 26, 2007;204(12):2875-88. Epub Nov. 12, 2007.

Ofterman et al., Development and maintenance of B and T lymphocytes requires antiapoptotic MCL-1. Nature. Dec. 11, 2003;426(6967):671-6.

Panka et al., GSK-3beta inhibition enhances sorafenib-induced apoptosis in melanoma cell lines. J Biol Chem. Jan. 11, 2008;283(2):726-32. Epub Nov. 8, 2007.

Popov et al., The ubiquitin-specific protease USP28 is required for MYC stability. Nat Cell Biol. Jul. 2007;9(7):765-74. Epub Jun. 10, 2007.

Sánchez et al., A convoluted way to die. Neuron. Mar. 2001;29(3):563-6.

Schwickart et al., Deubiquitinase USP9X stabilizes MCL1 and promotes tumour cell survival. Nature. Jan. 7, 2010;463(7277):103-7. doi: 10.1038/nature08646. Epub Dec. 20, 2009.

Sharma et al., Oncogene addiction: setting the stage for molecularly targeted cancer therapy. Genes Dev. Dec. 15, 2007;21(24):3214-31.

Shaulian et al., AP-1 as a regulator of cell life and death. Nat Cell Biol. May 2002;4(5):E131-6.

Thompson et al., The SCFFBW7 ubiquitin ligase complex as a tumor suppressor in T cell leukemia. J Exp Med. Aug. 6, 2007;204(8):1825-35. Epub Jul. 23, 2007.

Van Delft et al., The BH3 mimetic ABT-737 targets selective Bcl-2 proteins and efficiently induces apoptosis via Bak/Bax if Mcl-1 is neutralized. Cancer Cell. Nov. 2006;10(5):389-99.

Wei et al., The v-Jun point mutation allows c-Jun to escape GSK3-dependent recognition and destruction by the Fbw7 ubiquitin ligase. Cancer Cell. Jul. 2005;8(1):25-33.

Welcker et al., FBW7 ubiquitin ligase: a tumour suppressor at the crossroads of cell division, growth and differentiation. Nat Rev Cancer. Feb. 2008;8(2):83-93.

Welcker et al., The Fbw7 tumor suppressor regulates glycogen synthase kinase 3 phosphorylation-dependent c-Myc protein degradation. Proc Natl Acad Sci U S A. Jun. 15, 2004;101(24):9085-90. Epub May 18, 2004.

Wertz et al., Sensitivity to antitubulin chemotherapeutics is regulated by MCL1 and FBW7. Nature. Mar. 3, 2011;471(7336):110-4. doi: 10.1038/nature09779. Abstract only.

Wood et al., The genomic landscapes of human breast and colorectal cancers. Science. Nov. 16, 2007;318(5853):1108-13. Epub Oct. 11, 2007.

Yu et al., The role of Mcl-1 downregulation in the proapoptotic activity of the multikinase inhibitor BAY 43/9006. Oncogene. Oct. 20, 2005;24(46):6861-9.

Zhong et al., Mule/ARF-BP1, a BH3-only E3 ubiquitin ligase, catalyzes the polyubiquitination of Mcl-1 and regulates apoptosis. Cell. Jul. 1, 2005;121(7):1085-95.

Stewart et al., The MCL-1 BH3 helix is an exclusive MCL-1 inhibitor and apoptosis sensitizer. Nat Chem Biol. Aug. 2010;6(8):595-601. doi: 10.1038/nchembio.391.

Genbank Submission; GenPept; AAF64255.1; Jul. 17, 2000. Bingle et al.

Bird et al., Synthesis and biophysical characterization of stabilized alpha-helices of BCL-2 domains. Methods Enzymol. 2008;446:369-86. doi: 10.1016/S0076-6879(08)01622-4.

Day et al., Solution structure of prosurvival Mcl-1 and characterization of its binding by proapoptotic BH3-only ligands. J Biol Chem. Feb. 11, 2005;280(6):4738-44. Epub Nov. 18, 2004.

\* cited by examiner c

Predicted Fragmentation Pattern

| Seq | # | b | y | +1 |
|---|---|---|---|---|
| S* | 1 | 168.00 | --- | 18 |
| L | 2 | 281.08 | 2051.88 | 17 |
| P | 3 | 378.13 | 1938.80 | 16 |
| S | 4 | 465.16 | 1841.74 | 15 |
| T* | 5 | 646.17 | 1754.72 | 14 |
| P | 6 | 743.22 | 1573.71 | 13 |
| P | 7 | 840.28 | 1476.65 | 12 |
| P | 8 | 937.33 | 1379.60 | 11 |
| A | 9 | 1008.37 | 1282.55 | 10 |
| E | 10 | 1137.41 | 1211.51 | 9 |
| E | 11 | 1266.45 | 1082.47 | 8 |
| E | 12 | 1395.49 | 953.43 | 7 |
| E | 13 | 1324.54 | 824.38 | 6 |
| D | 14 | 1639.56 | 695.34 | 5 |
| E | 15 | 1768.61 | 580.31 | 4 |
| L | 16 | 1881.69 | 451.27 | 3 |
| Y | 17 | 2044.75 | 338.19 | 2 |
| R | 18 | --- | 175.12 | 1 | z = 2
PPM = -0.53
XCorr = 3.964
Ascore = 28.87/28.87

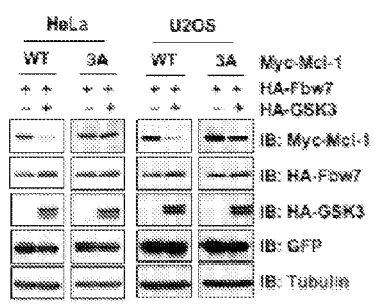
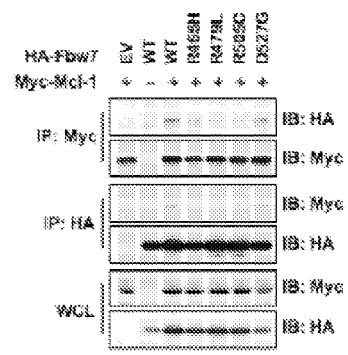
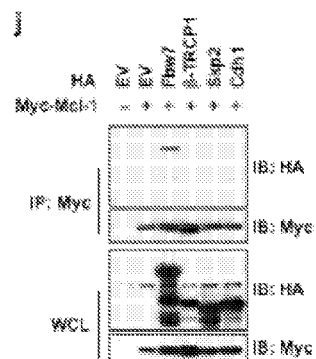
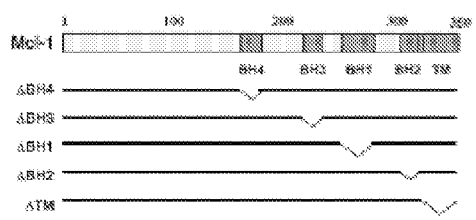
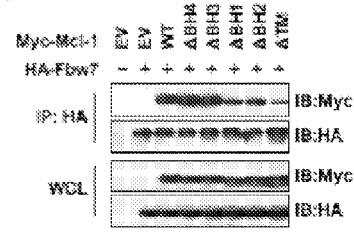
Figure 8-2

MCL-1 AS A THERAPEUTIC TARGET IN SCFFBW7 DEFICIENT NEOPLASM

RELATED APPLICATIONS

This application is a 35 U.S.C. § 371 National Phase Application of International Application No. PCT/US2012/027516, filed Mar. 2, 2012, and entitled "MCL-1 AS A THERAPEUTIC TARGET IN SCF$^{FBW7}$ DEFICIENT NEOPLASM," which claims the benefit under 35 U.S.C. § 119(e) of U.S. provisional application 61/448,648, filed Mar. 2, 2011, and entitled "SCF$^{Fbw7}$ Regulates Cellular Apoptosis By Targeting Mcl-1 for Ubiquitination and Destruction," the entire contents of which are incorporated herein by reference.

GOVERNMENT SUPPORT

This invention was made with government support under grant number GM089763 awarded by the National Institutes of Health. The Government has certain rights in the invention.

BACKGROUND OF THE INVENTION

Loss of the FBW7 tumor suppressor gene has previously been reported to be associated with various types of human cancers, including breast cancer, colon cancer, and T-cell acute lymphoblastic leukemia. The molecular mechanism by which FBW7 functions as a tumor suppressor has not been elucidated, however.

SUMMARY OF THE INVENTION

Some embodiments are based on the surprising discovery that that the tumor suppressor FBW7 (also commonly referred to as FBXW7 or hCDC4, or, in some species as Sel-10 (worm) or Ago), is a regulator of the pro-survival Bcl2 family member Mcl-1, an oncogene that is associated with some forms of cancer, for example, with leukemia. Some aspects of this invention are based on the surprising discovery that FBW7 promotes the degradation of Mcl-1.

Some embodiments are based on the recognition that Mcl-1 protein levels in a cell, for example, in a malignant cell, can be considered an arbiter of whether the cell will evade apoptosis, and thus, be prone to a cancerous phenotype. Measuring Mcl-1 protein levels is difficult, however, because it is extremely unstable relative to its other Bcl2 family members. Some aspects of this invention relate to the recognition that determining the level of FBW7 or detecting a mutation in the FBW7 gene is predictive of Mcl-1 protein levels and, thus, useful as a diagnostic marker in human cancer. In some embodiments, this invention provides a genetic FBW7-based biomarker for cancer diagnosis and classification. In some embodiments, for example, in some clinical settings, the assessment of a genomic biomarker, as provided by some aspects of this invention, is preferred over an assessment of a protein biomarker, since it is generally more reliable and easier to apply a diagnostic test that assesses genetic mutation status rather than to measure protein levels in a cell.

Some embodiments are based on the recognition that, if a cell, for example, a malignant cell, is FBW7 deficient, then it cannot degrade Mcl-1, creating a condition of 'oncogene addiction'. In some embodiments, a cell that bears a mutation in the FBW7 gene, for example, a missense, nonsense, or frameshift mutation, or a deletion of some or all of the coding region, or of all or some of the promoter region, or a splice site mutation, or any mutation that leads to a failure of the cell to express the full-length FBW7 protein, is considered to be FBW7 deficient. According to some aspects of this invention, FBW7(−) patients, e.g., patients carrying a cell, for example, a malignant cell, that is FBW deficient, therefore, are predicted, or indicated, to be responsive to drugs that inhibit Mcl-1. Mcl-1 inhibitors are well known to those of skill in the art and include, for example, multikinase inhibitors, e.g., sorafenib (aka BAY 43-90060R Nexavar) and other drugs that are known as inhibitors of Mcl-1 expression/activity, for example, Ceflatonin (e.g., Homoharringtonine (8CI), Omacetaxine Mepesuccinate), Seliciclib (CYC202), AT-101, CNDO103, and Obatoclax. Other drugs that inhibit Mcl-1, including siRNAs and RNAi nucleic acids targeting Mcl-1, will be apparent to those of skill in the art and the invention is not limited in this respect.

Some aspects of this invention relate to the recognition that FBW7-deficiency in a cell, for example, a malignant cell, is an indicator for the cell being resistant to pro-apoptotic drugs, for example, to Bcl2 inhibitors (e.g., ABT-737 (CAS No.: 852808-04-9), ABT-263 (Navitoclax, CAS No.: 923564-51-6)) or any other Bcl2-antagonists described herein. Accordingly, malignant cells that are FBW7-deficient will not respond to treatment with pro-apoptotic drugs, particularly to treatment with pro-apoptotic drugs that do not inactivate Mcl-1, for example, to ABT-737 or ABT-263 treatment. According to some aspects of this invention, FBW7(−) patients, e.g., patients carrying a cell, for example, a malignant cell, that is FBW7 deficient, therefore, are predicted, or indicated, to be resistant to pro-apoptotic drugs. Pro-apoptotic drugs are well known to those of skill in the art and include, for example, Bcl2 antagonists or inhibitors (e.g., ABT-737, ABT-263). Other pro-apoptotic drugs, including siRNA and RNAi nucleic acids targeting anti-apoptotic gene products, e.g., Bcl2, will be apparent to those of skill in the art and the invention is not limited in this respect.

Some embodiments are based on the recognition that, if a cell, for example, a malignant cell, is not FBW7 deficient, for example, a cell that does not comprise an FBW7 mutation, or that expresses FBW7 at a level similar to that of a normal, healthy cell of the same tissue-of-origin, then Mcl-1 can be degraded by the FBW7-dependent SCW$^{FBW7}$ complex. A subject carrying a neoplastic or malignant cell that is not FBW7 deficient, for example, a subject with unmutated FBW7, accordingly, is indicated to not be sensitive to a Mcl-1 inhibitor (e.g., sorafenib), but instead will be sensitive to other cancer drugs that otherwise fail to inactivate Mcl-1 like ABT-737 (or congeners).

In some embodiments, an FBW7-based biomarker for cancer diagnosis and classification is provided. In some embodiments, the biomarker is a genomic FBW7 biomarker. In some embodiments, a mutation in the FBW7 gene of a diseased cell, is indicative of the cell being FBW7-deficient. In some embodiments, a mutation in the FBW7 gene of a diseased cell, for example, a neoplastic cell or a malignant cell, is indicative of the cell's susceptibility to a drug that inhibits Mcl-1, for example, to a multikinase inhibitor (e.g. sorafenib). In some embodiments, a mutation in the FBW7 gene of a diseased cell, for example, a neoplastic cell or a malignant cell, is indicative of the cell's resistance to a pro-apoptotic drug, for example, a drug that inhibits Bcl2. In some embodiments, the absence of a mutation in the FBW7 gene of a diseased cell, for example, a neoplastic cell or a malignant cell, is indicative of the cell's susceptibility to a pro-apoptotic drug, for example, a drug that inhibits Bcl2. In some embodiments.

The term "mutation" as used herein, refers to any alteration in a wild-type nucleic acid sequence, coding or non-coding, that affects the expression of a gene. In some embodiments, "expression of a gene" refers to expression of a functional gene product, for example, to expression of a functional protein (e.g., a wild-type protein or a protein comprising a mutation as compared to the wild-type protein that might leads to compromised function of the mutant protein). In the case of the FBW7 gene, a mutation, accordingly, is an alteration in the wild-type FBW7 genomic sequence that alters the expression of the FBW7 protein, including, but not limited to, a deletion, totally or partially, of an FBW7 coding sequence, or of an FBW7 promoter sequence, a deletion or alteration of an FBW7 splice site (a splice site mutation) leading to aberrant splicing of the FBW7 transcript, a partial or complete deletion of the FBW7 gene, a partial or complete deletion of the FBW7 coding region, a nonsense mutation, a missense mutation, a frameshift mutation, a mutation causing a truncation of the FBW7 protein, or a splice site mutation, or a point mutation resulting in an amino acid substitution. Amino acid substitutions associated with FBW deficiency, as provided by aspects of this invention, are well known to those of skill in the art, and include, for example, a G423 mutation, a R456 mutation, mutation, a R479 mutation, a R479 mutation, a R505 mutation, a D527 mutation, or a S668 mutation, for example, a G423V mutation, a R456c mutation, a R456H mutation, a R479L mutation, a R479Q mutation, a R505c mutation, a D527G mutation, an Exon 8 splice site mutation, or a S668 frameshift mutation.G423V. Additional mutations associated with FBW7 deficiency are well known to those of skill in the art, for example, as described in FIG. 6C and relating text of Maser, R. S. et al. Chromosomally unstable mouse tumours have genomic alterations similar to diverse human cancers. Nature 447, 966-71 (2007), which is incorporated herein by reference. It should be noted that the invention is not limited in this respect.

Methods for the detection of mutations, for example, of FBW7 mutations as provided herein are well known to those of skill in the art and include, but are not limited to, isolation and sequencing of genomic DNA, FBW7-encoding mRNA, or cDNA derived therefrom, mRNA profiling (e.g. to detect underabundance of mRNA or to detect truncated mRNA, gene-chip (e.g., to detect an underabundance of FBW7 sequences in the genome), massive parallel sequencing technologies, PCR, RT-PCR, and hybridization-based methods, for example, SNP arrays, or southern or northern blot. Any of these methods can be used to detect an FBW7 mutation as described herein and other methods useful to detect an FBW7 mutation in embodiments of this invention will be apparent to those of skill in the art, as the invention is not limited in this respect.

In some embodiments, a method for cancer diagnosis is based on an assessment of FBW7, for examples, in a tumor of a subject diagnosed with a cancer. In some embodiments, the method comprises obtaining a sample, for example, a sample comprising a diseased cell, for example, a malignant cell, from a subject diagnosed with a proliferative disease, for example, with a cancer. In some embodiments, the method further comprises assessing the FBW7 gene for a mutation or a plurality of mutations in the sample or cell. For example, in some embodiments, the method comprises isolating genomic DNA from the cell and sequencing the FBW7 genomic locus or a part thereof or hybridizing the genomic DNA, or complementary DNA to a SNP array. In some embodiments, if a mutation of the FBW7 locus is detected, the cell is identified as FBW7-deficient. In some embodiments, a cell comprising an FBW7 mutation is defined as FBW7-deficient only if the mutation is a mutation described herein, for example, a deletion, totally or partially, of an FBW7 coding sequence, or of an FBW7 promoter sequence, a deletion or alteration of an FBW7 splice site (a splice site mutation) leading to aberrant splicing of the FBW7 transcript, a partial or complete deletion of the FBW7 gene, a partial or complete deletion of the FBW7 coding region, a nonsense mutation, a missense mutation, a frameshift mutation, a mutation causing a truncation of the FBW7 protein, or a splice site mutation, or a point mutation resulting in an amino acid substitution. Amino acid substitutions associated with FBW deficiency, as provided by aspects of this invention, are well known to those of skill in the art, and include, for example, a G423 mutation, a R456 mutation, a R479 mutation, a R479 mutation, a R505 mutation, a D527 mutation, or a S668 mutation, a G423V mutation, a R456c mutation, a R456H mutation, a R479L mutation, a R479Q mutation, a R505c mutation, a D527G mutation, an Exon 8 splice site mutation, or a S668 frameshift mutation. In some embodiments, the cell is obtained from the subject by biopsy, for example, by biopsy from a tumor, or by obtaining a blood sample comprising the cell, for example, a leukemia cell. In some embodiments, the cell is a diseased cell, e.g., a malignant cell, and the method further comprises selecting a treatment appropriate for the disease, e.g., a tumor or cancer, based on the FBW7 mutation status. In some embodiments, if the cell is identified as FBW7 deficient, the subject is indicated to be a candidate for treatment with a drug inhibiting Mcl-1. In some embodiments, the method comprises selecting and/or administering to the subject an Mcl-1 inhibitor based on the cell being identified as FBW7-deficient. In some embodiments, if the cell is identified to not be FBW7 deficient, e.g., a cell that does not carry an FBW7 mutation as described herein, the subject is not indicated to be a candidate for treatment with a drug inhibiting Mcl-1. In some embodiments, if the cell is identified to not be FBW7 deficient, e.g., a cell that does not carry an FBW7 mutation as described herein, the subject is indicated to not be a candidate for treatment with a drug inhibiting Mcl-1. In some embodiments, if the cell is identified to not be FBW7 deficient, e.g., a cell that does not carry an FBW7 mutation as described herein, the subject is indicated to be a candidate for treatment with a pro-apoptotic drug. Several suitable Mcl-1 inhibitors are described herein and are well known to those of skill in the art and include multikinase inhibitors, e.g. sorafenib (e.g., BAY 43-9006 or Nexavar), Ceflatonin (e.g., Homoharringtonine (8CI), Omacetaxine Mepesuccinate), R-roscovitine (e.g., Seliciclib or CYC202), AT-101 (e.g., CAS No: 90141-22-3), apogossypol (e.g., CNDO103), Sabutoclax (e.g., BI-97C1), or Obatoclax (e.g., CAS No: 803712-67-6, 803712-79-0). Similarly, pro-apoptotic drugs are well known to those of skill in the art and include Bcl2-inhibitors, e.g., ABT-737. Additional suitable Mcl-1 inhibitors and pro-apoptotic drugs will be apparent to those of skill in the art, and the invention is not limited in this respect.

In some embodiments, the cells assessed for FBW7 mutation status and/or expression level by the methods provided herein are diseased cells, e.g., cells that are causing a disease or are symptomatic for a disease. In some embodiments, the cells are aberrantly proliferating cells and the disease is a proliferative disease. In some embodiments, the cells are neoplastic cells and the disease is a neoplastic disease. In some embodiments, the cells are malignant cells and the disease is a malignant disease. In some embodiments, the cells are part of a tumor, for example, of a solid tumor or of a liquid tumor. In some embodiments, the tumor is the manifestation of a cancer, for example, lung cancer, breast cancer, colon cancer, blood cancer (e.g., leukemia such as T-ALL), lymphoma, melanoma, pancreatic cancer, or skin cancer. In some embodiments, the proliferative disease is a neoplastic disease.

In some embodiments, a method for cancer classification is based on an assessment of FBW7, for example, in a tumor of a subject diagnosed with a cancer. In some embodiments, the method comprises obtaining a cancer cell, for example, a cell of a solid or a liquid tumor from a subject diagnosed with a cancer. In some embodiments, the method comprises assessing the cell for a mutation of the FBW7 gene. In some embodiments, this assessment comprises isolating the genomic DNA of the cell and obtaining sequence information of the FBW7 gene locus, for example, by sequencing all or part of the locus, or by performing a SNP analysis, or by any other method described herein or known to those of skill in the art to be useful to obtain sequence information. In some embodiments, the method comprises identifying the cell as FBW7-deficient if a mutation is detected, or FBW7-normal, if a mutation is not detected. In some embodiments, the method further comprises classifying the cancer as FBW7-deficient or FBW7-normal, based on whether the cell is identified as FBW7-deficient or FBW7-normal. In some embodiments, the method further comprises indicating that the cancer is sensitive to treatment with a drug inhibiting Mcl-1 based on the cell being identified as FBW7-deficient. the method further comprises indicating that the cancer is resistant to treatment with a drug inhibiting Mcl-1 based on the cell being identified as FBW7-deficient. the method further comprises indicating that the cancer is sensitive to treatment with a pro-apoptotic drug based on the cell being identified as FBW7-normal. In some embodiments, the method further comprises selecting an appropriate drug for treatment of the cancer based on FBW7 mutation status of the cell. For example, in some embodiments, the method comprises selecting an Mcl-1 inhibitor for the treatment of a cancer that is identified to be FBW7 deficient. In some embodiments, the method comprises selecting a pro-apoptotic drug for the treatment of a cancer that is identified to be FBW7-normal. In some embodiments, the method further comprises administering the selected drug to the subject, for example, administering a multikinase inhibitor targeting Mcl-1 (e.g., sorafenib or seliciclib) to a subject having a cancer identified to be FBW7-deficient or administering a pro-apoptotic drug (e.g. a Bcl2-antagonist such as ABT737, ABT-263) to a subject having a cancer that is identified to be FBW7-normal.

In some embodiments, a method for cancer therapy is based on an assessment of FBW7, for example, in a tumor of a subject diagnosed with a cancer. In some embodiments, the method comprises administering a multi-kinase inhibitor to a subject having a tumor based on the tumor exhibiting a decreased level of FBW7 expression and/or a mutation in the SFBW7 gene in the tumor. In some embodiments, the method further comprises determining that the tumor exhibits a decreased level of FBW7 expression and/or a mutation in the FBW7 gene. In some embodiments, the multikinase inhibitor is a multikinase inhibitor described herein, for example, sorafenib, or seliciclib (CYC202).

In some embodiments, a method is provided that comprises administering a pro-apoptotic drug to a subject having a tumor based on the tumor exhibiting a normal or increased level of FBW7 expression and/or no mutation in the FBW7 gene in the tumor. In some embodiments, the method further comprises determining that the tumor does not exhibit a decreased level of FBW7 expression and/or a mutation in the FBW7 gene, for example, via a method described herein or otherwise known to those of skill in the art. In some embodiments, the pro-apoptotic drug is a Bcl2-inhibitor. In some embodiments, the Bcl2-inhibitor is ABT-737, ABT-737, Ceflatonin (e.g., Homoharringtonine (8CI), Omacetaxine Mepesuccinate), Obatoclax, CNDO103, or AT-101.

DETAILED DESCRIPTION

Figure 1:
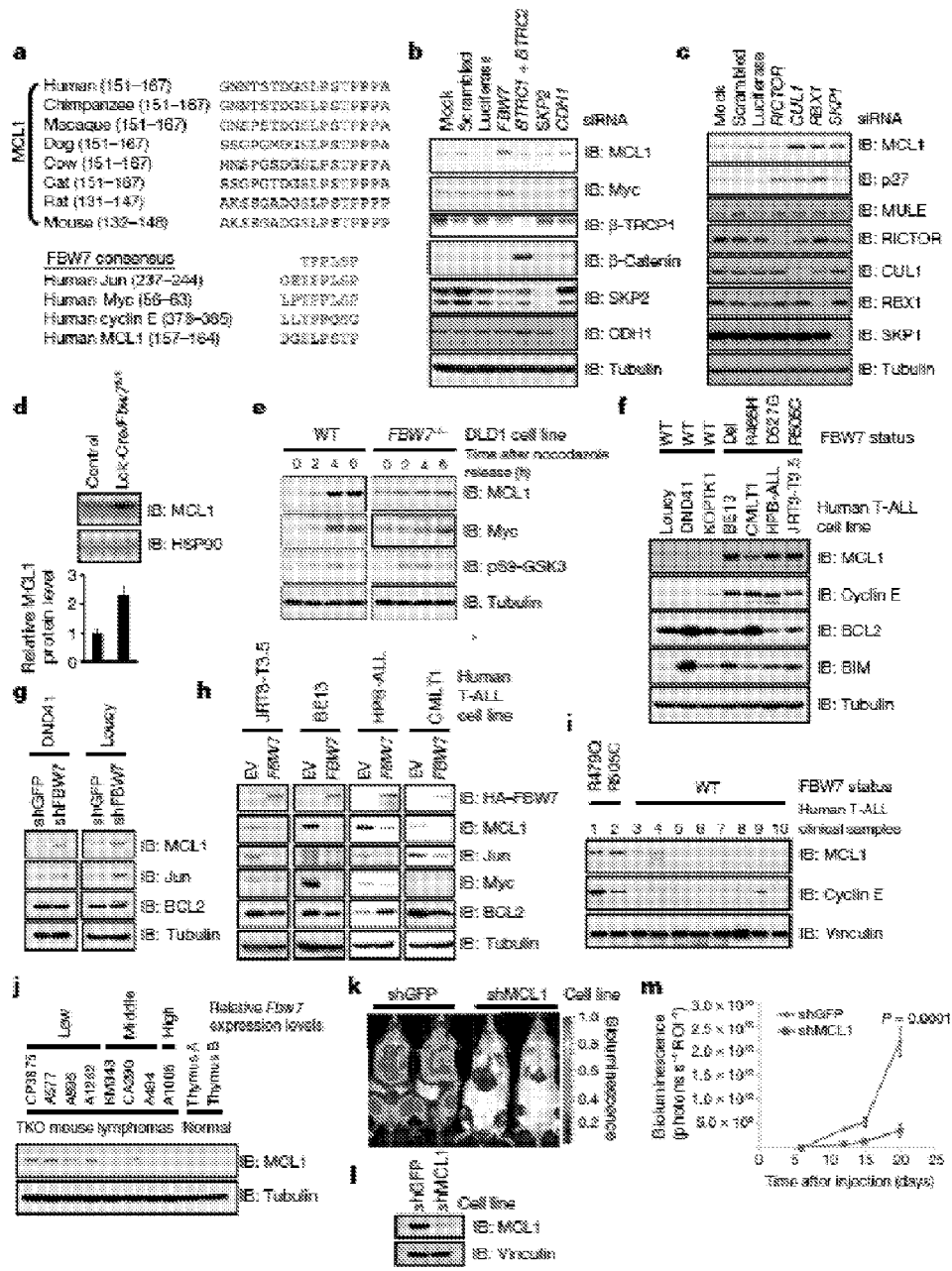
FIG. 1 shows that Mcl-1 stability is controlled by Fbw7. Sequences in 1a correspond, from top to bottom, to SEQ ID NOs 1-13, respectively.

Some embodiments are based on the discovery that proliferative diseases (e.g., neoplastic diseases, for example, tumors or cancers) having a FBW7 mutation or other deficiency are sensitive to Mcl1 inhibiting agents, but resistant to pro-apoptotic drugs that do not inhibit Mcn. Accordingly, subjects having a proliferative disease associated with an FBW7 deficiency should be treated with an Mcl1 inhibitor, alone or in combination with one or more additional therapeutic agents. It should be appreciated, that an Mcl1 inhibitor may be useful to prevent unwanted proliferation or may be used to help prevent unwanted proliferation by rendering diseased cells or tissue more sensitive to other agents.

For example, some embodiments are based on the recognition that if a subject having a proliferative disease presents with FBW7 deficiency, the disease will not be responsive to therapy with Bcl-2 inhibitors (e.g., ABT-737 and functional pro-apoptotic congeners, like ABT-263, RG7433, AT-101, EU-517, ABT-199, CNDO103, CND0113, CND0123, CND0133). Some embodiments are based on the recognition that such subjects should not be treated with Bcl-2 inhibitors, but should be treated with a drug that inhibits Mcl-1, e.g., by decreasing Mcl-1 expression, function, or bioavailability.

Similarly, some embodiments are based on the recognition that if a subject having a proliferative disease presents with wild-type, or normal, levels of FBW7, the disease will be responsive to therapy with Bcl-2 inhibitors (e.g., ABT-737 and functional pro-apoptotic congeners, like Navitoclax (e.g., ABT-263, RG7433), AT-101, EU-517, BH-3 mimetics, ABT-199, CNDO103, CND0113, CND0123, CND0133). Some embodiments are based on the recognition that such subjects should be treated with Bcl-2 inhibitors.

The term "Mcl1" refers to induced myeloid leukemia cell differentiation protein MeI-1. The term can refer to a protein and/or encoding nucleic acid sequence. Mcl1 sequences are well known to those of skill in the art and Mcl1 protein sequences include, for example, the following human sequences:

```
>gi|11386165|ref|NP_068779.1| induced myeloid leukemia cell
differentiation protein Mcl-1 isoform 1 [Homo sapiens]
                                                            (SEQ ID NO: 25)
MFGLKRNAVIGLNLYCGGAGLGAGSGGATRPGGRLLATEKEASARREIGGGEAGAVIGGSAGASPPSTLT

PDSRRVARPPPIGAEVPDVTATPARLLFFAPTRRAAPLEEMEAPAADAIMSPEEELDGYEPEPLGKRPAV

LPLLELVGESGNNTSTDGSLPSTPPPAEEEEDELYRQSLEIISRYLREQATGAKDTKPMGRSGATSRKAL

ETLRRVGDGVQRNHETAFQGMLRKLDIKNEDDVKSLSRVMIHVFSDGVTNWGRIVTLISFGAFVAKHLKT

INQESCIEPLAESITDVLVRTKRDWLVKQRGWDGFVEFFHVEDLEGGIRNVLLAFAGVAGVGAGLAYLIR

>gi|33519458|ref|NP_877495.1| induced myeloid leukemia cell
differentiation protein Mcl-1 isoform 2 [Homo sapiens]:
                                                            (SEQ ID NO: 26)
MFGLKRNAVIGLNLYCGGAGLGAGSGGATRPGGRLLATEKEASARREIGGGEAGAVIGGSAGASPPSTLT

PDSRRVARPPPIGAEVPDVTATPARLLFFAPTRRAAPLEEMEAPAADAIMSPEEELDGYEPEPLGKRPAV

LPLLELVGESGNNTSTDGSLPSTPPPAEEEEDELYRQSLEIISRYLREQATGAKDTKPMGRSGATSRKAL

ETLRRVGDGVQRNHETAFQGWVCGVLPCRGPRRWHQECAAGFCRCCWSRSWFGISNKIALL
```

Additional Mcl1 sequences, for example, Mcl1 encoding sequences, such as DNA and mRNA sequences and additional protein sequences, for example, Mcl1 sequences from other species will be readily apparent to those of skill based on the instant disclosure.

The term "FBW7," interchangeably used herein with the term "SCFF$^{BW7}$" refers to F-box/WD repeat-containing protein 7. The term can refer to a protein and/or encoding nucleic acid sequence. FBW7 sequences are well known to those of skill in the art and FBW7 protein sequences include, for example, the following human sequences:

```
>gi|16117781|ref|NP_361014.1| F-box/WD repeat-containing protein 7
isoform 1 [Homo sapiens]
                                                            (SEQ ID NO: 27)
MNQELLSVGSKRRRTGGSLRGNPSSSQVDEEQMNRVVEEEQQQQLRQQEEEHTARNGEVVGVEPRPGGQN

DSQQGQLEENNNRFISVDEDSSGNQEEQEEDEEHAGEQDEEDEEEEEMDQESDDFDQSDDSSREDEHTHT

NSVTNSSSIVDLPVHQLSSPFYTKTTKMKRKLDHGSEVRSFSLGKKPCKVSEYTSTTGLVPCSATPTTFG

DLRAANGQGQQRRRITSVQPPTGLQEWLKMFQSWSGPEKLLALDELIDSCEPTQVKHMMQVIEPQFQRDF

ISLLPKELALYVLSFLEPKDLLQAAQTCRYWRILAEDNLLWREKCKEEGIDEPLHIKRRKVIKPGFIHSP

WKSAYIRQHRIDTNWRRGELKSPKVLKGHDDHVITCLQFCGNRIVSGSDDNTLKVWSAVTGKCLRTLVGH

TGGVWSSQMRDNIIISGSTDRTLKVWNAETGECIHTLYGHTSTVRCMHLHEKRVVSGSRDATLRVWDIET

GQCLHVLMGHVAAVRCVQYDGRRVVSGAYDFMVKVWDPETETCLHTLQGHTNRVYSLQFDGIHVVSGSLD

TSIRVWDVETGNCIHTLTGHQSLTSGMELKDNILVSGNADSTVKIWDIKTGQCLQTLQGPNKHQSAVTCL

QFNKNEVITSSDDGTVKLWDLKTGEFIRNLVTLESGGSGGVVWRIRASNTKLVCAVGSRNGTEETKLLVL

DFDVDMK
```

-continued

>gi|16117779|ref|NP_060785.2| F-box/WD repeat-containing protein 7
isoform 2 [Homo sapiens]

(SEQ ID NO: 28)

MCVPRSGLILSCICLYCGVLLPVLLPNLPFLTCLSMSTLESVTYLPEKGLYCQRLPSSRTHGGTESLKGK

NTENMGFYGTLKMIFYKMKRKLDHGSEVRSFSLGKKPCKVSEYTSTTGLVPCSATPTTFGDLRAANGQGQ

QRRRITSVQPPTGLQEWLKMFQSWSGPEKLLALDELIDSCEPTQVKHMMQVIEPQFQRDFISLLPKELAL

YVLSFLEPKDLLQAAQTCRYWRILAEDNLLWREKCKEEGIDEPLHIKRRKVIKPGFIHSPWKSAYIRQHR

IDTNWRRGELKSPKVLKGHDDHVITCLQFCGNRIVSGSDDNTLKVWSAVTGKCLRTLVGHTGGVWSSQMR

DNIIISGSTDRTLKVWNAETGECIHTLYGHTSTVRCMHLHEKRVVSGSRDATLRVWDIETGQCLHVLMGH

VAAVRCVQYDGRRVVSGAYDFMVKVWDPETETCLHTLQGHTNRVYSLQFDGIHVVSGSLDTSIRVWDVET

GNCIHTLTGHQSLTSGMELKDNILVSGNADSTVKINDIKTGQCLQTLQGPNKHQSAVTCLQFNKNFVITS

SDDGTVKLWDLKTGEFIRNLVTLESGGSGGVVWRIRASNTKLVCAVGSRNGTEETKLLVLDFDVDMK

>gi|61743926|ref|NP_001013433.1| F-box/WD repeat-containing protein
7 isoform 3 [Homo sapiens]

(SEQ ID NO: 29)

MSKPGKPTLNHGLVPVDLKSAKEPLPHQTVMKIFSISIIAQGLPFCRRRMKRKLDHGSEVRSFSLGKKPC

KVSEYTSTTGLVPCSATPTTFGDLRAANGQGQQRRRITSVQPPTGLQEWLKMFQSWSGPEKLLALDELID

SCEPTQVKHMMQVIEPQFQRDFISLLPKELALYVLSFLEPKDLLQAAQTCRYWRILAEDNLLWREKCKEE

GIDEPLHIKRRKVIKPGFIHSPWKSAYIRQHRIDTNWRRGELKSPKVLKGHDDHVITCLQFCGNRIVSGS

DDNTLKVWSAVTGKCLRTLVGHTGGVWSSQMRDNIIISGSTDRTLKVWNAETGECIHTLYGHTSTVRCMH

LHEKRVVSGSRDATLRVWDIETGQCLHVLMGHVAAVRCVQYDGRRVVSGAYDFMVKVWDPETETCLHTLQ

GHTNRVYSLQFDGIHVVSGSLDTSIRVWDVETGNCIHTLTGHQSLTSGMELKDNILVSGNADSTVKIWDI

KTGQCLQTLQGPNKHQSAVTCLQFNKNFVITSSDDGTVKLWDLKTGEFIRNLVTLESGGSGGVVWRIRAS

NTKLVCAVGSRNGTEETKLLVLDFDVDMK

Additional FBW7 sequences, for example, FBW7 encoding sequences, such as DNA and mRNA sequences and additional protein sequences, for example, FBW7 sequences from other species will be readily apparent to those of skill based on the instant disclosure.

Some embodiments involve a drug inhibiting Mcl-1, also referred to as an Mcl-1 inhibitor. In some embodiments, a drug inhibiting Mcl-1 inhibits a biological activity of Mcl-1. For example, in some embodiments, a drug inhibiting Mcl-1 diminishes a pro-survival, or anti-apoptotic function of Mcl-1. Some drugs inhibiting Mcl-1 bind Mcl-1 directly, some modulate the expression or biological activity of Mcl-1, and some bind or modulate the expression or biological activity of Mel-1-interacting proteins or upstream regulators or downstream effectors of Mcl-1 activity. For example, some drugs inhibiting Mcl-1 bind or modulate the expression or biological activity of a kinase or phosphatase targeting Mcl-1, or stabilize an Mcl-1 antagonist, or destabilize an Mcl-1 agonist. Mcl-1 agonists and antagonists as well as drugs targeting them are well known to those of skill in the art. Some drugs inhibiting Mcl-1 bind or modulate the expression or biological activity of an Mcl-1-interacting protein. Mel-1-interacting proteins are known to those of skill in the art and include, for example, BAK1, Noxa, BCL2L11, Bcl-2-associated death promoter, PCNA, DAD1, TNKS, and/or BH3 interacting domain death agonist. Drugs targeting, binding, and/or modulating the biological activity of Mcl-1 interacting proteins are well known to those of skill in the art. Accordingly, the term "inhibiting Mcl-1," in some embodiments, refers to direct inhibition of a biological function of Mcl-1, and in some embodiments, it refers to indirect inhibition of Mcl-1, for example, by modulation of an upstream regulator or a downstream effector of Mcl-1 signaling activity. For example, the kinase inhibitor sorafenib is a drug inhibiting Mcl-1, even though it does not directly bind to Mcl-1, but acts upstream or otherwise indirectly to inhibit Mcl-1 activity and/or expression level.

The term "proliferative disease" is a term of art and is used herein interchangeably with the term neoplastic disease. In some embodiments, the term refers to a disease or disorder associated with a neoplastic cell population (also referred to as a neoplasm). Neoplasia refers to an abnormal proliferation of cells. The growth of neoplastic cells exceeds and is typically not coordinated with that of the normal tissues around it. A neoplasm can take the form of a tumor, e.g., a benign or a malign tumor.

The methods provided herein are useful to classify, select a course of treatment for, and/or treat any neoplastic disorder in which FBW7 deficiency can be detected or that are associated with FBW7 deficiency. For example, the methods provided herein are useful to classify neoplastic diseases including, but not limited to, breast cancer, colon cancer, gastric cancer, prostate cancer, pancreatic cancer, lung cancer, hepatic cancer, brain cancer, kidney cancer, hematologic proliferative disorders, blood cancer (e.g., leukemia, such as acute lymphoblastic leukemia (ALL), chronic lymphocytic leukemia (CLL), acute myelogenous leukemia (AML), chronic myelogenous leukemia (CML), hairy cell leukemia, T-cell prolymphocytic leukemia, juvenile myelomonocytic ALL, or T-cell acute lymphoblastic leukemia (T-ALL). Other neoplastic diseases or disorders in which loss of FBW7 can be detected or which are associated with loss of FBW7 are known to those of skill in the art and this disclosure is not limited in this respect.

The term "tumor" as used herein, refers to a neoplastic cell growth, including benign, malignant, pre-cancerous and/or cancerous cell neoplasms. A tumor may be a liquid tumor, for example, a leukemic tumor, or a solid tumor, for example, an ovarian epithelial tumor, a breast tumor, a colon tumor, a gastric tumor, a prostate tumor, a pancreatic tumor, a lung tumor, a liver tumor, a brain tumor, or a kidney tumor. In some embodiments, the tumor is an epithelial tumor. In some embodiments, the tumor is a tumor harboring a cell with a defect in homologous recombination. In some embodiments, the tumor may be the manifestation of a cancer, for example, blood cancer, ovarian epithelial cancer, breast cancer, colon cancer, gastric cancer, prostate cancer, pancreatic cancer, lung cancer, liver cancer, brain cancer, or kidney cancer. The term tumor also refers to cancers of other organs or tissues as aspects of the invention are not limited in this respect.

In some embodiments, the tumor being classified according to methods provided herein is a primary tumor. In some embodiments, the tumor being classified according to methods provided herein is a secondary, metastatic, or recurrent tumor.

The term "subject", as used herein, refers to an individual that may be, but is not limited to, a human, or a non-human mammal, for example, a mouse, rat, cow, sheep, cat, dog, or goat.

In some embodiments, a method for the diagnostic classification of a cancer tumor as chemoresistant or chemosensitive is provided. In some embodiments, the method includes obtaining information about the presence or absence of one or more gene mutations, and/or an increase or decrease in expression levels as described herein. A positive result (e.g., the detection of) one or more gene mutations, and/or an increase or decrease in expression levels as described herein can be obtained from a cell or a tissue from a tumor, for example, from a tumor biopsy, or from any other biological sample that includes tumor material (e.g., intact tumor cells and/or cellular debris derived from tumor cells). It should be appreciated that a sample also can contain normal cells or material (e.g., non-tumor cells or debris). However, in some embodiments, the relative amount of tumor cells or material is sufficient to determine whether an FBW7 deficiency is present in a tumor or not.

The term "expression level", as used herein, refers to information about the level of one or more gene products (e.g., an mRNA, a protein, or a combination thereof) in a cell or tissue. In some embodiments, the detection of one or more gene mutations, and/or an increase or decrease in expression levels as described herein may be based on one or more measurements or assays, for example, a quantitative or semi-quantitative value of expression of a single gene, for example, reflective of the signal obtained from a quantitative or semi-quantitative assay detecting the abundance of a gene product (e.g., a protein or a nucleic acid transcript). Suitable assays for the detection of gene expression products are well known to those of skill in the art and include, for example, western blots, ELISA, RT-PCR (e.g., end-point RT-PCR, real-time PCR, or qPCR), protein or nucleic acid microarray, and massive parallel sequencing assays. However, any suitable assay may be used based on hybridization, specific binding (e.g., antibody binding), or any other technique, as aspects of the invention are not limited in this respect. In some embodiments, the presence of one or more gene mutations, and/or an increase or decrease in expression levels as described herein may involve a plurality of data points, for example, quantitative or semi-quantitative values of expression and/or one or sequence or mutation data points. In some embodiments, the presence of one or more gene mutations, and/or an increase or decrease in expression levels as described herein may be evaluated in a disease tissue sample (e.g., a biopsy sample) or in any suitable patient sample. Methods for the detection or for the generation of data for one or more gene mutations, and/or an increase or decrease in expression levels as described herein are well known to those in the art and include, for example, southern blot, western blot, ELISA, northern blot, reverse northern blot, RT-PCR (e.g. endpoint, real time, or qPCR), microarray (for either protein or transcript detection), SNP analysis, PCR, hybridization assays, sequencing assays, etc., or any combination thereof (for exemplary detection methods, see, e.g., Sambrook et al., *Molecular Cloning: A Laboratory Manual, Third Edition* (3 Volume Set), Cold Spring Harbor Laboratory Press; 3rd edition (Jan. 15, 2001), ISBN-10: 0879695773; Robert Grützmann (Editor), Christian Pilarsky (Editor), *Cancer Gene Profiling: Methods and Protocols (Methods in Molecular Biology)*, Humana Press; 1$^{st}$ edition (Nov. 6, 2009), ISBN-10: 1934115762, both incorporated herein by reference for disclosure of gene product detection and expression profiling methods).

Further, methods to generate comprehensive transcript levels for one or more genes (e.g., wild type alleles and/or mutations) from a given cell or tissue are well known in the art.

In some embodiments, a quantitative expression value is a value reflecting the abundance of a gene transcript in the starting sample, for example, a tumor cell or tissue sample. In some embodiments, a semi-quantitative expression value is a value reflecting the abundance of a gene transcript in the starting sample in relation to a control or reference quantity. In some embodiments, a semi-quantitative value may be a non-numeric indication of gene regulation (e.g., "up", "down", "+", "++", "+++", "−", "−−", or "−−−"). In some embodiments, a semi-quantitative expression value may give a numeric dimension of gene regulation (e.g., "1.5-fold upregulated", "2.456", "0.32" or "−1.5"). Methods of calculating semi-quantitative expression values are well known to those in the art. Appropriate control or reference quantities for the generation of semi-quantitative expression values are well known to those in the art and include, for example, expression values of housekeeping genes (e.g., beta-actin or GAPDH), external controls (e.g., spiked in RNA or DNA controls not usually expressed in the cell to be analyzed), overall expression values (e.g., all expression values obtained from a cell added together), or historic or empiric values.

In some embodiments, an expression level of FBW7 (e.g., RNA and/or protein) that is determined for a sample is compared to a reference FBW7 expression level. In some embodiments, the reference is a standard that is indicative of a normal FBW7 expression level. In some embodiments, the reference is a standard that is indicative of a deficient FBW7 expression level (and any test levels that are at or below the reference would be indicative of an FBW7 deficiency). In some embodiments, a reference level is obtained by determining the expression level of FBW7 in a sample of normal or healthy tissue. In some embodiments, the reference level is determined by assaying FBW7 in a reference sample (e.g., a sample containing no malignant cells) obtained from the same subject from which a test sample (e.g., a sample containing or suspected of containing tumor cells or cellular material). The reference sample may be obtained from a different region of the same tissue or from a different region of the subject's body as the test sample.

It should be appreciated that expression levels of interest may be evaluated or determined in any suitable biological sample. In some embodiments, a biopsy of a tumor may be obtained and one or more gene mutations, and/or an increase or decrease in expression levels as described herein may be obtained from a biopsy cell or tissue. In some embodiments, one or more circulating cells (e.g., one or more circulating tumor cells) may be obtained and one or more gene mutations, and/or an increase or decrease in expression levels as described herein may be obtained from the cell or cells. In some embodiments, one or more tumor cells may be obtained from ascites fluid, peripheral blood, or from cerebrospinal fluid of a subject.

In some embodiments, a subject, or a biopsy or other biological sample obtained from a subject, is evaluated to determine whether a FBW deficiency, also referred to as FBW loss of function, is present, for example, detected as a genetic defect (e.g., deletion, loss of function, frameshift, inversion, or other mutation) or as a decreased level of FBW7 expression. It should be appreciated that any of the genetic and/or expression information described herein may be used alone or in combination, with or without additional patient information to assist in a prognosis, therapeutic recommendation, or other diagnostic or predictive evaluation of the health, outcome, and/or treatment for the patient.

In some embodiments, aspects of the invention relate to identifying patients that are candidates for one or more therapeutic treatments (e.g., one or more treatments such as small molecules, antibodies, antisense, hnRNA, siRNA, aptamer) that inhibit Mcl-1 gene products (e.g., transcripts or proteins), e.g., treatment with a multikinase inhibitor, such as sorafenib, or with Mcl-1 siRNAs. In some embodiments, aspects of the invention relate to identifying patients that should not be treated with one or more Mcl-1 inhibitory therapeutics agents described herein.

The terms "therapy", "therapeutic", "treat" or "treatment" refer to, but are not limited to, one or more clinical interventions with an intent to prevent, ameliorate, or cure a condition or symptoms of the condition in a subject, for example, a cancer or tumor, e.g., an FBW7-deficient or an FBW7-normal cancer or tumor.

In some embodiments, a treatment as provided by some aspects of this invention is aimed to eliminate a tumor, to induce a decrease in the size of a tumor, to induce a decrease in the number of tumor cells, or to inhibit or halt the growth of a tumor in a subject. Apparent to those skilled in the relevant medical arts, this can be accomplished by various approaches including, but not limited to, chemotherapeutic interventions. Suitable chemotherapeutic methods and administration schedules of chemotherapeutic compounds, alone or in combination with other therapeutics, will be apparent to those of skill in the relevant medical art.

Some methods for killing or inhibiting the proliferation of tumor cells, according to some embodiments of this invention, feature contacting such cells with a chemotherapeutic agent (e.g., in addition to one or more of the Mcl-1 inhibitory drugs or the pro-apoptotic drugs described herein), for example, a cytotoxic or cytostatic agent. In some embodiments, the cells are contacted with a chemotherapeutic agent, for example, a cytotoxic or cytostatic agent, that selectively targets tumor cells. By "selectively targeting" is meant that the agent or combination of agents selectively recognizes, binds, or acts upon tumor cells. In some embodiments, the agent or combination of agents can effectively kill tumor cells by one or more of several mechanisms, such as by induction of apoptosis, or by attracting other cells such as cytotoxic T lymphocytes or macrophages that can kill or inhibit proliferation of the targeted cells. By "cytotoxic or cytostatic agent" is meant an agent (for example a molecule) that kills or reduces proliferation of cells. Some examples of cytotoxic agents include, but are not limited to, cytotoxic radionuclides, chemical toxins, and protein toxins.

In some embodiments, the chemotherapeutic agent is a cytotoxic radionuclide or radiotherapeutic isotope, for example, an alpha-emitting isotope such as 225Ac, 211At, 212Bi, 213Bi, 212Pb, 224Ra or 223Ra. Alternatively, the cytotoxic radionuclide may a beta-emitting isotope such as 186Rh, 188Rh, 177Lu, 90Y, 131I, 67Cu, 64Cu, 153Sm or 166Ho. Further, the cytotoxic radionuclide may emit Auger and low energy electrons and may be one of the isotopes 125I, 123I or 77Br.

Chemotherapeutic compounds that can be used in combination with the Mcl-1 inhibitors or the pro-apoptotic drugs described herein are well known in the art, and non-limiting examples of suitable chemotherapeutic agents include, but are not limited to, alkylating agents, for example platinum compounds (e.g., carboplatin, cisplatin and oxaliplatin), mechlorethamine, cyclophosphamide, chlorambucil, and ifosfamide. PARP inhibitors are well known in the art, and non-limiting examples of PARP inhibitors include BSI201, AZD2281, ABT888, AG014699, MK4827, INO-1001, NU1025.

Other chemotherapeutic compounds are also well known to those of skill in the art, and non-limiting examples of such compounds include members of the enediyne family of molecules, such as calicheamicin and esperamicin. Chemical toxins can also be taken from the group consisting of methotrexate, doxorubicin, melphalan, chlorambucil, ARA-C, vindesine, mitomycin C, cis-platinum, etoposide, bleomycin and 5-fluorouracil. Examples of antineoplastic agents include, but are not limited to, dolastatins (U.S. Pat. Nos. 6,034,065 and 6,239,104) and derivatives thereof, for example, dolastatin 10 (dolavaline-valine-dolaisoleuine-dolaproine-dolaphenine) and the derivatives auristatin PHE (dolavaline-valine-dolaisoleuine-dolaproine-phenylalanine-methyl ester) (Pettit, G. R. et al., Anticancer Drug Des. 13(4):243-277, 1998; Woyke, T. et al., Antimicrob. Agents Chemother. 45(12):3580-3584, 2001), and aurastatin E and the like. Other chemotherapeutic agents are known to those skilled in the art.

However, it should be appreciated that other chemotherapeutic compounds, and/or combinations of compounds (e.g., two or more compounds described herein alone or with other compounds) may be used as aspects of the invention are not limited in this respect.

Therapeutic compositions of the present invention may be administered in pharmaceutically acceptable preparations. Such preparations may contain pharmaceutically acceptable concentrations of salt, buffering agents, preservatives, compatible carriers, supplementary immune potentiating agents such as adjuvants and cytokines, and optionally other therapeutic agents.

As used herein, the term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Examples of physiologically and pharmaceutically acceptable carriers include, without being limited to, diluents, fillers, salts, buffers, stabilizers, solubilizers, and other materials which are well known in the art. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

Therapeutics according to some embodiments of the invention can be administered by any conventional route, for example injection or gradual infusion over time. The administration may, for example, be oral, intravenous, intratumoral, intraperitoneal, intramuscular, intracavity, subcutaneous, or transdermal, or by pulmonary aerosol.

The compositions of some embodiments of the invention are administered in effective amounts. An "effective amount" is that amount of a composition that alone, or together with further doses, produces the desired clinical response. In some cases of treating a particular disease or condition, for example, a cancer manifested in a tumor, the desired response is inhibiting the progression of the disease, for example, the growth of the tumor or the spread of a primary tumor to secondary sites via metastasis. This may involve slowing the progression of the disease temporarily, although more preferably, it involves halting the progression of the disease permanently. In some cases, the desired response to treatment is a permanent eradication of tumor cells. In some cases, the desired response to treatment can be delaying or preventing the manifestation of clinical symptoms, for example, of recurrent tumors.

The effect of treatment can be monitored by routine methods or can be monitored according to diagnostic methods of the invention discussed herein.

The effective amount of a therapeutic compound or a combination of such compounds will depend, of course, on the particular tumor being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

In some embodiments, a kit is provided, comprising reagents useful for determining an expression level and/or the presence of a mutation of interest. A reagent useful for determining an expression level of a gene may, in some embodiments, be a detectable agent that binds to an expression product of the gene. Detectable agents, their generation and/or purification and their use are well known to those of skill in the art and non-limiting, exemplary detection agents include detectable binding agents, for example antibodies, antibody fragments, nucleic acids complementary to a sequence comprised in a transcript of the informative gene, aptamers, and adnectins. In some embodiments, a kit may comprise a plurality of different nucleic acid molecules that correspond to different informative gene transcripts. In some embodiments, the plurality of nucleic acid molecules is attached to a solid support. In some embodiments, a kit is provided that includes a focused microarray for the detection of informative expression levels or mutations as described herein, for example, an FBW7 expression level or an Mcl1 exression level, a deletion, totally or partially, of an FBW7 coding sequence, or of an FBW7 promoter sequence, a deletion or alteration of an FBW7 splice site (a splice site mutation) leading to aberrant splicing of the FBW7 transcript, a partial or complete deletion of the FBW7 gene, a partial or complete deletion of the FBW7 coding region, a nonsense mutation, a missense mutation, a frameshift mutation, a mutation causing a truncation of the FBW7 protein, or a splice site mutation, or a point mutation resulting in an amino acid substitution. Amino acid substitutions associated with FBW deficiency, as provided by aspects of this invention, are well known to those of skill in the art, and include, for example, a G423 mutation, a R456 mutation, mutation, a R479 mutation, a R479 mutation, a R505 mutation, a D527 mutation, or a S668 mutation, for example, a G423V mutation, a R456c mutation, a R456H mutation, a R479L mutation, a R479Q mutation, a R505c mutation, a D527G mutation, an Exon 8 splice site mutation, or a S668 frameshift mutation. In some embodiments, a plurality of primer pairs is provided for determining an expression level and/or one or more mutations of interest.

These and other aspects of the invention are illustrated by the following non-limiting examples.

EXAMPLES

Example 1

The effective use of targeted therapy is highly dependent upon the identification of responder patient populations. Loss of the Fbw7 tumor suppressor is frequently found in various types of human cancers including breast cancer, colon cancer[1] and T-cell acute lymphoblastic leukemia (T-ALL)[2]. In line with these genomic data, engineered deletion of Fbw7 in mouse T cells results in T-ALL[3-5], validating Fbw7 as a T-ALL tumor suppressor. The precise molecular mechanisms by which Fbw7 exerts anti-tumor activity remain areas of intensive investigation and are thought to relate in part to Fbw7-mediated destruction of key cancer relevant proteins including c-Jun[6], c-Myc[7], Cyclin E[8] and Notch-1[9], all of which possess oncogenic activity and are overexpressed in various human cancers including leukemia. Besides accelerating cell growth[10], overexpression of either c-Jun, c-Myc or Notch-1 can also provoke programmed cell death[11]. Thus, considerable uncertainty surrounded how Fbw7-deficient cells evade cell death in the setting of upregulated c-Jun, c-Myc and/or Notch-1. Here it is shown that $SCF^{Fbw7}$ governs cellular apoptosis by targeting the pro-survival Bcl-2 family member, Mcl-1, for ubiquitination and destruction in a GSK3 phosphorylation-dependent manner. Human T-ALL cell lines showed a close relationship between Fbw7 loss and Mcl-1 overexpression. Correspondingly, T-ALL cell lines with defective Fbw7 are particularly sensitive to the multi-kinase inhibitor, sorafenib, but resistant to the Bcl-2 antagonist, ABT-737. On the genetic level, Fbw7 reconstitution or Mcl-1 depletion restores ABT-737 sensitivity, establishing Mcl-1 as a therapeutically relevant bypass survival mechanism for Fbw7-deficient cells to evade apoptosis. Therefore, this work provides novel molecular insight into Fbw7-direct tumor suppression with direct implications for the targeted treatment of Fbw7-deficient T-ALL patients.

Mcl-1 is frequently overexpressed in various leukemias via mechanisms that are not fully understood[12]. Mcl-1 is distinct from other Bcl-2 family members in its extremely unstable nature[13], which provides a mechanism for cells to switch into either survival or apoptotic mode in response to various stresses[14]. While GSK3 phosphorylation regulates Mcl-1 stability[13], little is known about the identity of the E3 ubiquitin ligase that targets phosphorylated Mcl-1 for destruction.

Upon examination of the GSK3 sites on Mcl-1, it was surmised that they resemble a possible degron sequence that can be recognized by Fbw7 (FIG. 1a), prompting a test for the possibility that GSK3 phosphorylation of Mcl-1 triggers its degradation by Fbw7. FIG. 1 illustrates that Mcl-1 stability is controlled by Fbw7. FIG. 1a shows a sequence alignment of Mcl-1 with the c-Jun, c-Myc and Cyclin E Fbw7 phosphodegrons. The putative Fbw7 phosphodegron sequence present in Mcl-1 is conserved across different species. FIG. 1b-c shows immunoblot analysis of HeLa cells transfected with the indicated siRNA oligonucleotides. FIG. 1d shows immunoblot analysis of thymus cells derived from control mice or Fbw7 conditional knockout (Lck-Cre/Fbw7$^{fl/fl}$) mice. Mcl-1 band intensity was normalized to Hsp90, then normalized to the control lane. Data was shown as mean±SEM from three independent experiments. FIG. 1e displays immunoblot analysis of wild-type (WT) or Fbw7−/− DLD1 cells after synchronization with nocodazole and release at the indicated time points. FIG. 1f shows immunoblot analysis of the indicated human T-ALL cell lines. FIG. 1g shows DND41 and Loucy cells, which contain wild-type Fbw7, were infected with the indicated lentiviral shRNA constructs and selected with 1 µg/ml puromycin to eliminate the non-infected cells. Cell lysates were collected for immunoblot analysis with the indicated antibodies. FIG. 1h shows T-ALL cell lines with deficient Fbw7 that were infected with Fbw7-expressing retrovirus construct (with empty vector as a negative control), and selected with 1 µg/ml puromycin to eliminate the non-infected cells. Cell lysates were collected for immunoblot analysis with the indicated antibodies. FIG. 1i shows immunoblot analysis of the indicated primary human T-ALL clinical samples. FIG. 1j shows immunoblot analysis of the indicated murine T-ALL cell lines derived from the FBW7 Terc$^{−/−}$Atm$^{−/−}$p53$^{−/−}$ (TKO) mice. FIG. 1k-m shows in vivo effects of Mcl-1 depletion in Fbw7-deficient T-ALL cells. An in vivo model of Fbw7-deficient T-ALL was created by orthotopic engraftment of CMLT1-luciferase cells in NOD-SCID-IL2Rγ$^{null}$ (NSG) mice (k, left; CMLT1-shGFP, right; CMLT1-shMcl-1). immunoblot analysis of the engineered CMLT1 cell lines (l). Mice were injected with 1×10$^7$ cells (n=7/group) via the lateral tail vein (m). Tumor burden was determined by quantification of total body luminescence, and are expressed as photons/second/standardized region of interest (ph/s/ROI). Data was represented as mean±SEM with statistical significance determined by Student's t-test.

Depletion of Fbw7 (FIG. 1b) or SCF components Cullin-1, Rbx1 and Skp1 (FIG. 1c), but not other F-box proteins that were examined (FIG. 1b), resulted in a significant increase in Mcl-1. T-cell lineage-specific depletion of Fbw7 in Lck-Cre/Fbw7$^{fl/fl}$ exhibited elevated Mcl-1 levels in their thymi (FIG. 1d) as well as resulting thymic lymphoma (FIG. 2a) and acute leukemia cells (FIG. 2b). Consistent with Wertz et al.[15], Fbw7−/− DLD1 (FIG. 1e) and siFbw7 treated HeLa cells (FIG. 2c) have elevated Mcl-1 expression mainly in the M and early G1 cell cycle phases. The clinical relevance of this finding is further demonstrated by the fact that T-ALL cell lines harboring Fbw7 mutations/deletions have a significant increase in Mcl-1 (FIG. 1f). Additionally, depletion of Fbw7 in DND41 or Loucy cells (with wild-type Fbw7) leads to increased Mcl-1 expression (FIG. 1g) while re-introduction of wild-type Fbw7 dramatically reduced Mcl-1 expression in Fbw7-deficient T-ALL cells (FIG. 1h), supporting a causal relationship between loss of Fbw7 activity and elevated Mcl-1 expression in the T-ALL cells examined. More importantly, elevated Mcl-1 expression is also observed in both primary human and murine T-ALL samples with deficient Fbw7 activity (FIG. 1i, FIG. 1j and FIG. 2a-b[3,4]), and depletion of Mcl-1 impaired T-ALL disease progression in vivo (FIG. 1k-m).

Figure 2:
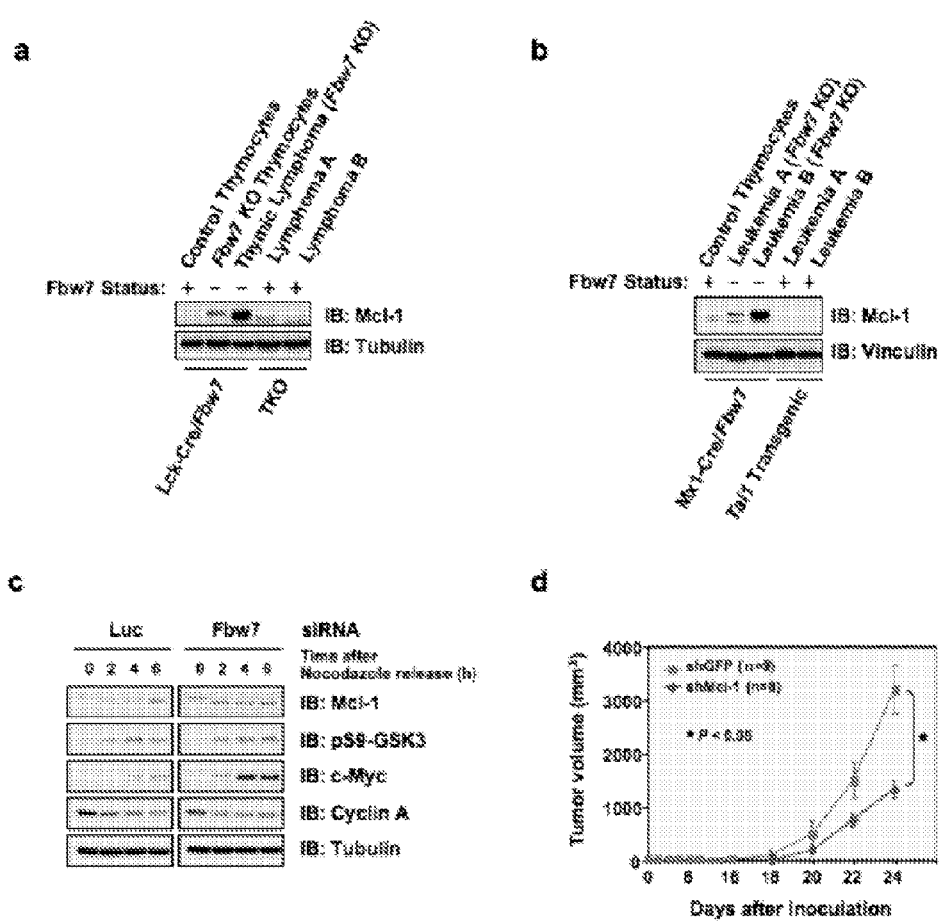
FIG. 2 shows that depletion of Fbw7 results in elevated Mcl-1 abundance.

FIG. 2 shows that depletion of Fbw7 results in elevated Mcl-1 abundance. FIG. 2a shows total thymocytes from 8-wk-old Lck-Cre/Fbw7$^{+/fl}$ (Control) or Lck-Cre/Fbw7$^{fl/fl}$ (Fbw7 KO) mice that were subjected to immunoblot analysis with the indicated antibodies. Thymic lymphoma cells were from a 15-wk-old Lck-Cre/Fbxw7$^{fl/fl}$ (Fbw7 KO) and Terc$^{−/−}$ATM$^{−/−}$p53$^{−/−}$ (TKO) mice. FIG. 2b shows total thymocytes from 12-wk-old Mx1-Cre/Fbw7$^{fl/fl}$ (Control), leukemic Fbw7 KO or Tall transgenic mice that were subjected to immunoblot analysis with the indicated antibodies. FIG. 2c shows immunoblot analysis of HeLa cells transfected with the indicated siRNA oligos after synchronization with nocodazole and release. FIG. 2d shows in vivo effects of Mcl-1 depletion in Fbw7-deficient T-ALL cells. An in vivo xenograft model of Fbw7-deficient T-ALL was created by subcutaneous injection of 1.2×10$^7$ CMLT1 cells (CMLT1-shGFP or CMLT1-shMcl-1) in SCID mice. Tumor burden was determined by measuring the diameters of the tumor size. The tumor volume was calculated by using the formula, 1/2×(tumor length)×(tumor width)$^2$. Data was represented as the mean of tumor volume (mm$^3$)±SEM with statistical significance determined by Student's t-test.

Figure 3:
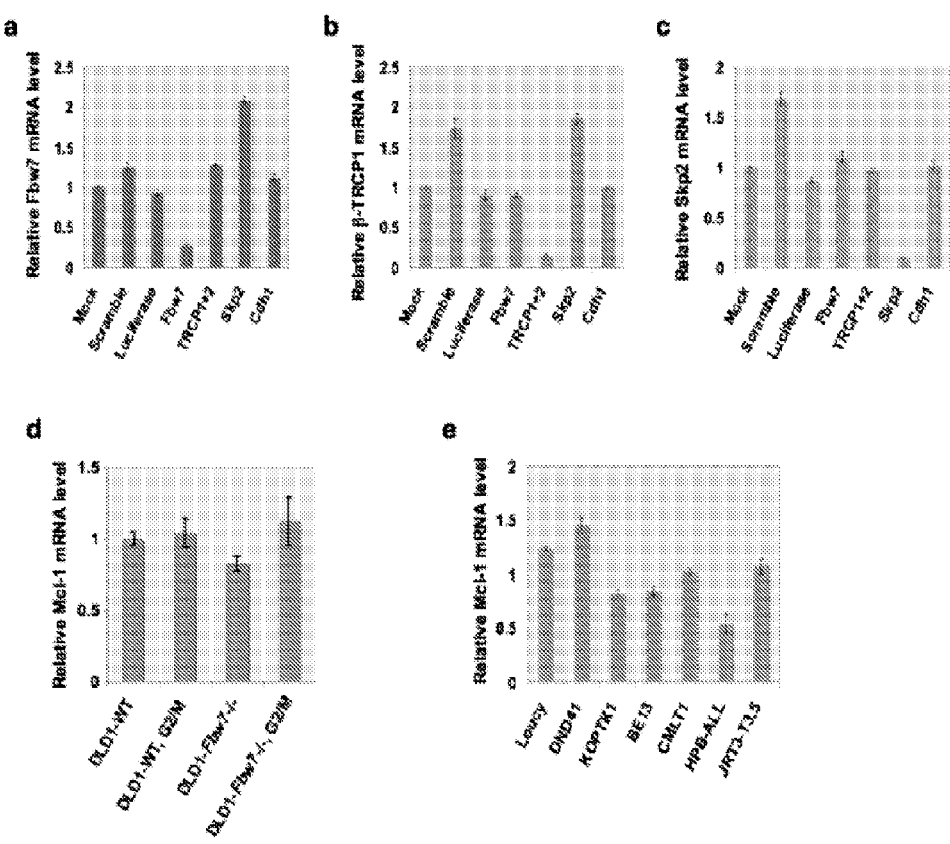
FIG. 3 shows that inactivation of Fbw7 does not affect Mcl-1 mRNA expression levels.

FIG. 3 shows that inactivation of Fbw7 does not affect Mcl-1 mRNA expression levels. FIG. 3a-c shows teal-time RT-PCR analysis to examine the depletion efficiency of the siRNA oligos against Fbw7 (a), b-TRCP1 (b) and Skp2 (c) used in FIG. 1b. Three independent sets of experiments were performed to generate the error bars. The error bars represent one standard deviation. FIG. 3d shows real-time RT-PCR analysis to examine the relative Mcl-1 mRNA expression levels in wild-type (WT) and Fbw7−/− DLD1 cells. Three independent sets of experiments were performed to generate the error bars. The error bars represent one standard deviation. FIG. 3e shows real-time RT-PCR analysis to examine the relative Mcl-1 mRNA expression levels in various T-ALL cell lines. Three independent sets of experiments were performed to generate the error bars. The error bars represent one standard deviation.

Consistent with a post-translational mode of regulation, no changes in Mcl-1 mRNA levels were observed after depletion of Fbw7 in DLD1 cells (FIG. 3d), and no positive relationship was observed between Mcl-1 mRNA levels and loss of Fbw7 in T-ALL cells (FIG. 3e). The half-life of Mcl-1 was significantly extended in the thymi of Fbw7−/− mice and Fbw7-deficient human T-ALL cells (FIG. 4a-c) and experimental manipulation of Fbw7 levels changed Mcl-1 stability accordingly (FIG. 4d-e). Together, these results suggest that Mcl-1 is a downstream ubiquitination target for SCF$^{Fbw7}$.

Figure 4:
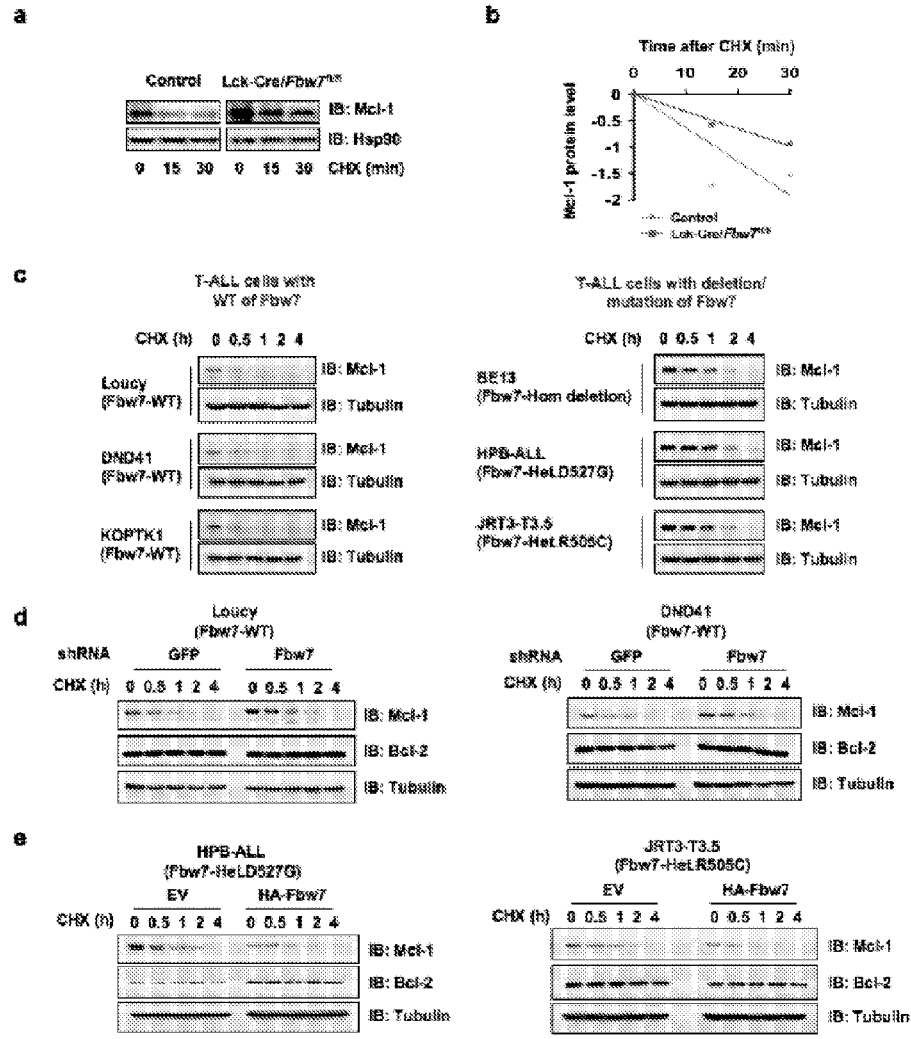
FIG. 4 shows that Mcl-1 half-life is controlled by Fbw7.

FIG. 4 shows that Mcl-1 half-life is controlled by Fbw7. FIG. 4a-b shows thymocytes from 8-wk-old Lck-Cre/Fbw7$^{+/fl}$ (Control) or Lck-Cre/Fbw7$^{fl/fl}$ (Fbw7 KO) that were treated with 100 µg/ml cycloheximide. At the indicated time points, whole cell lysates were prepared and immunoblots were probed with the indicated antibodies (a). Band intensity was measured, normalized by that of Hsp90, and expressed as a percentage of the corresponding normalized value for time zero (b). FIG. 4c shows the indicated T-ALL cell lines treated with 20 µg/ml cycloheximide. At the indicated time points, whole cell lysates were prepared and immunoblots were probed with the indicated antibodies. FIG. 4d shows DND41 and Loucy cells, which contain wild-type Fbw7, and which were infected with the indicated lentiviral shRNA construct and selected with 1 µg/ml puromycin to eliminate the non-infected cells. Afterwards, the indicated cell lines were treated with 20 µg/ml cycloheximide. At the indicated time points, whole cell lysates were prepared and immunoblots were probed with the indicated antibodies. FIG. 4e shows HPB-ALL and JRT3-T3.5 cells with deficient Fbw7 that were infected with the Fbw7-expressing retrovirus construct (or an empty vector as a negative control) and selected with 1 µg/ml puromycin to eliminate the non-infected cells. Afterwards, the indicated cell lines were treated with 20 µg/ml cycloheximide. At the indicated time points, whole cell lysates were prepared and immunoblots were probed with the indicated antibodies.

Figure 5:
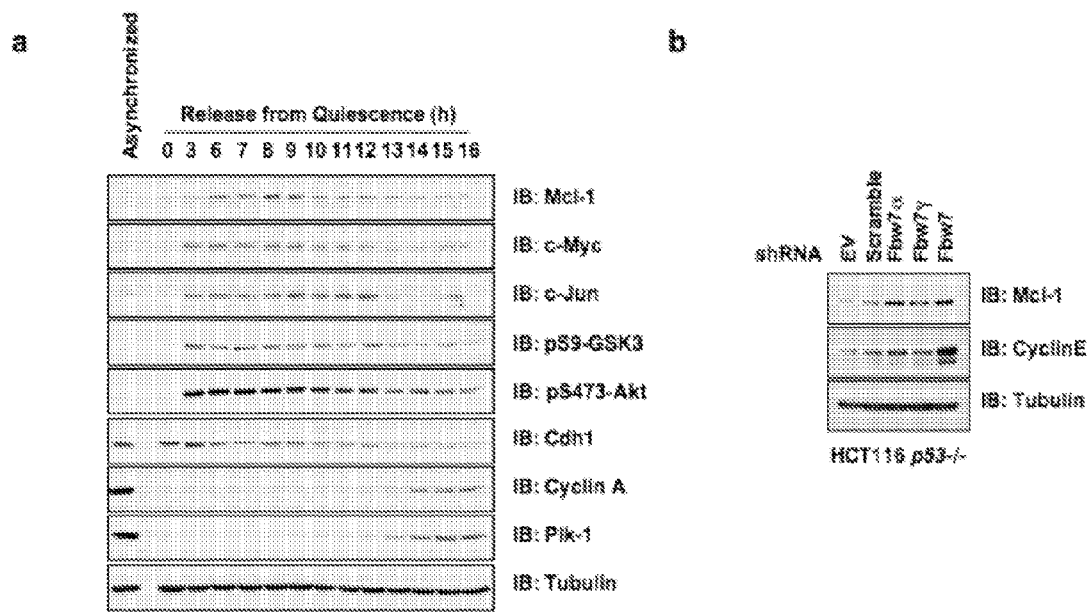
FIG. 5 shows that endogenous Mcl-1 levels inversely correlate with GSK3 activity during cell cycle progression, and Fbw7 depletion-induced Mcl-1 upregulation is p53 independent.

FIG. 5 shows that endogenous Mcl-1 levels inversely correlate with GSK3 activity during cell cycle progression, and Fbw7 depletion-induced Mcl-1 upregulation is p53 independent. FIG. 5a shows immunoblot analysis of T98G cells induced to enter the G0 phase by serum starvation for 72 hours and then released for the indicated time periods. FIG. 5b shows immunoblot analysis of HCT116 p53−/− cells transfected with the indicated shRNA constructs.

As proper substrate phosphorylation events are required for Fbw7 to recognize and target its substrates for ubiquitination[16], next it was investigated which phosphorylation events that trigger Mcl-1 destruction by Fbw7. Mass spectrometry analysis revealed that Mcl-1 is phosphorylated at multiple sites in vivo (FIG. 6a and FIG. 7a-c). In addition to Ser159 and Thr163[13,17], Ser64 and Ser121 were also phosphorylated in vivo. Consistent with previous reports[13,17] Mcl-1 destruction is promoted by GSK3 (FIG. 6b), but not ERK1/2 (FIG. 7d-f). To further investigate the significance of each individual phosphorylation site, a panel of Mcl-1 mutants was created (FIG. 6c). Using in vitro kinase assays, Ser159 and Thr163 were identified as the major GSK3 phosphorylation sites[17] and Ser121 as a minor GSK3 phosphorylation site (FIG. 6d-e and FIG. 7g). Inactivation of these GSK3 phosphorylation sites impairs the interaction between Mcl-1 and Fbw7 both in vitro (FIG. 6f and FIG. 7h) and in vivo (FIG. 6g and FIG. 7i). Furthermore, pharmacological inhibition of GSK3 activity blocked the interaction between HA-Fbw7 and endogenous Mcl-1 (FIG. 6h) and inhibited the localization of Fbw7 to the mitochondria where Mcl-1 resides (FIG. 7j-k). These results indicated that GSK3-dependent phosphorylation of Mcl-1 is necessary for its interaction with Fbw7.

Figure 6:
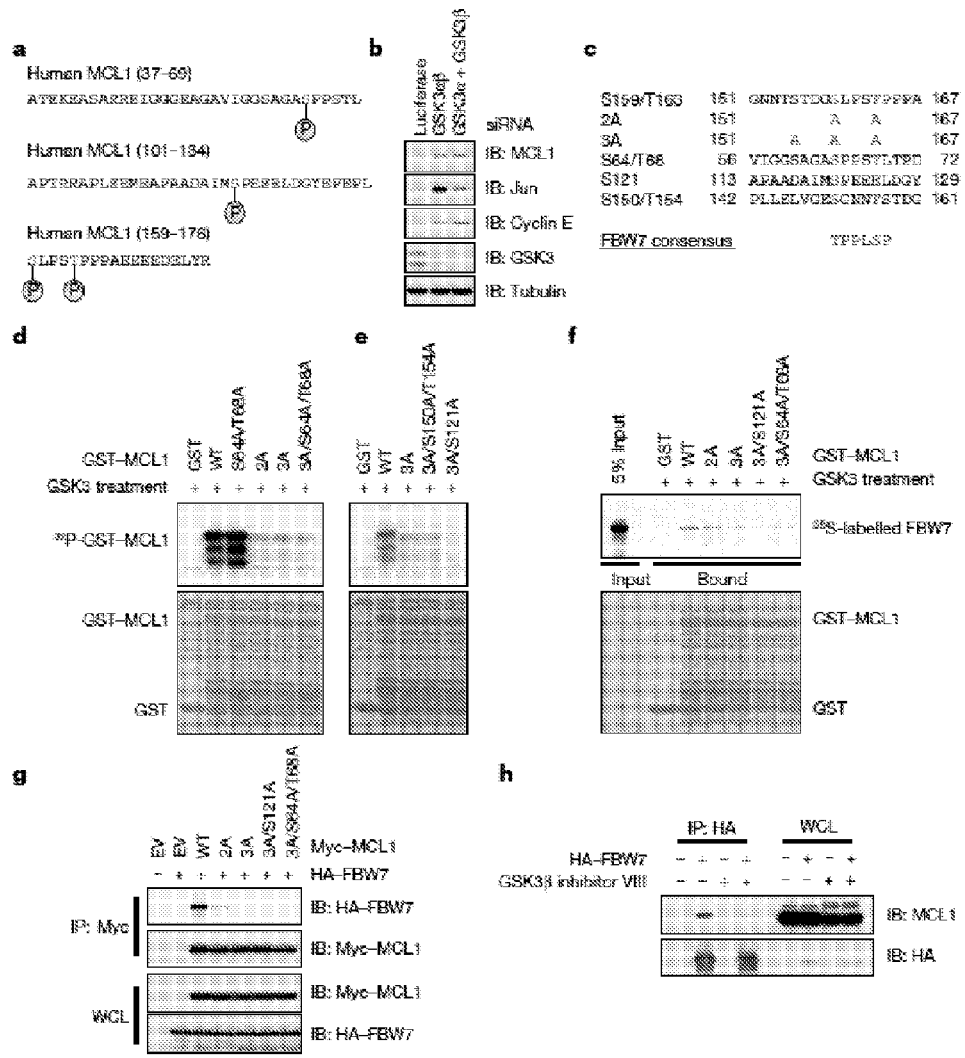
FIG. 6 shows that phosphorylation of Mcl-1 by GSK3 triggers its interaction with Fbw7. Sequences in 6a correspond, from top to bottom, to SEQ ID NOs 14-16, respectively. Sequences in 6c correspond, from top to bottom, to SEQ ID NOs 17-21, respectively.

FIG. 6 shows that phosphorylation of Mcl-1 by GSK3 triggers its interaction with Fbw7. FIG. 6a shows in vivo Mcl-1 phosphorylation sites detected by mass spectrum analysis. FIG. 6b shows Immunoblot analysis of HeLa cells transfected with the indicated siRNA oligonucleotides. FIG. 6c shows an illustration of the various Mcl-1 mutants generated for this study. FIG. 6d-e show that GSK3 phosphorylates Mcl-1 in vitro at multiple sites. Purified GSK3 protein (from New England Biolabs) was incubated with 5 µg of the indicated GST-Mcl-1 proteins in the presence of γ-$^{32}$P-ATP. The kinase reaction products were resolved by SDS-PAGE and phosphorylation was detected by autoradiography. FIG. 6f shows that phosphorylation of Mcl-1 at multiple sites by GSK3 triggers its interaction with Fbw7 in vitro. Autoradiograms showing recovery of $^{35}$S-labeled Fbw7 protein bound to the indicated GST-Mcl-1 fusion proteins (GST protein as a negative control) incubated with GSK3 prior to the pull-down assays. IN, input (5% as indicated). FIG. 6g shows immunoblot (IB) analysis of whole cell lysates (WCL) and immunoprecipitates (IP) derived from 293T cells transfected with HA-Fbw7 together with the indicated Myc-Mcl-1 constructs. Thirty hours post-transfection, cells were pretreated with 10 µM MG132 for 10 hours to block the proteasome pathway before harvesting. FIG. 6h shows immunoblot (IB) analysis of whole cell lysates (WCL) and immunoprecipitates (IP) derived from 293T cells transfected with HA-Fbw7. Thirty hours post-transfection, cells were pretreated with 20 µM MG132 for 8 hours to block the proteasome pathway before harvesting. Where indicated, 25 µM of the GSK3b inhibitor VIII (with DMSO as a negative control) was added for 8 hours before harvesting.

Figures 1, 7:
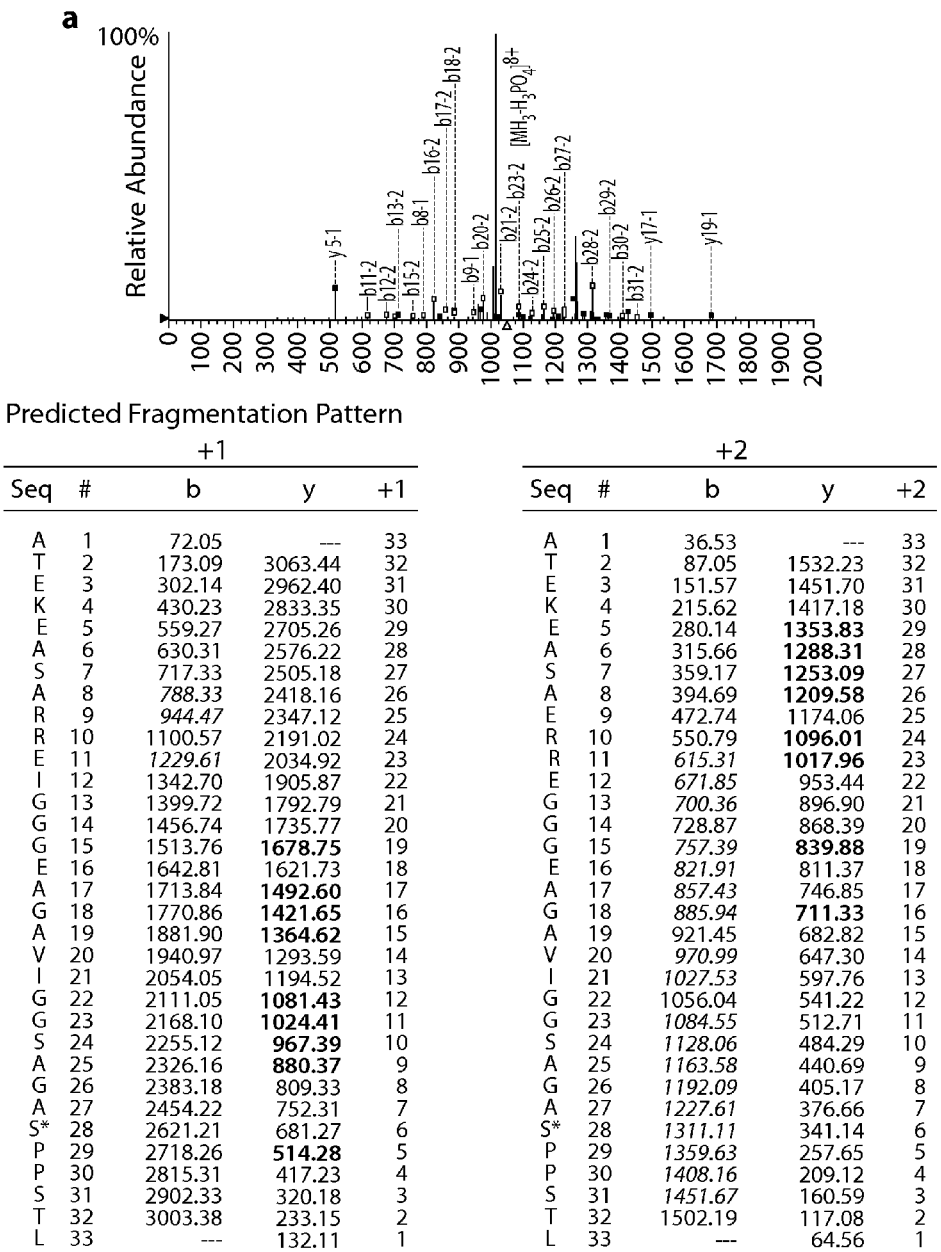
FIG. 7 shows that phosphorylation of Mcl-1 by GSK3 triggers Mcl-1/Fbw7 intereaction. Sequences in 7a, 7b, and 7c correspond to SEQ ID NOs 22-24, respectively.
Figures 2, 7:
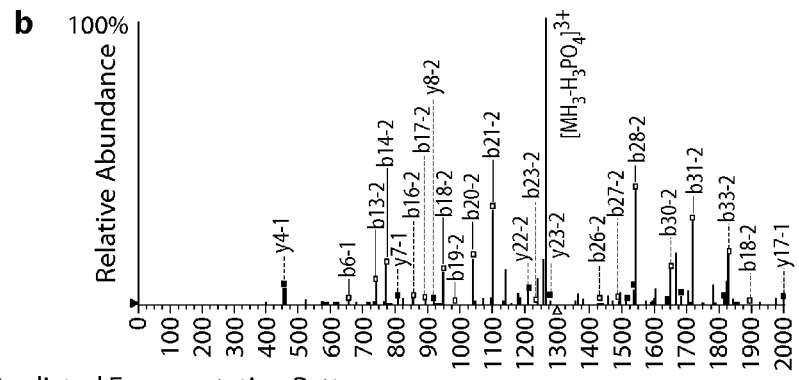
Figure 7:
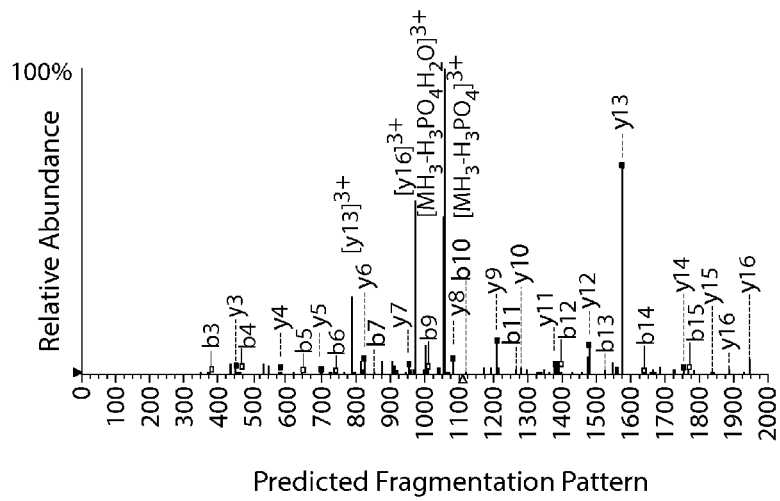
Figure 3:
Figures 4, 7:
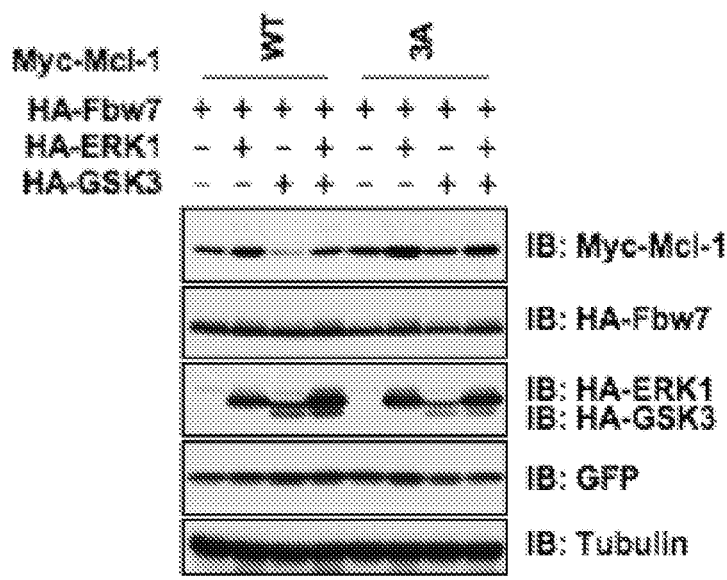
Figures 5, 7:
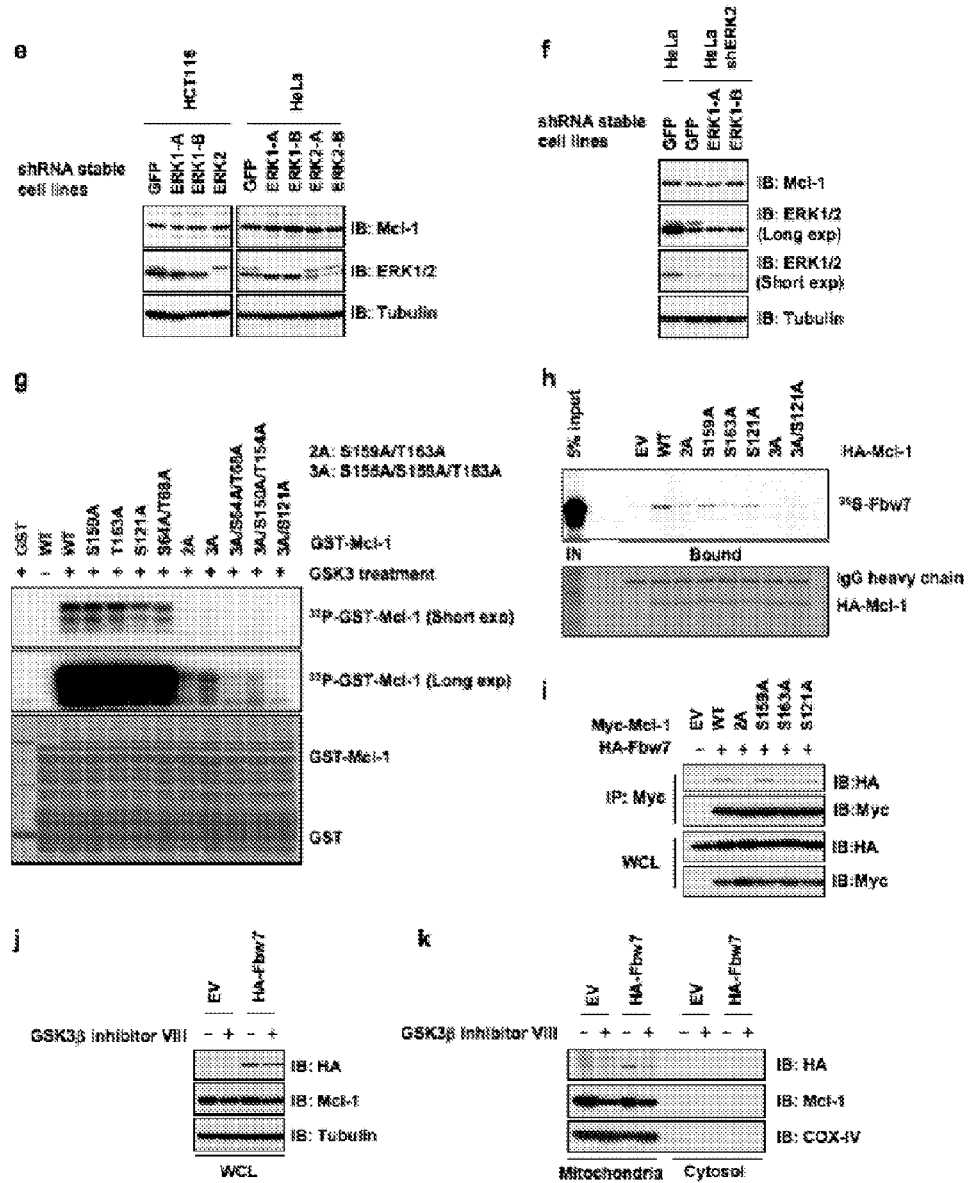

FIG. 7 demonstrates that phosphorylation of Mcl-1 by GSK3 triggers Mcl-1/Fbw7 interaction. FIG. 7a-c shows detection of in vivo Mcl-1 phosphorylation status by mass spectrum analysis. HA-Mcl-1 was transfected into 293T cells, then immunoprecipitated with anti-HA in the presence of phosphatase inhibitors. The immunoprecipitate was resolved by SDS-PAGE and phosphorylation was detected by mass spectrum analysis. The Ser64 site (a), Ser121 site (b), Ser159 and Thr163 sites (c) were detected to be phosphorylated in vivo. FIG. 7d shows immunoblot analysis of 293T cells transfected with the indicated Myc-Mcl-1 and HA-Fbw7 plasmids in the presence or absence of HA-GSK3 and/or HA-ERK1. A plasmid encoding GFP was used as a negative control for transfection efficiency. FIG. 7e-f shows results from HeLa or HCT116 cells that were infected with the indicated lentiviral shRNA constructs (with shGFP as a negative control) and selected with 1 µg/ml puromycin to eliminate the non-infected cells. Whole cell lystates were collected for immunoblot analysis. FIG. 7g shows that GSK3 phosphorylates Mcl-1 in vitro at multiple sites. Purified GSK3 protein (from New England Biolabs) was incubated with 5 µg of the indicated GST-Mcl-1 proteins in the presence of γ-$^{32}$P-ATP. The kinase reaction products were resolved by SDS-PAGE and phosphorylation was detected by autoradiography. FIG. 7h shows that phosphorylation of Mcl-1 at multiple sites in vivo by GSK3 triggers its interaction with Fbw7 in vitro. Autoradiograms showing recovery of $^{35}$S-labeled Fbw7 protein bound to the indicated HA-Mcl-1 proteins immunoprecipitated from 293T cells. IN, input (5% as indicated). FIG. 7i shows immunoblot (IB) analysis of whole cell lysates (WCL) and immunoprecipitates (IP) derived from 293T cells transfected with HA-Fbw7 together with the indicated Myc-Mcl-1 constructs. Thirty hours post-transfection, cells were pretreated with 10 µM MG132 for 10 hours to block the proteasome pathway before harvesting. FIG. 7j-k shows results from HeLa cells that were transfected with the pcDNA3-HA-Fbw7 construct (with empty vector as a negative control) and selected with 800 mg/ml G418 to generate a cell line stably expressing HA-Fbw7. Cells were pretreated with 20 µM MG132 for 8 hours to block the proteasome pathway before harvesting. Where indicated, 25 µM of the GSK3b inhibitor VIII (with DMSO as a negative control) was added for 8 hours before harvesting for immunoblot analysis (j). Under the same experimental conditions, another set of cells were collected and mitochondrial and cytosolic fractions were separated by ultracentrifuge before immunoblot analysis with the indicated antibodies (k).

Consistent with this Fbw7-Mcl-1 regulatory axis, Mcl-1 specifically interacts with Fbw7 (FIG. 8a-b and 8j-l) and Cullin-1 (FIG. 8c-d) and depletion of endogenous Cullin-1 increases Mcl-1 abundance (FIG. 15a).

Figures 1, 8:
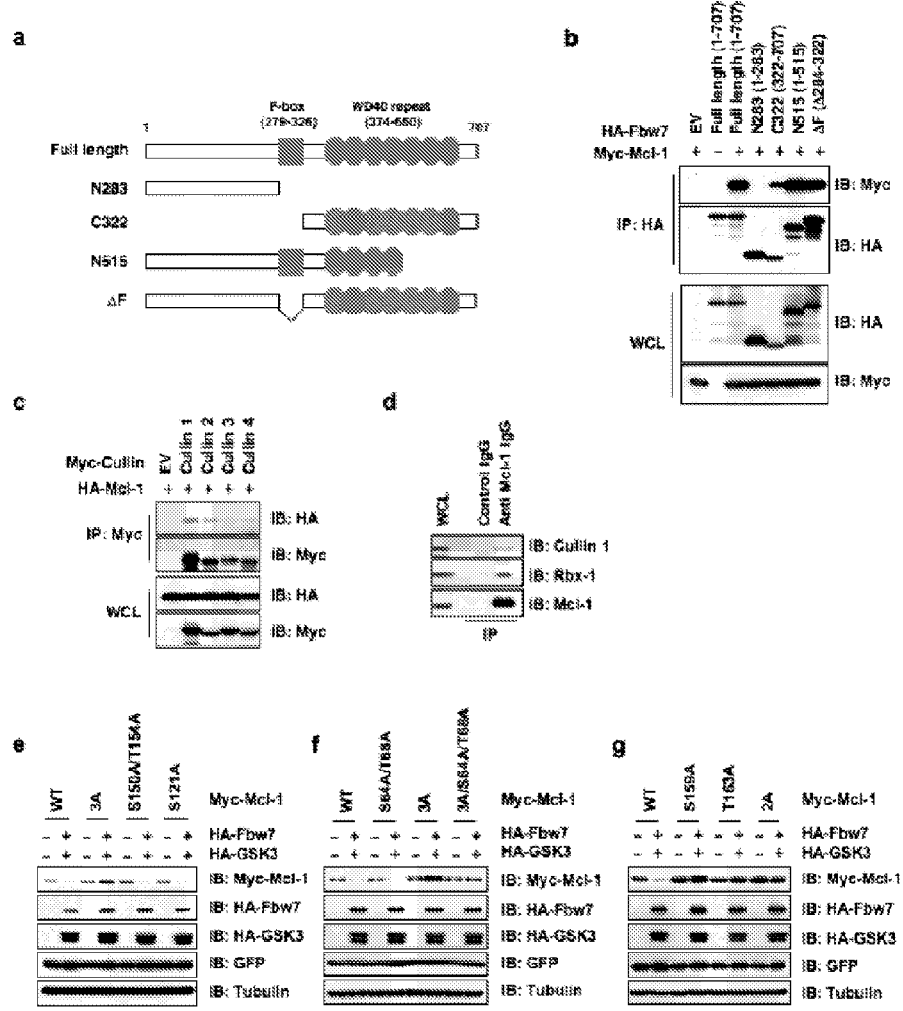
FIG. 8 shows that Mcl-1 interacts specifically with Cullin 1 and Fbw7 in vivo.

FIG. 8 shows that Mcl-1 interacts specifically with Cullin 1 and Fbw7 in vivo. FIG. 8a shows an illustration of the various Fbw7 deletion constructs used in b. FIG. 8b shows immunoblot (IB) analysis of whole cell lysates (WCL) and immunoprecipitates (IP) derived from 293T cells transfected with Myc-Mcl-1 and various HA-tagged Fbw7 constructs. Twenty hours post-transfection, cells were treated with 10 µM MG132 overnight before harvesting. FIG. 8c shows immunoblot (IB) analysis of whole cell lysates (WCL) and immunoprecipitates (IP) derived from 293T cells transfected with HA-Mcl-1 and various Myc-tagged Cullin constructs. Twenty hours post-transfection, cells were treated with 10 µM MG132 overnight before harvesting. FIG. 8d shows immunoblot (IB) analysis of HEK-293 cell whole cell lysates (WCL) and anti-Mcl-1 immunoprecipitates (IP). Mouse IgG was used as a negative control for the immunoprecipation procedure. Cells were treated with 10 µM MG132 overnight before harvesting. FIG. 8e-g shows immunoblot analysis of 293T cells transfected with the indicated Myc-Mcl-1 and HA-Fbw7 plasmids in the presence or absence of HA-GSK3. A plasmid encoding GFP was used as a negative control for transfection efficiency. FIG. 8h shows immunoblot analysis of HeLa or U20S cells transfected with the indicated Myc-Mcl-1 and HA-Fbw7 plasmids in the presence or absence of HA-GSK3. A plasmid encoding GFP was used as a negative control for transfection efficiency. FIG. 8i shows immunoblot (IB) analysis of whole cell lysates (WCL) and immunoprecipitates (IP) derived from HeLa cells transfected with HA-tagged Fbw7 and the indicated Myc-Mcl-1 constructs. Twenty hours post-transfection, cells were treated with 330 nM Nocodazole for 18 hours to arrest cells in the M phase and 25 µM MG132 for 8 hours before harvesting. FIG. 8j shows immunoblot (IB) analysis of whole cell lysates (WCL) and immunoprecipitates (IP) derived from 293T cells transfected with Myc-Mcl-1 and the indicated HA-tagged F-box protein constructs (or HA-Cdh1 as a negative control). Twenty hours post-transfection, cells were treated with 330 nM Nocodazole for 18 hours to arrest cells in the M phase and 25 µM MG132 for 8 hours before harvesting. FIG. 8k shows an illustration of the various Mcl-1 deletion constructs used in 1. FIG. 8l shows immunoblot (IB) analysis of whole cell lysates (WCL) and immunoprecipitates (IP) derived from 293T cells transfected with HA-Fbw7 and various Myc-Mcl-1 constructs. Twenty hours post-transfection, cells were treated with 10 µM MG132 overnight before harvesting. IP analyses were performed to demonstrate the role of the individual BH domains and the transmembrane domain in mediating Mcl-1/Fbw7 interaction. Deletion of the BH3 or BH4 domains was found to have no effect on Mcl-1/Fbw7 interaction, and deletion of the BH1 or BH2 domains only moderately decreased Mcl-1/Fbw7 interaction. On the other hand, deletion of the transmembrane domain has a more dramatic effect on Mcl-1/Fbw7 interaction.

Next, the mechanism by which Fbw7 alters Mcl-1 stability was explored. Overexpression of Fbw7 and GSK3 significantly decreased Mcl-1 abundance (FIG. 9a and FIG. 8h), while inactivation of the major GSK3 phosphorylation sites impaired Fbw7-mediated destruction (FIG. 9b and FIG. 8e-g). All Fbw7 isoforms (particularly a and g) participate in Mcl-1 stability control and Fbw7 dimerization is not required to degrade Mcl-1 (FIG. 10a-e). Mutant Fbw7 constructs derived from T-ALL patients displayed reduced ability to interact with Mcl-1 (FIG. 8i), and were therefore unable to degrade Mcl-1 (FIG. 9c). Moreover, Fbw7/GSK3-mediated Mcl-1 destruction was blocked by MG132, indicating the involvement of the ubiquitin/proteasome pathway in this process (FIG. 9a). In support of this idea, co-expression of GSK3 and Fbw7 resulted in a marked reduction in the half-life of wild-type Mcl-1, but not the 2A or 3A Mcl-1 mutants (FIG. 9d) with reduced interaction with Fbw7 (FIG. 6g). Furthermore, loss of Fbw7 extends the half-life of endogenous Mcl-1 (FIG. 9e), and Fbw7 promotes Mcl-1 ubiquitination in a GSK3-dependent manner (FIG. 9f and FIG. 11a-b and 11e). The decrease of Mcl-1 expression is also impaired in response to various DNA-damaging agents[18] in Fbw7−/− DLD1 cells (FIG. 9g and FIG. 11f). These data together suggested a physiological role for Fbw7 in promoting Mcl-1 destruction in vivo in a GSK3 phosphorylation-dependent manner.

Figure 9:
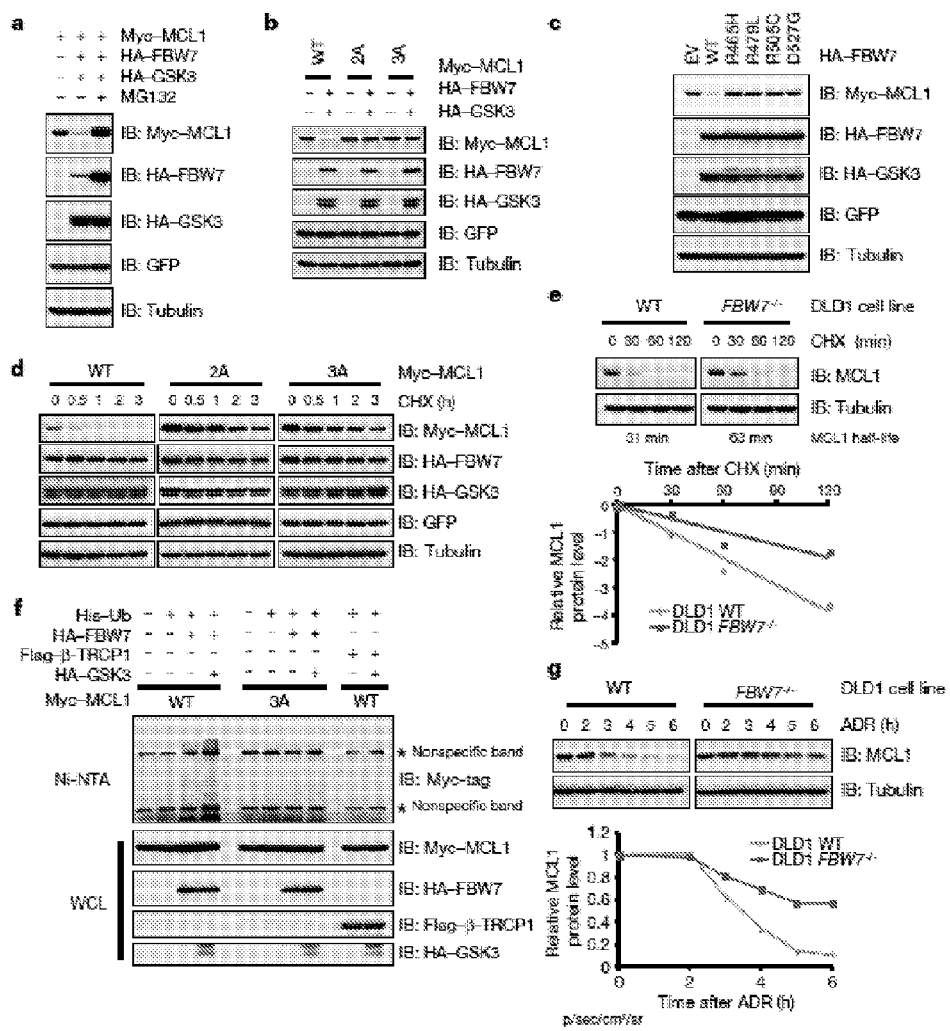
FIG. 9 shows that Fbw7 promotes Mcl-1 ubiquitination and destruction in a GSK3 phosphorylation-dependent manner.

FIG. 9 shows that Fbw7 promotes Mcl-1 ubiquitination and destruction in a GSK3 phosphorylation-dependent manner. FIG. 9a-c shows GSK3 phosphorylation-dependent degradation of Mcl-1 by Fbw7. Immunoblot analysis of 293T cells transfected with the indicated Myc-Mcl-1 and HA-Fbw7 plasmids in the presence or absence of HA-GSK3. A plasmid encoding GFP was used as a negative control for transfection efficiency. Where indicated, the proteasome inhibitor MG132 was added. FIG. 9d shows results from 293T cells that were transfected with the indicated Myc-Mcl-1 constructs together with the HA-Fbw7 and HA-GSK3 plasmids. Twenty hours post-transfection, cells were split into 60 mm dishes, and after another 20 hours, treated with 20 µg/ml cycloheximide (CHX). At the indicated time points, whole cell lysates were prepared and immunoblots were probed with the indicated antibodies. FIG. 9e shows results from wild-type (WT) or Fbw7−/− DLD1 cells that were treated with 20 µg/ml cycloheximide (CHX). At the indicated time points, whole cell lysates were prepared and immunoblots were probed with the indicated antibodies. Mcl-1 band intensity was normalized to tubulin, then normalized to the t=0 controls. FIG. 9f shows immunoblot analysis (IB) of whole cell lysates (WCL) and His-tag pull-down of HeLa cells transfected with the indicated plasmids. Twenty hours post-transfection, cells were treated with the proteasome inhibitor MG132 overnight before harvesting. His-tag pull-down was performed in the presence of 8 M urea to eliminate any possible contamination from Mcl-1-associated proteins. FIG. 9g shows immunoblot analysis of wild-type (WT) or Fbw7−/− DLD1 cells treated with 101.1M adriamycin (ADR) for the indicated durations of time. Mcl-1 band intensity was normalized to tubulin, then normalized to the t=0 controls.

Figure 10:
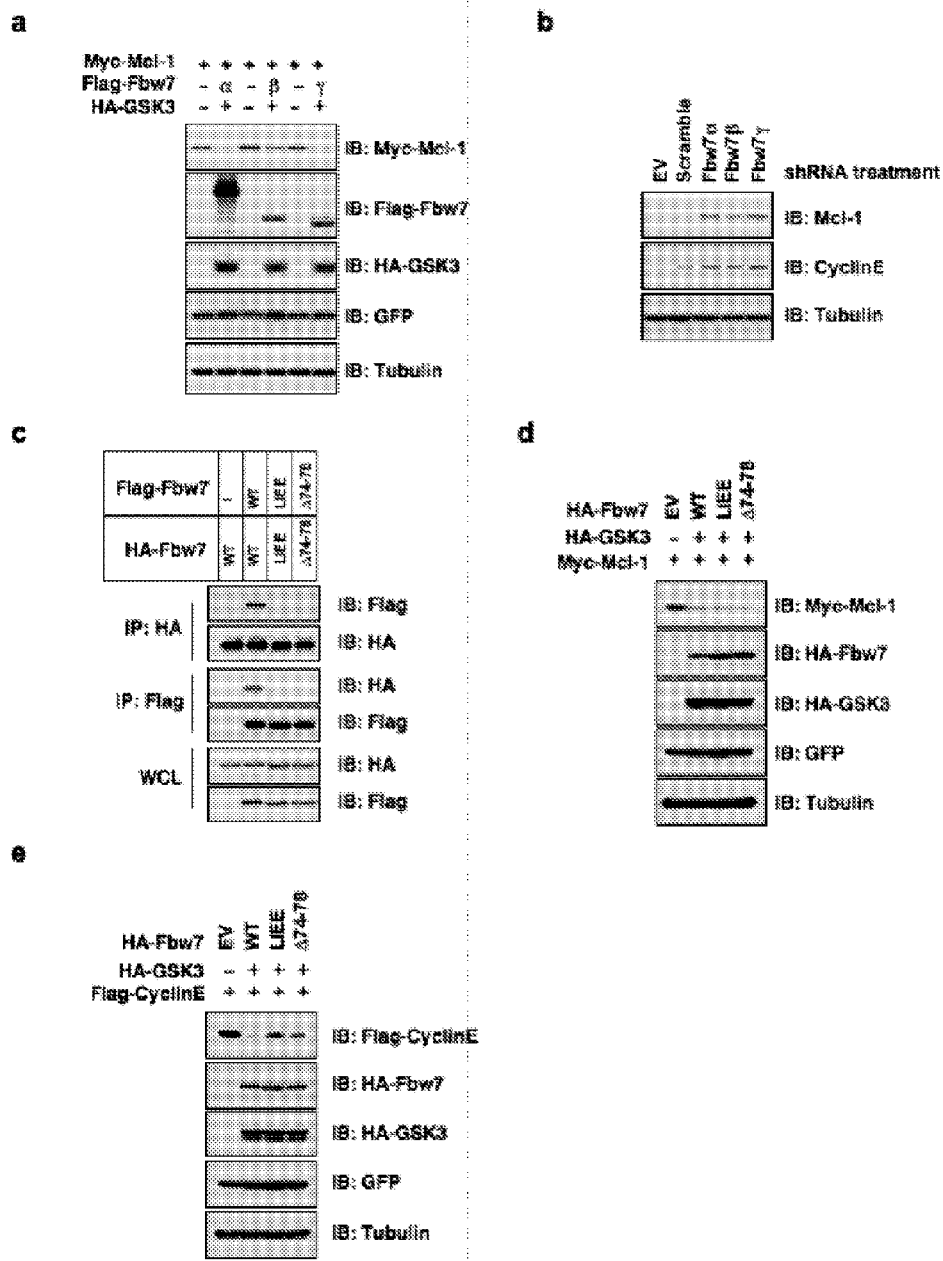
FIG. 10 shows Fbw7 isoform specificity and dimerization requirement for its ability to promote Mcl-1 destruction.

FIG. 10 illustrates Fbw7 isoform specificity and dimerization requirement for its ability to promote Mcl-1 destruction. FIG. 10a shows immunoblot analysis of 293T cells transfected with the indicated Myc-Mcl-1 and Flag-Fbw7 plasmids in the presence or absence of HA-GSK3. A plasmid encoding GFP was used as a negative control for transfection efficiency. FIG. 10b shows results from HEK-293 cells that were transfected with the indicated shRNA constructs. Whole cell lysates were collected for immunoblot analysis. FIG. 10c shows immunoblot (IB) analysis of whole cell lysates (WCL) and immunoprecipitates (IP) derived from 293T cells transfected with the indicated HA-tagged and Flag-tagged Fbw7 constructs. Twenty hours post-transfection, cells were treated with 10 µM MG132 overnight before harvesting. FIG. 10d shows immunoblot analysis of 293T cells transfected with the indicated Myc-Mcl-1 and HA-Fbw7 plasmids in the presence or absence of HA-GSK3. A plasmid encoding GFP was used as a negative control for transfection efficiency. FIG. 10e shows immunoblot analysis of 293T cells transfected with the indicated Flag-Cyclin E and HA-Fbw7 plasmids in the presence or absence of HA-GSK3. A plasmid encoding GFP was used as a negative control for transfection efficiency.

Figure 11:
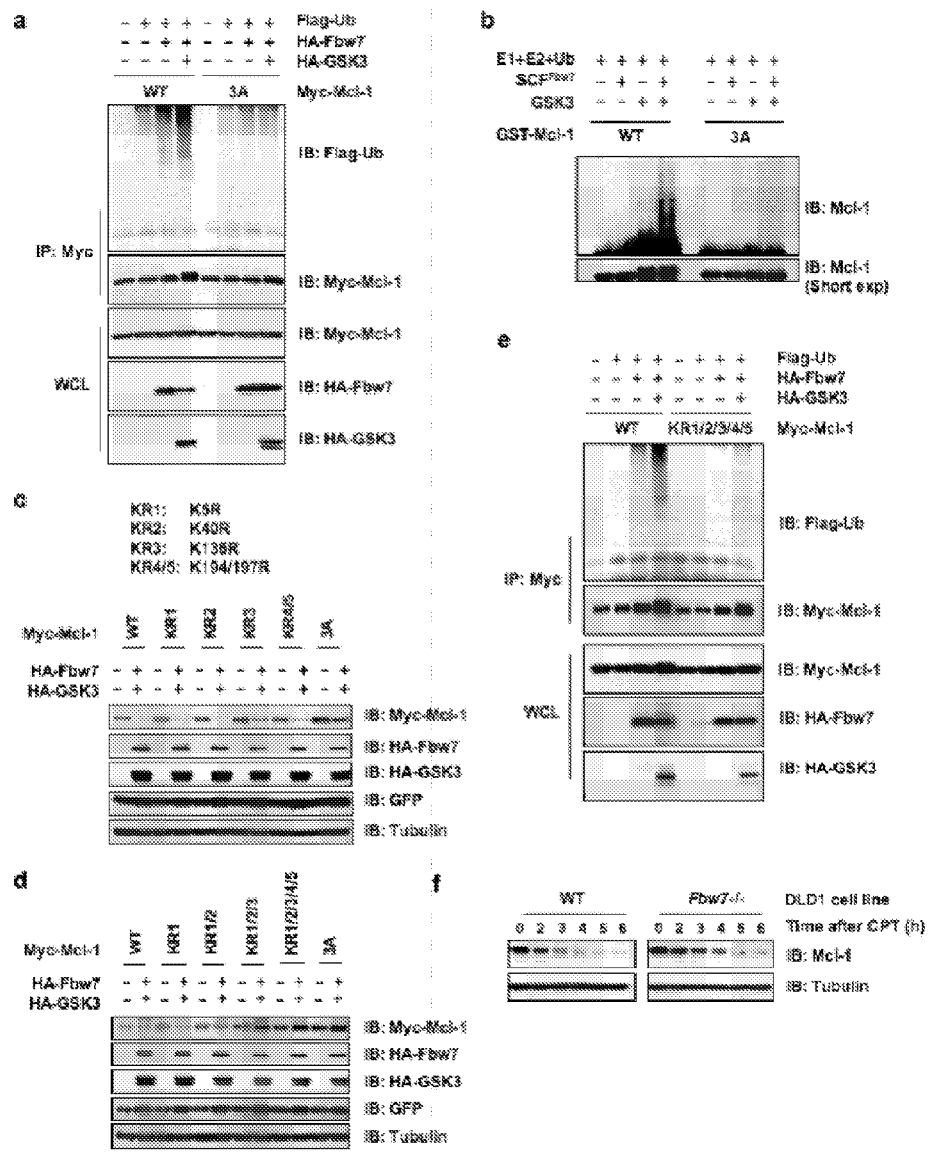
FIG. 11 shows that Fbw7 promotes Mcl-1 ubiquitination.

FIG. 11 shows that Fbw7 promotes Mcl-1 ubiquitination. FIG. 11a shows immunoblot (IB) analysis of whole cell lysates (WCL) and anti-Myc immunoprecipitates of 293T cells transfected with the indicated plasmids. Twenty hours post-transfection, cells were treated with the proteasome inhibitor MG132 overnight before harvesting. FIG. 11b shows that the SCF/Fbw7 complex promotes Mcl-1 ubiquitination in vitro. Affinity-purified SCF/Fbw7 complexes were incubated with purified recombinant GST-Mcl-1 proteins, purified E1, E2 and ubiquitin as indicated at 30° C. for 45 minutes. The ubiquitination reaction products were resolved by SDS-PAGE and probed with the anti-Mcl-1 antibody. FIG. 11c shows that inactivation of the individual putative ubiquitination sites in Mcl-1 does not impair Fbw7-mediated Mcl-1 destruction. Immunoblot analysis of 293T cells transfected with the indicated Myc-Mcl-1 and HA-Fbw7 plasmids in the presence or absence of HA-GSK3. A plasmid encoding GFP was used as a negative control for transfection efficiency. FIG. 11d illustrates that combinational inactivation of the putative ubiquitination sites in Mcl-1 leads to a progressive resistance to Fbw7-mediated Mcl-1 destruction. Immunoblot analysis of 293T cells transfected with the indicated Myc-Mcl-1 and HA-Fbw7 plasmids in the presence or absence of HA-GSK3. A plasmid encoding GFP was used as a negative control for transfection efficiency. FIG. 11e shows that inactivation of the five putative ubiquitination sites impairs the Fbw7-mediated ubiquitination of Mcl-1 in vivo. Immunoblot (IB) analysis of whole cell lysates (WCL) and anti-Myc immunoprecipitates of 293T cells transfected with the indicated plasmids. Twenty hours post-transfection, cells were treated with the proteasome inhibitor MG132 overnight before harvesting. FIG. 1 if shows immunoblot analysis of wild-type (WT) or Fbw7−/− DLD1 cells treated with 10 mM camptothecin (CPT) for the indicated durations of time.

Figure 12:
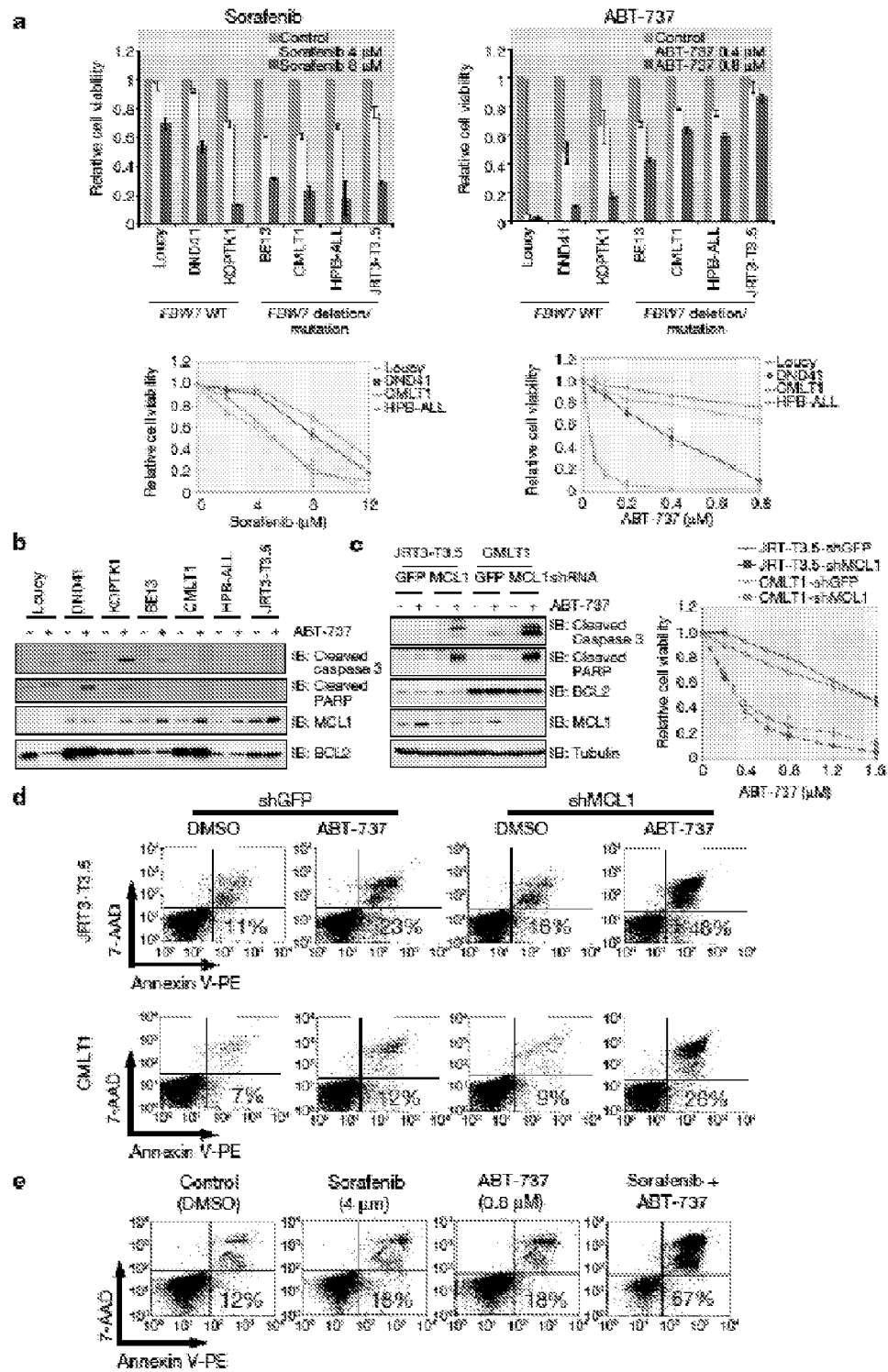
FIG. 12 shows that elevated Mcl-1 expression protects Fbw7-deficient T-ALL cell lines from ABT-737-induced apoptosis.
Figures 1, 13:
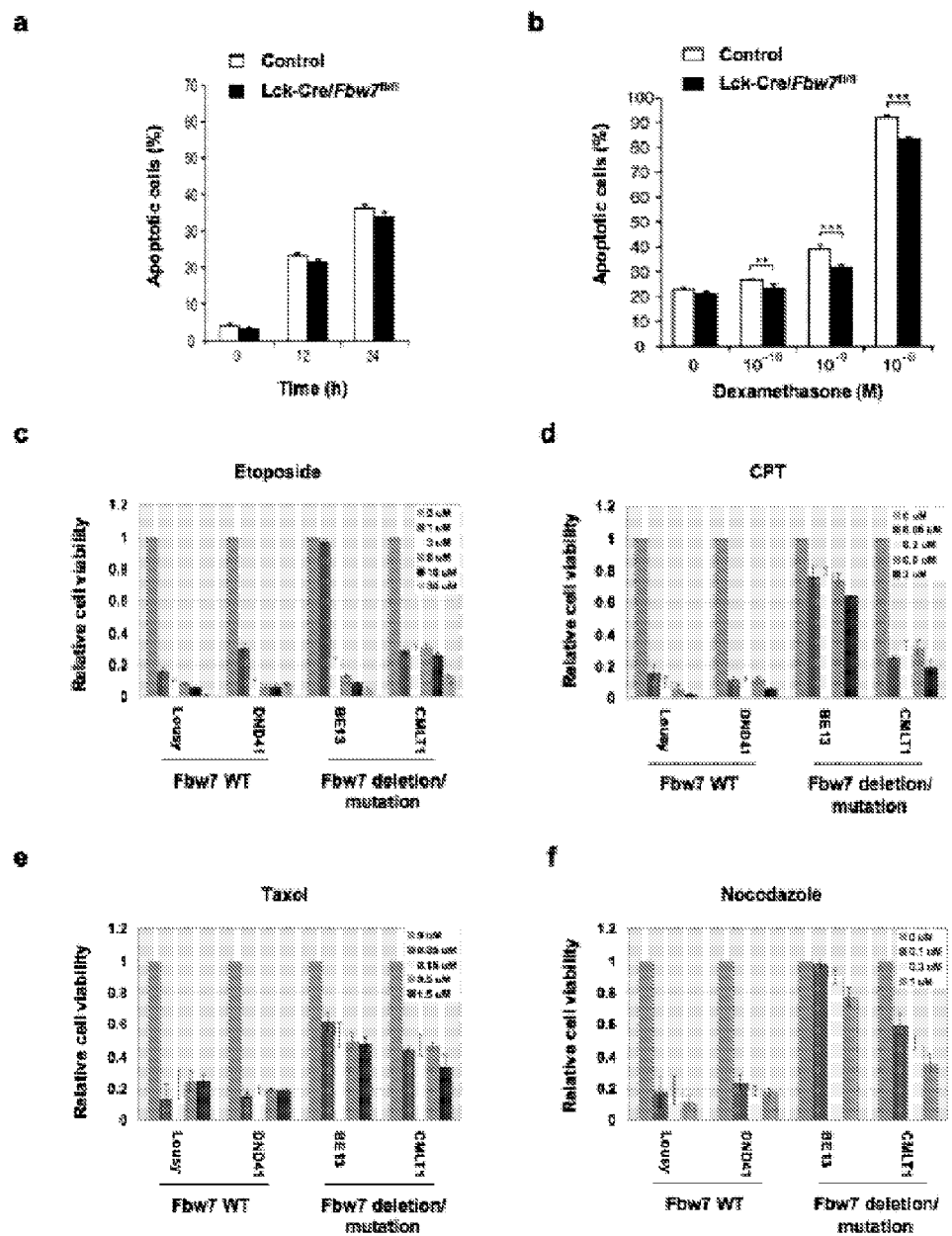
FIG. 13 shows that Fbw7-deficient T-ALL cell lines are more sensitive to sorafenib, but have increased resistance to ABT-737 treatment.
Figures 2, 13:
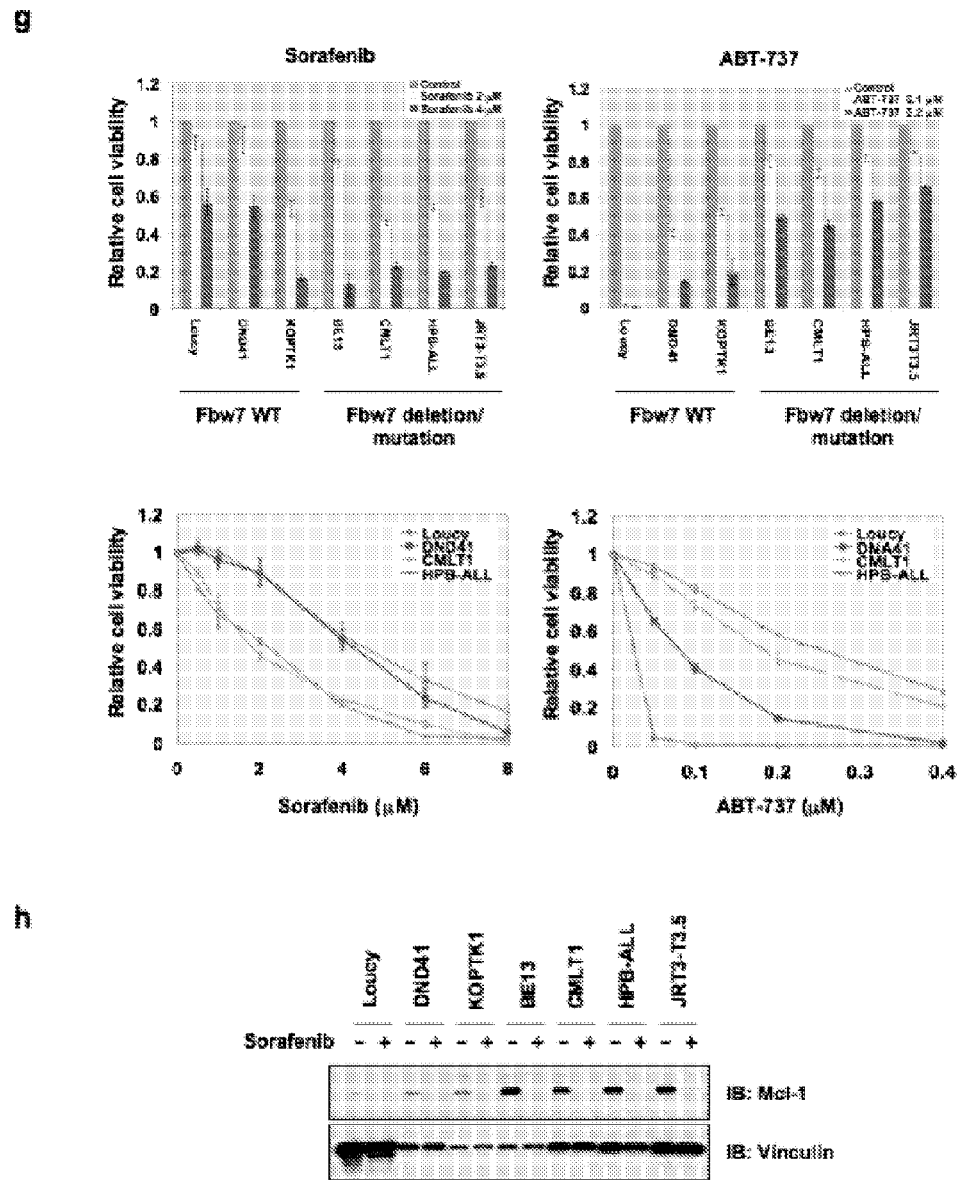
Figures 3, 13:
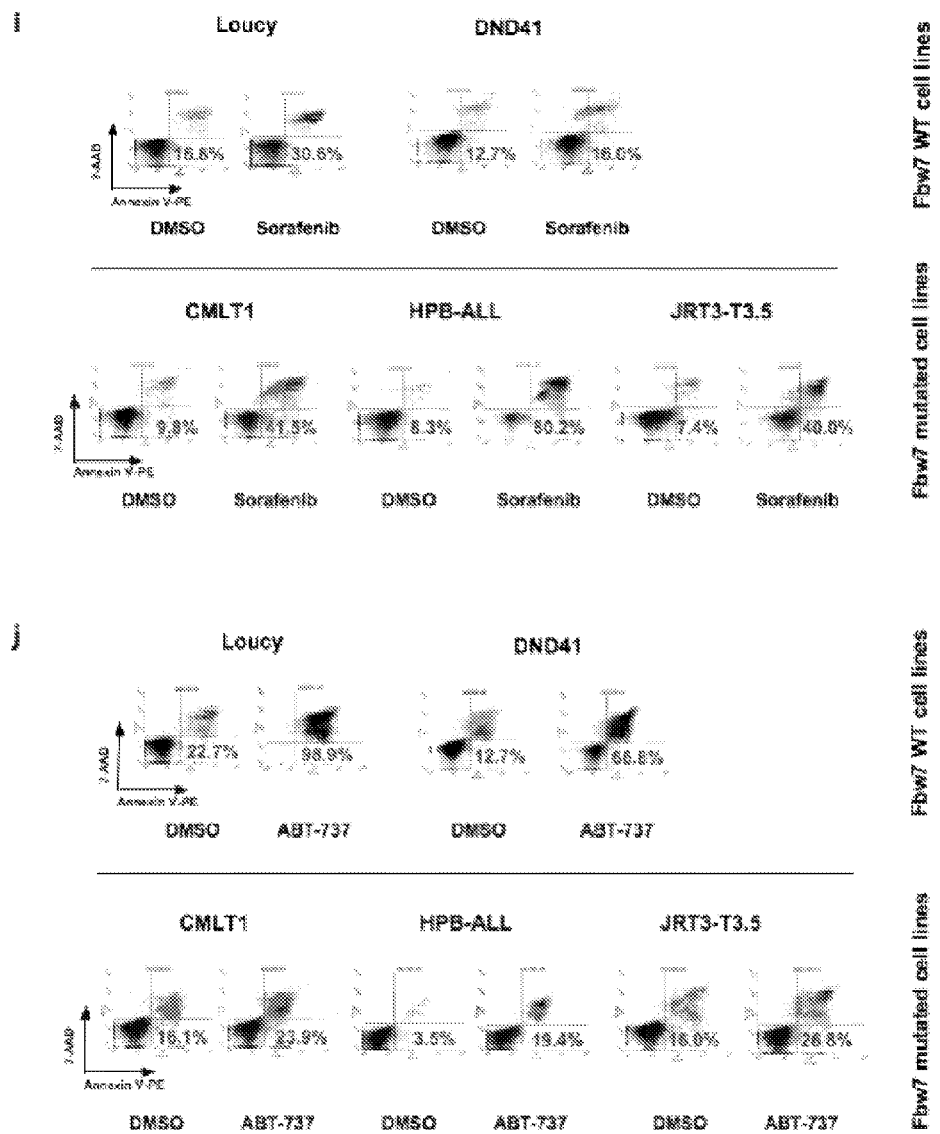
Figures 1, 14:
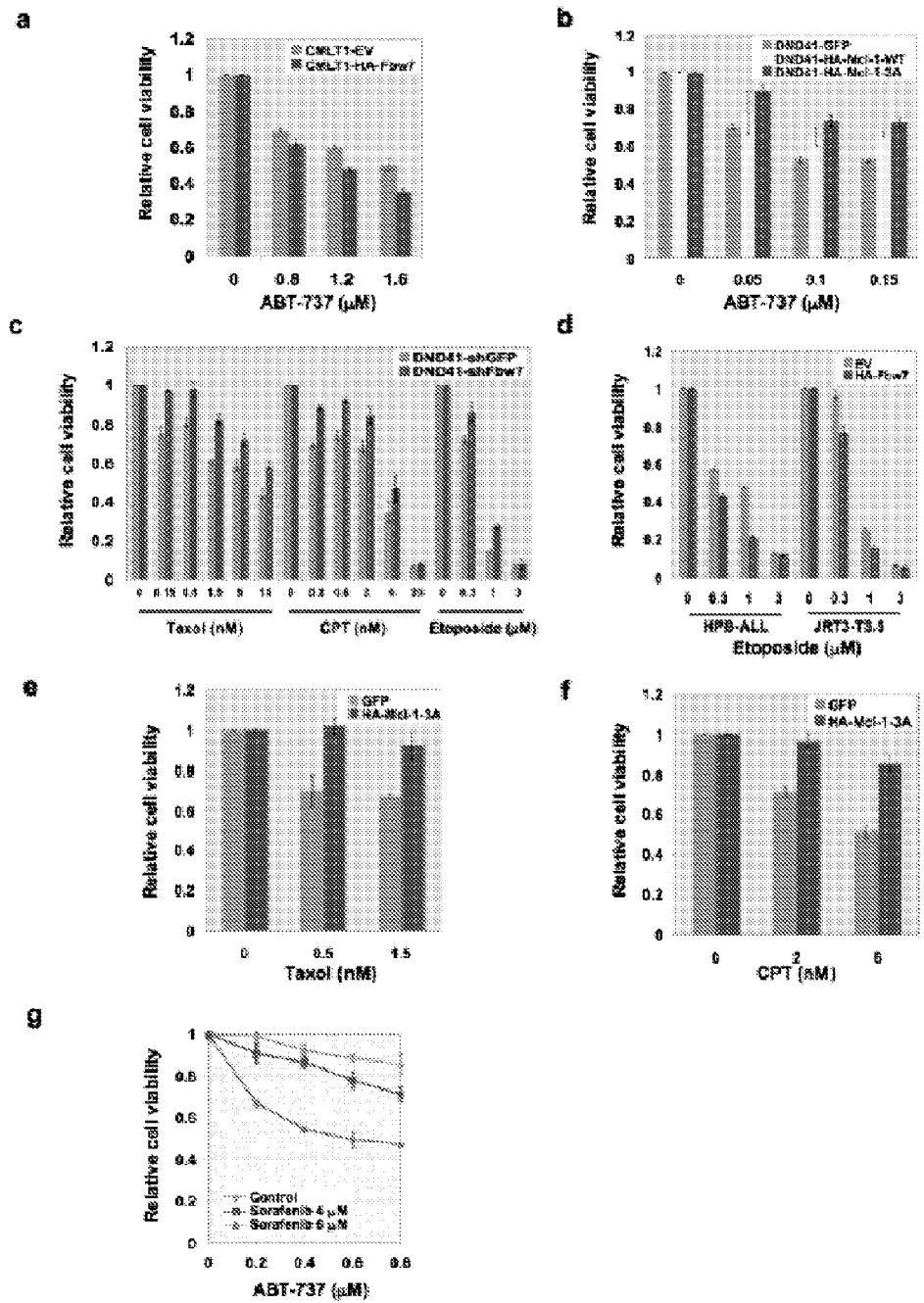
FIG. 14 shows that manipulating Fbw7 activity changes ABT-737 sensitivity.
Figures 2, 14:
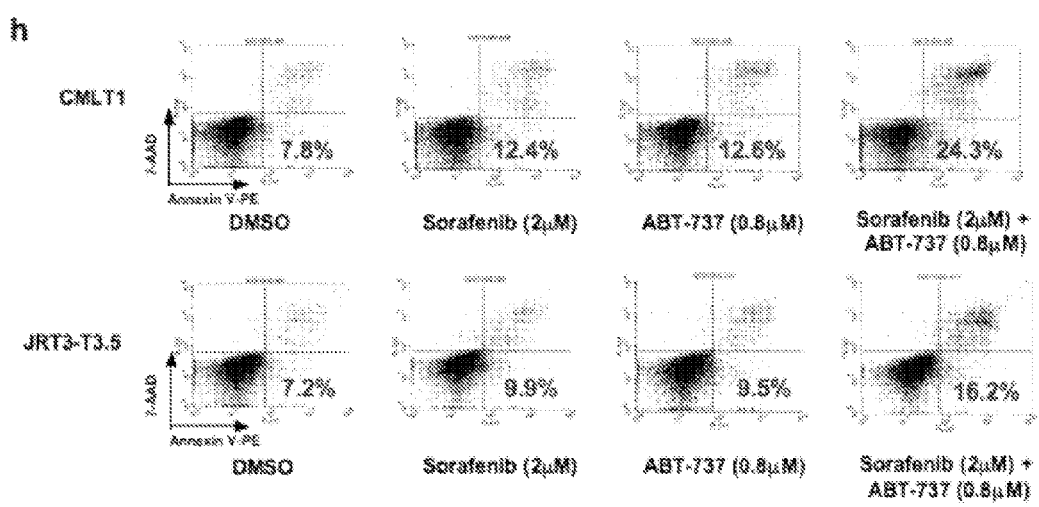

Next, how Fbw7 affects the cellular apoptotic response by modulating Mcl-1 abundance was explored. The results are shown in FIGS. 12, 13, and 14. As predicted, Fbw7−/− mouse thymocytes and Fbw7-deficient human T-ALL cells with increased Mcl-1 levels were less sensitive to apoptotic stimuli (FIG. 13a-f). More interestingly, compared with T-ALL cell lines with wild-type Fbw7, Fbw7-deficient T-ALL cells with elevated Mcl-1 expression (FIG. 1f and FIG. 13h) were more sensitive to sorafenib, which can effectively reduce Mcl-1 expression (FIG. 12a, FIG. 13g-i)[19, 20]. Although sorafenib's ability to repress Mcl-1 has been attributed to inactivating MAPK kinase and/or activating GSK-3 activity[19], the exact mechanism remains unclear. Nonetheless, this data suggests that Fbw7-deficient T-ALL cell lines might require elevated levels of Mcl-1 to evade apoptosis, a phenotype known as "oncogene addiction"[21]. On the other hand, Fbw7-deficient T-ALL cell lines were more resistant to ABT-737 (FIG. 12a, FIGS. 13g and 13j). The BH3 mimetic ABT-737 is a pan-inhibitor of the Bcl-2 family of anti-apoptotic proteins, which is reported to effectively kill leukemia cells[22]. However, leukemia cells with elevated Mcl-1 are refractory to ABT-737[23,24] primarily because ABT-737 fails to inactivate Mcl-1[22]. Experimental evidence from both 7-AAD/Annexin V double staining (FIG. 13j) and immunoblots against apoptotic biomarkers (FIG. 12b) suggest that ABT-737-induced apoptosis is impaired in Fbw7-deficient T-ALL cells. Moreover, specific depletion of Mcl-1 in multiple Fbw7-deficient T-ALL cell lines restored their sensitivity to ABT-737 (FIG. 12c-d), supporting the notion that increased Mcl-1 expression is the primary cause of desensitization to ABT-737 in vivo[23,24]. It also suggests that Fbw7-deficient T-ALL patients will not respond well to ABT-737 treatment. It was further demonstrated that manipulation of Fbw7 activity or ectopic expression of a non-degradable Mcl-1 in human T-ALL cells affects their ABT-737 sensitivity (FIG. 14a-b) and response to other apoptotic stimuli (FIG. 14c-f).

FIG. 12 shows that elevated Mcl-1 expression protects Fbw7-deficient T-ALL cell lines from ABT-737-induced apoptosis. FIG. 12a illustrates cell viability assays showing that Fbw7-deficient T-ALL cell lines were more sensitive to sorafenib, but resistant to ABT-737 treatment. T-ALL cells were cultured in 10% FBS-containing medium with the indicated concentrations of sorafenib or ABT-737 for 48 hours before performing the cell viability assays. Data was shown as mean±SD for three independent experiments. FIG. 12b shows immunoblot analysis of the indicated human T-ALL cell lines with or without ABT-737 (0.8 mM) treatment. FIG. 12c shows specific depletion of endogenous Mcl-1 expression restored ABT-737 sensitivity in the indicated Fbw7-deficient T-ALL cell lines. Various T-ALL cells were cultured in 10% FBS-containing medium with the indicated concentrations of ABT-737 for 48 hours before performing the cell viability assays, or with or without ABT-737 (0.8 mM) treatment for 24 hours before collecting whole cell lysates for immunoblot analysis with the indicated antibodies. For cell viability assays, data was shown as mean±SD for three independent experiments. FIG. 12d shows 7-Amino-Actinomycin D (7-AAD)/Annexin V double-staining FACS analysis to detect the percentage of ABT-737-induced apoptosis in the indicated Fbw7-deficient T-ALL cell lines where the endogenous Mcl-1 was depleted by lentiviral shRNA treatment (lentiviral shGFP was used as a negative control). Various T-ALL cells were cultured in 10% FBS-containing medium with or without ABT-737 (0.8 mM) treatment for 48 hours before the FACS analysis. Numbers indicate the percentage of apoptotic cells. FIG. 12e shows 7-AAD/Annexin V double-staining FACS analysis to demonstrate that sorafenib treatment restores ABT-737 sensitivity to Fbw7-deficient HPB-ALL cells. HPB-ALL cells were cultured in 10% FBS-containing medium with the indicated concentrations of sorafenib and/or ABT-737 for 48 hours before the FACS analysis. Numbers indicate the percentage of apoptotic cells.

FIG. 13 shows that Fbw7-deficient T-ALL cell lines are more sensitive to sorafenib, but have increased resistance to ABT-737 treatment. FIG. 13a shows results from thymocytes isolated from 8-wk-old Lck-Cre/Fbw7$^{+/fl}$ (Control) or Lck-Cre/Fbw7$^{fl/fl}$ (Fbw7 KO) that were cultured at 37° C. for the indicated times and then stained with annexin V for determination of the proportion of apoptotic cells by flow cytometry. Data are represented as mean±SD from three independent experiments. FIG. 13b shows results from thymocytes of 8-wk-old Lck-Cre/Fbw7$^{+/fl}$ (Control) or Lck-Cre/Fbw7$^{fl/fl}$ (Fbw7 KO) that were cultured for 12 h at 37° C. with the indicated concentrations of dexamethasone and then analyzed as in (a). , P<0.01 using the Student t test. *, P<0.005 using the Student t test. FIG. 13c-f illustrate cell viability assays showing that compared with T-ALL cell lines with wild-type Fbw7, Fbw7-deficient T-ALL cell lines were more resistant to multiple apoptotic stimuli including etoposide (c), camptothecin (CPT) (d), Taxol (e) and Nocodazole (f). Data was shown as mean±SD for three independent experiments. FIG. 13g illustrates cell viability assays showing that compared with T-ALL cell lines with wild-type Fbw7, Fbw7-deficient T-ALL cell lines were more sensitive to sorafenib, but resistant to ABT-737 treatment. T-ALL cells were cultured in 0.5% FBS-containing medium with the indicated concentrations of sorafenib or ABT-737 for 48 hours before performing the cell viability assays. Data was shown as mean±SD for three independent experiments. FIG. 13h shows immunoblot analysis of the indicated human T-ALL cell lines with or without sorafenib treatment in 0.5% FBS-containing medium. FIG. 13i shows 7-AAD/Annexin V double-staining FACS analysis to detect the percentage of sorafenib-induced apoptosis of the indicated Fbw7-deficient T-ALL cell lines. Various T-ALL cells were cultured in 0.5% FBS-containing medium with or without sorafenib (2 mM) treatment for 48 hours before the FACS analysis. Numbers indicate the percentage of apoptotic cells. FIG. 13j shows 7-AAD/Annexin V double staining FACS analysis to detect the percentage of ABT-737-induced apoptosis of the indicated Fbw7-deficient T-ALL cell lines. Various T-ALL cells were cultured in 10% FBS-containing medium with or without ABT-737 (0.8 mM) treatment for 48 hours before the FACS analysis. Numbers indicate the percentage of apoptotic cells.

FIG. 14 demonstrates that manipulating Fbw7 activity changes ABT-737 sensitivity. FIG. 14a illustrates cell viability assays showing that re-introduction of wild-type Fbw7 into the Fbw7-deficient T-ALL (CMLT1) cell line partially restored its sensitivity to ABT-737 treatment. The CMLT1 cells were cultured in 10% FBS-containing medium with the indicated concentrations of ABT-737 treatment for 48 hours before performing the cell viability assays. Data was shown as mean±SD for three independent experiments. FIG. 14b illustrates cell viability assays showing that re-introduction of wild-type or 3A-Mcl-1 into DND41 cells results in an increase in resistance to ABT-737 treatment. Indicated DND41 cells were cultured in 10% FBS-containing medium with the indicated concentrations of ABT-737 treatment for 48 hours before performing the cell viability assays. Data was shown as mean±SD for three independent experiments. FIG. 14c illustrates cell viability assays showing that depletion of Fbw7 in DND41 cells resulted in elevated resistance to multiple apoptotic stimuli. Data was shown as mean±SD for three independent experiments. FIG. 14d illustrates cell viability assays showing that re-introduction of wild-type Fbw7 into the Fbw7-deficient T-ALL cell lines (HPB-ALL and JRT3-T3.5) partially restored their sensitivity to etoposide-induced apoptosis. Data was shown as mean±SD for three independent experiments. FIG. 14e-f illustrate cell viability assays showing that re-introduction of 3A-Mcl-1 into DND41 cells results in an increase in resistance to Taxol (e) and CPT (f) treatment. Data was shown as mean±SD for three independent experiments. FIG. 14g illustrates cell viability assays to demonstrate that sorafenib treatment restored ABT-737 sensitivity in Fbw7-deficient HPB-ALL cells. HPB-ALL cells were cultured in 10% FBS-containing medium with the indicated concentrations of sorafenib and ABT-737 for 48 hours before performing the cell viability assays. In order to score the effects of increasing concentrations of ABT-737 on cell viability, each reading was scaled relative to the respective sorafenib treatment with 0 mM ABT-737 set as 100%. Data was shown as mean±SD for three independent experiments. FIG. 14h shows 7-AAD/Annexin V double-staining FACS analysis to demonstrate that sorafenib treatment restored ABT-737 sensitivity of Fbw7-deficient CMLT1 and JRT3-T3.5 cells. CMLT1 and JRT3-T3.5 cells were cultured in 10% FBS-containing medium with the indicated concentrations of sorafenib and/or ABT-737 for 48 hours before the FACS analysis. Numbers indicate the percentage of apoptotic cells.

These results imply that inhibition of Mcl-1 could be used to restore ABT-737 sensitivity in Fbw7-deficient T-ALL cells. Given that the clinical application of siRNA- or shRNA-mediated target extinction is not yet mature due to delivery challenges, instead small molecule strategies were exploited to reduce Mcl-1 expression, specifically with the use of sorafenib (FIG. 13h). To this end, combined use of sorafenib and ABT-737 produced a dose-dependent increase of ABT-737 sensitivity for HPB-ALL (FIG. 13g), which correlated with a significant increase in the induction of apoptosis (FIG. 12e). Similar results were obtained with other Fbw7-deficient T-ALL cell lines (FIG. 14h).

These studies provide experimental evidence for a role of Fbw7 in governing the apoptotic pathway by controlling Mcl-1 destruction. Mcl-1 plays a key role in regulating the cellular apoptosis of T cells[14], but not other tissue types such as liver cells. Therefore, these studies also provide a possible mechanism for why loss of Fbw7 is frequently seen in T-ALL patients. Although other E3 ubiquitin ligases including c-Mule[25] and b-TRCP[17] have been implicated in Mcl-1 stability control, c-Mule activity was not implicated in GSK3-dependent regulation of Mcl-1 (FIG. 15a-e)[17,25]. Additionally, no correlation was found between c-Mule and Mcl-1 expression in various T-ALL cells (FIG. 15f), excluding a physiological role for c-Mule in regulating Mcl-1 abundance in T-ALL. It was further found that depletion of Fbw7, but not b-TRCP, leads to a significant induction of Mcl-1 (FIG. 1b and FIG. 15a-c). Array CGH analysis demonstrated a high frequency of Fbw7 loss[2], but not simultaneous loss of b-TRCP1 and b-TRCP2 in T-ALL (data not shown).

Figure 15:
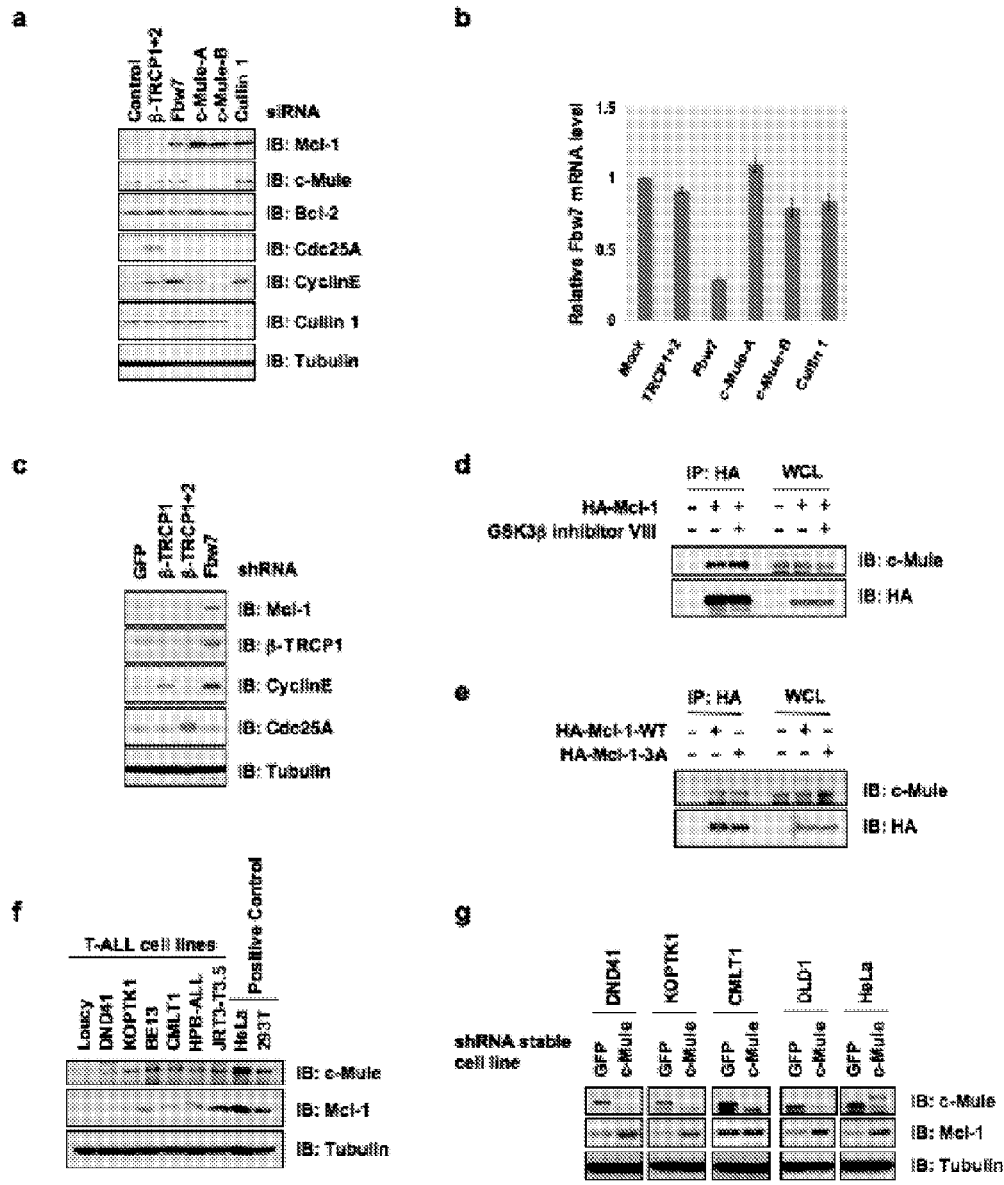
FIG. 15 shows that c-Mule is not the physiological E3 ubiquitin ligase for Mcl-1 in T-ALL cell lines.

FIG. 15 demonstrates that c-Mule is not the physiological E3 ubiquitin ligase for Mcl-1 in T-ALL cell lines. FIG. 15a shows immunoblot analysis of HeLa cells transfected with the indicated siRNA oligonucleotides. FIG. 15b shows real-time RT-PCR analysis to examine the Fbw7 mRNA levels after treatments with the various siRNA oligos in (a). Data was shown as mean±SD for three independent experiments. FIG. 15c shows immunoblot analysis of HeLa cells transfected with the indicated shRNA constructs. FIG. 15d shows immunoblot (IB) analysis of whole cell lysates (WCL) and immunoprecipitates (IP) derived from 293T cells transfected with HA-Fbw7. Thirty hours post-transfection, cells were pretreated with 20 μM MG132 for 8 hours to block the proteasome pathway before harvesting. Where indicated, 25 μM GSK3b inhibitor VIII (with DMSO as a negative control) was added for 8 hours before harvesting. FIG. 15e shows immunoblot (IB) analysis of whole cell lysates (WCL) and immunoprecipitates (IP) derived from 293T cells transfected with HA-Fbw7 together with the indicated Myc-Mcl-1 constructs. Thirty hours post-transfection, cells were pretreated with 10 μM MG132 for 10 hours to block the proteasome pathway before harvesting. FIG. 15f shows immunoblot analysis of the indicated human T-ALL cell lines cultured in 10% FBS-containing medium. HeLa and 293T cell lines were included as positive controls for detection of the endogenous c-Mule expression. FIG. 15g shows results from various cell lines were infected with the lentiviral shMule construct (with shGFP as a negative control) and selected with 1 μg/ml puromycin to eliminate the non-infected cells. Whole cell lystates were collected for immunoblot analysis with the indicated antibodies.

Altogether, without wishing to be bound by theory, these data support the hypothesis that Fbw7 is a physiological E3 ubiquitin ligase for Mcl-1 with USP9X as the nominated deubiquitinase[26], and loss of Fbw7 contributes to T-ALL development via Mcl-1 upregulation. More importantly, these studies suggest that there is a correlation between Fbw7 genetic status and ABT-737 sensitivity and further provide insight into the usage of Mcl-1 inhibitors as a practical method to specifically kill Fbw7-deficient T-ALL cells. This work provides a basis for the rational treatment of FBW7 deficient neoplasm, for example, FBW7 deficient leukemias (e.g., in FBW7 deficient T-ALL patients) with Mcl-1 antagonists, or agents that significantly reduce Mcl-1 expression or activity, e.g., sorefanib, obatoclax, the MCL-1 BH3 helix SAHB, or any other Mcl-1 inhibitor described herein or known to those of skill in the art.

Materials and Methods

Methods Summary

Expression plasmid constructs, proteins, antibodies and cell lines are described in the Methods. The sequences of various siRNA oligos used in this study are also listed in the Methods section. Mcl-1 in vivo phosphorylation was detected by mass spectrometry analysis, and the identified major GSK3 phosphorylation sites were examined by in vitro kinase assays. All mutants were generated using PCR and the sequences were verified. Fbw7-mediated Mcl-1 destruction and ubiquitination were examined by cell-based ubiquitination and degradation assays. Cell viability assays were used to detect the response of various T-ALL cell lines to sorafenib and ABT-737. Annexin V/7-AAD double staining was used to detect the percentage of cellular apoptosis. A detailed description of the experimental procedures is provided in the Methods section.

Plasmids:

HA-Fbw7 and HA-GSK3 constructs were described previously[6]. Fbw7 cDNA was subcloned using the Pfu polymerase (Stratagene) into the pBabe-Puro-HA retrovirus vector. Myc-Mcl-1 WT, Myc-Mcl-1 3A, and GST-Mcl-1 WT constructs were kind gifts from Dr. Mien-Chie Hung. Fbw7 and Mcl-1 mutants were generated with the QuikChange XL Site-Directed Mutagenesis Kit (Stratagene) according to the manufacturer's instructions. HA-ERK1, shERK1 and shERK2 constructs were kind gifts from Dr. John Blenis. Flag-β-TRCP1, Flag-Ubiquitin, shTRCP1 and shTRCP1+2 retroviral constructs were kind gifts from Dr. Wade Harper. shFbw7 retroviral vector was purchased from Addgene, which has been validated and described previously[27]. To generate the lentiviral shFbw7 and sh-c-Mule vectors, DNA oligos for shRNA against Fbw7 and c-Mule were annealed and subcloned into AgeI and EcoRI sites of the pLKO lentiviral plasmid. The following are DNA oligo sequences for the Fbw7 shRNA (sense; 5'-CCGGAACCTTCTCTG-GAGAGAGAAACTCGAGTTTCTCTCTCCAGA-GAAGGTTTTT TTG-3' (SEQ ID NO: 30), anti-sense; 5'-AATTCAAAAAAACCTTCTCTGGAGAGA-GAAACTCGAGTTTCTCTCTCCAGAGAAG GTT-3' (SEQ ID NO: 31)), and for c-Mule shRNA (sense; 5'-CCG-GAATTGCTATGTCTCTGGGACACTCGAGTGTCCCA-GAGACATAGCAATTTTT TTG-3' (SEQ ID NO: 32), anti-sense; 5'-AATTCAAAAAAATTGCTATGTCTCTGGGACACTC-GAGTGTCCCAGAGACATAGCA ATT-3' (SEQ ID NO: 33)). Lentiviral shRNA constructs against GFP and Mcl-1 were obtained from Dr. William Hahn. WT-Mcl-1 and 3A-Mcl-1 cDNAs were amplified with PCR and subcloned into the BamH I and Sal I sites of the pLenti-GFP-Puro construct (Addgene, Cat. No.: 658-5).

Antibodies and Reagents:

Anti-c-Myc antibody (sc-40), polyclonal anti-HA antibody (SC-805), anti-Cyclin A antibody (SC-751), anti-Plk1 antibody (SC-17783), anti-Cullin-1 antibody (sc-70895), anti-Rictor antibody (sc-81538), anti-p27 antibody (sc-528), anti-Skp1 antibody (sc-7163), anti-Mcl-1 antibody (sc-819) and anti-Cyclin E antibody (SC-247) were purchased from Santa Cruz. Anti-tubulin antibody (T-5168), polyclonal anti-FLAG antibody (F2425), monoclonal anti-FLAG antibody (F-3165), anti-1-Catenin antibody (C7207), anti-Vinculin antibody (V9131), peroxidase-conjugated anti-mouse secondary antibody (A4416) and peroxidase-conjugated anti-rabbit secondary antibody (A4914) were purchased from Sigma. Anti Mcl-1 antibody (4572), anti-Bcl-2 antibody (2872), anti-COX IV antibody (4850), anti-cleaved Caspase-3 (Asp175) antibody (9661), anti-cleaved PARP (Asp214) antibody (9541), anti-ERK1/2 antibody (4695), anti-c-Jun antibody (9162), anti-phospho-GSK3b (Ser-9) antibody (9336) and anti-Bim antibody (4582) were purchased from Cell Signaling. Anti-c-Mule antibody (A300-486A) was purchased from Bethyl. Monoclonal anti-HA antibody (MMS-101P) was purchased from Convace. Anti-Rbx1 antibody (RB-069P1) was purchased from Neomarker. Anti-Mcl-1 antibody (559027) was purchased from BD Pharmingen. Anti-GFP antibody (632380) and anti-Cullin-1 antibody (32-2400) were purchased from Invitrogen. Anti-Cdh1 antibody (CC43) was purchased from Oncogene. Oligofectamine, Lipofectamine and Plus reagents were purchased from Invitrogen. GSK3b inhibitor VIII was purchased from Calbiochem.

siRNAs:

Human siRNA oligos against Fbw7, Skp2, Cdh1 and Cullin-1 have been described previously[6,28,29]. A human siRNA oligo which can deplete both 13-TRCP1 and (3-TRCP2 (sense, 5'-AAGUGGAAUUUGUGGAACAUC-3' (SEQ ID NO: 34)) was purchased from Dharmacon. Human siRNA oligos against c-Mule (sense, 5'-CAUGC-CGCAAUCCAGACAUAU-3' (SEQ ID NO: 35))[25] and (sense, 5'-AAUUGCUAUGUCUCUGGGACA-3' (SEQ ID NO: 36))[30] have been validated previously and were purchased from Dharmacon. Luciferase GL2 siRNA oligo was purchased from Dharmacon. siRNA oligos to deplete endogenous Rbx1 (AACUGUGCCAUCUGCAGGAACAA (SEQ ID NO: 37)), Cullin1 (GGUCGCUUCAUAAACAACAUU (SEQ ID NO: 38)), and Rictor (AAACUU-GUGAAGAAUCGUAUCUU (SEQ ID NO: 39)) were synthesized by Dharmacon. Cocktailed siRNAs targeting Skp1 were purchased from Invitrogen (1299003). A GSK3a siRNA oligo (6312) and a GSK3a/b siRNA oligo (6301) were purchased from Cell Signaling. The GSK3b siRNA oligo (51012) was purchased from Ambion. As described previously, siRNA oligos were transfected into subconfluent cells with Oligofectamine or Lipofectamine 2000 (Invitrogen) according to the manufacturer's instructions[6].

Cell Culture:

Cell culture including synchronization and transfection has been described[6,28]. Wild type and Fbw7−/− DLD1 cell lines were kind gifts from Dr. Bert Vogelstein. Murine T-ALL cell lines derived from Tall transgenic mice were kind gifts from Dr. Michele A. Kelliher. Human T-ALL cell lines were previously described[2]. Loucy and CMLT1 T-ALL cell lines were obtained from Jon Aster. For various assays described below, T-ALL cells were cultured in either 0.5% FBS or 10% FBS-containing medium for sorafenib (Alexis Biochemicals) or ABT-737 (Symansis) treatment. In the case of combined treatment with both sorafenib and ABT-737, T-ALL cells were maintained in 10% FBS-containing medium. Lentiviral shRNA virus packaging, retrovirus packaging, and subsequent infections were performed as described previously[28]. For cell viability assays, cells were plated at 10,000 per well in 96-well plates, and incubated with the appropriate medium containing sorafenib, ABT-737 or DMSO for 48 h. Assays were performed with CellTiter-Glo Luminescent Cell Viability Assay kit according to the manufacturer's instructions (Promega). For detection of apoptosis, cells treated with various drugs were stained with propidium iodide (Roche), or co-stained with Annexin V-PE and 7-amino-actinomycin D (Annexin V-PE Apoptosis Detection Kit I, BD Bioscience) according to the manufacturer's instructions. Stained cells were sorted with Dako-Cytomation MoFlos sorter (Dako) at the Dana-Farber Cancer Institute FACS core facility.

Immunoblots and Immunoprecipitation:

Cells were lysed in EBC (50 mM Tris pH 8.0, 120 mM NaCl, 0.5% NP-40) buffer supplemented with protease inhibitors (Complete Mini, Roche) and phosphatase inhibitors (phosphatase inhibitor cocktail set I and II, Calbiochem). The protein concentrations of the lysates were measured using the Bio-Rad Bradford protein assay reagent on a Beckman Coulter DU-800 spectrophotometer. The lysates were then resolved by SDS-PAGE and immunoblotted with the indicated antibodies. For immunoprecipitation, 800 µg lysates were incubated with the appropriate antibody (1-2 µg) for 3-4 h at 4° C. followed by one-hour incubation with Protein-A Sepharose beads (GE Healthcare). Immuno-complexes were washed five times with NETN buffer (20 mM Tris, pH 8.0, 100 mM NaCl, 1 mM EDTA and 0.5% NP-40) before being resolved by SDS-PAGE and immunoblotted with the indicated antibodies. Quantification of the immunoblot band intensity was performed with Image J software.

Detection of Mcl-1 Phosphorylation Sites In Vivo:

To map Mcl-1 phosphorylation status in vivo, 293T cells were transfected with HA-Mcl-1 using the calcium phosphate method. Thirty hours post-transfection, 293T cells were treated with 10 mM MG132 for 16 hours to block the 26S proteasome pathway prior to collecting the whole cell lysates for HA-immunoprecipitation. After extensive washing with NETN buffer, the HA-immunoprecipitates were separated by SDS-PAGE and visualized by colloidal Coomassie Blue. The band containing Mcl-1 was excised and treated with DTT to reduce disulfide bonds and iodoacetamide to derivatize cysteine residues. In-gel digestion of the protein was done using trypsin or chymotrypsin. The resulting peptides were extracted from the gel and analyzed by nanoscale-microcapillary reversed phase liquid chromatography tandem mass spectrometry (LC-MS/MS). Peptides were separated across a 37-min gradient ranging from 4% to 27% (v/v) acetonitrile in 0.1% (v/v) formic acid in a microcapillary (125 µm×18 cm) column packed with $C_{18}$ reverse-phase material (Magic C18AQ, 5 µm particles, 200 Å pore size, Michrom Bioresources) and on-line analyzed on The LTQ Orbitrap XL™ hybrid FTMS (Thermo Scientific, Bremen, Germany). For each cycle, one full MS scan acquired on the Orbitrap at high mass resolution was followed by ten MS/MS spectra on the linear ion trap XL from the ten most abundant ions. MS/MS spectra were searched using the SEQUEST algorithm against a database created on the basis of a protein sequence database containing the sequence for Mcl-1, for common contaminants, such as human keratins protein with static modification of cysteine carboxymethylation, dynamic modification of methionine oxidation and serine, threonine and tyrosine phosphorylation. All peptide matches were filtered based on mass deviation, tryptic state, XCorr and dCn and confirmed by manual validation. The reliability of site-localization of phosphorylation events was evaluated using the Ascore algorithm.

Real-Time RT-PCR Analysis:

RNA was extracted using the Qiagen RNeasy mini kit, and the reverse transcription reaction was performed using the ABI Taqman Reverse Transcriptional Reagents (N808-0234). After mixing the resulting template with Mcl-1 (Hs00172036_ml) or GAPDH (Hs99999905_ml) primers and ABI Taqman Fast Universal PCR Master Mix (4352042), the real-time RT-PCR was performed with the ABI-7500 Fast Real-time PCR system. Fbw7 (Hs00217794_ml), Skp2 (Hs00180634_ml), b-TRCP1 (Hs00182707_ml), Mcl-1 (Hs00172036_ml) and GAPDH (Hs99999905_ml) primers were purchased from ABI.

Protein Degradation Analysis:

Cells were transfected with Myc-Mcl-1 along with HA-Fbw7, or Flag-β-TRCP1, and GFP as a negative control, in the presence or absence of HA-GSK3 and/or HA-ERK1. For half-life studies, cycloheximide (20 µg/ml, Sigma) was added to the media 40 h post-transfection. At various time points thereafter, cells were lysed and protein abundances were measured by immunoblot analysis.

In vivo Ubiquitination Assay:

Cells were transfected with a plasmid encoding Flag-Ubiquitin along with Myc-Mcl-1 and HA-Fbw7 in the presence or absence of HA-GSK3. Thirty-six hours after transfection, cells were treated with the proteasome inhibitor MG132 (30 mM, Calbiochem) for 6 hours, and then harvested. Anti-Myc immunoprecipitates were recovered and immunoblotted with the anti-Flag antibody. Alternatively, cells were transfected with His-Ubiquitin along with Myc-Mcl-1 and HA-Fbw7 in the presence or absence of HA-GSK3. Thirty-six hours after transfection, cells were harvested, and the lysates were incubated with Ni-NTA matrices (Qiagen) at 4° C. for 12 h in the presence of 8 M Urea pH 7.5. Immobilized proteins were washed five times with 8 M Urea pH 6.3 before being resolved by SDS-PAGE and immunoblotted with the anti-Myc antibody.

In vitro Ubiquitination Assay:

The in vitro ubiquitination assays were performed as described previously[8]. To purify the $SCF^{Fbw7}$ E3 ligase complex, 293T cells were transfected with vectors encoding GST-Fbw7, HA-Cullin-1, Myc-Skp1 and Flag-Rbx1. The $SCF^{Fbw7}$ E3 complexes were purified from the whole cell lysates using GST-agarose beads. Purified, recombinant GST-Mcl-1 proteins were incubated with purified $SCF^{Fbw7}$ complexes in the presence of purified, recombinant active E1, E2 (UbcH5a and UbCH3), ATP and ubiquitin. The reactions were stopped by the addition of 2×SDS-PAGE sample buffer and the reaction products were resolved by SDS-PAGE gel and probed with the indicated antibodies.

In Vitro Kinase Assay:

GSK-3 was purchased from New England Biolabs. The in vitro kinase reaction was performed according to the manufacturer's instructions. Briefly, 5 µg of the indicated GST fusion proteins were incubated with purified active GSK3 in the presence of 5 µCi [γ-$^{32}$] ATP and 20 µM cold ATP in the kinase reaction buffer for 20 min. The reaction was stopped by the addition of SDS-containing lysis buffer, resolved on SDS-PAGE, and detected by autoradiography.

Mcl-1 Binding Assays:

Binding to immobilized GST proteins was performed as described previously[28]. Where indicated, the GST-Mcl-1 proteins were incubated with GSK3 in the presence of ATP for 1 h prior to the binding assays.

Subcellular Fractionation:

Mitochondrial and cytosolic (S100) fractions were prepared by resuspending HeLa cells in 0.8 ml ice-cold buffer A (250 mM sucrose, 20 mM HEPES [pH 7.4], 10 mM KCl, 1.5 mM MgCl$_2$, 1 mM EDTA, 1 mM EGTA, 1 mM DTT, 17 mg/ml phenylmethylsulfonyl fluoride, 8 mg/ml aprotinin, 2 mg/ml leupeptin). Cells were then passed through an ice-cold cylinder cell homogenizer. Unlysed cells and nuclei were pelleted through a 10 min, 750 g spin. The recovered supernatant was spun at 10,000 g for 25 min. This pellet was resuspended in buffer A and represents the mitochondrial fraction. The supernatant was spun at 100,000 g for 1 hr. The supernatant from this final centrifugation represents the S100 (cytosolic) fraction.

Mice:

Generation of conditional Fbw7 knockout mice (Lck-Cre/Fbw7$^{fl/fl}$ and Mx1-Cre/Fbw7$^{fl/fl}$) was described previously[3,4].

In Vivo Imaging:

CMLT1 cells were infected with lentiviral vectors encoding a shRNA against Mcl-1 (shMcl-1) or an irrelevant control (shGFP). After selection in puromycin 1 µg/ml, cells were engineered for in vivo imaging by transduction with a retrovirus encoding a fusion of firefly luciferase fused to neomycin phosphotransferase, and then selected with G418 at 0.5 mg/ml. After selection, the luciferase activity of each engineered cell line was measured and found to have similar reading. Subsequently, equal numbers of viable cells (0.5–1×10$^7$ cells) were injected into NSG mice via the lateral tail vein. Tumor burden was determined using bioluminescence imaging (IVIS Spectrum, Caliper Life Sciences) after intraperitoneal injection of D-Luciferin 75 mg/kg. Total body luminescence was quantified using the Living Images software package (Caliper Life Sciences), and are expressed as photons/second/standardized region of interest (ph/s/ROI) encompassing the entire mouse. Data represented as mean±SEM with statistical significance determined by Student's t-test.

REFERENCES

1. Wood, L. D. et al. The genomic landscapes of human breast and colorectal cancers. Science 318, 1108-13 (2007).
2. Maser, R. S. et al. Chromosomally unstable mouse tumours have genomic alterations similar to diverse human cancers. Nature 447, 966-71 (2007).
3. Onoyama, I. et al. Conditional inactivation of Fbxw7 impairs cell-cycle exit during T cell differentiation and results in lymphomatogenesis. J Exp Med 204, 2875-88 (2007).
4. Matsuoka, S. et al. Fbxw7 acts as a critical fail-safe against premature loss of hematopoietic stem cells and development of T-ALL. Genes Dev 22, 986-91 (2008).
5. Thompson, B. J. et al. The SCFFBW7 ubiquitin ligase complex as a tumor suppressor in T cell leukemia. J Exp Med 204, 1825-35 (2007).
6. Wei, W., Jin, J., Schlisio, S., Harper, J. W. & Kaelin, W. G., Jr. The v-Jun point mutation allows c-Jun to escape GSK3-dependent recognition and destruction by the Fbw7 ubiquitin ligase. Cancer Cell 8, 25-33 (2005).
7. Welcker, M. et al. The Fbw7 tumor suppressor regulates glycogen synthase kinase 3 phosphorylation-dependent c-Myc protein degradation. Proc Natl Acad Sci USA 101, 9085-90 (2004).
8. Koepp, D. M. et al. Phosphorylation-dependent ubiquitination of cyclin E by the SCFFbw7 ubiquitin ligase. Science 294, 173-7 (2001).
9. Gupta-Rossi, N. et al. Functional interaction between SEL-10, an F-box protein, and the nuclear form of activated Notch1 receptor. J Biol Chem 276, 34371-8 (2001).
10. Shaulian, E. & Karin, M. AP-1 as a regulator of cell life and death. Nat Cell Biol 4, E131-6 (2002).
11. Sanchez, I. & Yuan, J. A convoluted way to die. Neuron 29, 563-6 (2001).
12. Akgul, C. Mcl-1 is a potential therapeutic target in multiple types of cancer. Cell Mol Life Sci 66, 1326-36 (2009).
13. Maurer, U., Charvet, C., Wagman, A. S., Dejardin, E. & Green, D. R. Glycogen synthase kinase-3 regulates mitochondrial outer membrane permeabilization and apoptosis by destabilization of MCL-1. Mol Cell 21, 749-60 (2006).
14. Opferman, J. T. et al. Development and maintenance of B and T lymphocytes requires antiapoptotic MCL-1. Nature 426, 671-6 (2003).
15. Wertz, I. E. et al. Regulation of antimitotic resistance by Mcl-1 and SCF/Fbw7. Submitted (2009).
16. Welcker, M. & Clurman, B. E. FBW7 ubiquitin ligase: a tumour suppressor at the crossroads of cell division, growth and differentiation. Nat Rev Cancer 8, 83-93 (2008).
17. Ding, Q. et al. Degradation of Mcl-1 by beta-TrCP mediates glycogen synthase kinase 3-induced tumor suppression and chemosensitization. Mol Cell Biol 27, 4006-17 (2007).
18. Nijhawan, D. et al. Elimination of Mcl-1 is required for the initiation of apoptosis following ultraviolet irradiation. Genes Dev 17, 1475-86 (2003).
19. Panka, D. J., Cho, D. C., Atkins, M. B. & Mier, J. W. GSK-3beta inhibition enhances sorafenib-induced apoptosis in melanoma cell lines. J Biol Chem 283, 726-32 (2008).
20. Yu, C. et al. The role of Mcl-1 downregulation in the proapoptotic activity of the multikinase inhibitor BAY 43-9006. Oncogene 24, 6861-9 (2005).
21. Sharma, S. V. & Settleman, J. Oncogene addiction: setting the stage for molecularly targeted cancer therapy. Genes Dev 21, 3214-31 (2007).
22. Cragg, M. S., Harris, C., Strasser, A. & Scott, C. L. Unleashing the power of inhibitors of oncogenic kinases through BH3 mimetics. Nat Rev Cancer 9, 321-6 (2009).
23. Konopleva, M. et al. Mechanisms of antileukemic activity of the novel Bcl-2 homology domain-3 mimetic GX15-070 (obatoclax). Cancer Res 68, 3413-20 (2008).
24. van Delft, M. F. et al. The BH3 mimetic ABT-737 targets selective Bcl-2 proteins and efficiently induces apoptosis via Bak/Bax if Mcl-1 is neutralized. Cancer Cell 10, 389-99 (2006).
25. Zhong, Q., Gao, W., Du, F. & Wang, X. Mule/ARF-BP1, a BH3-only E3 ubiquitin ligase, catalyzes the polyubiquitination of Mcl-1 and regulates apoptosis. Cell 121, 1085-95 (2005).
26. Schwickart, M. et al. Deubiquitinase USP9X stabilizes MCL1 and promotes tumour cell survival. Nature 463, 103-7.
27. Popov, N. et al. The ubiquitin-specific protease USP28 is required for MYC stability. Nat Cell Biol 9, 765-74 (2007).
28. Gao, D. et al. Phosphorylation by Akt1 promotes cytoplasmic localization of Skp2 and impairs APCCdh1-mediated Skp2 destruction. Nat Cell Biol 11, 397-408 (2009).
29. Benmaamar, R. & Pagano, M. Involvement of the SCF complex in the control of Cdh1 degradation in S-phase. Cell Cycle 4, 1230-2 (2005).
30. Chen, D. et al. ARF-BP1/Mule is a critical mediator of the ARF tumor suppressor. Cell 121, 1071-83 (2005).

All references listed above are incorporated in their entirety by reference herein, as if each and every reference was individually incorporated by reference.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

---

What is claimed is:

1. A method comprising
   (a) determining the expression level and/or the mutation status of the FBW7 gene in a tumor sample obtained from a human subject having T-cell acute lymphoblastic leukemia (T-ALL); and,
   (b) administering a Mcl-1 BH3 helix Stabilized Alpha-Helix of BCL-2 (SAHB) to the subject if the FBW7 expression level is decreased or if the FBW7 gene exhibits a deletion, frameshift mutation, nonsense mutation, or point mutation, wherein the point mutation is a G423V mutation, a R456C mutation, a R456H mutation, a R479L mutation, a R479Q mutation, a R505C mutation, or a D527G mutation, wherein the mutation causes a loss of function of FBW7, wherein the loss of function of FBW7 results in an inability of FBW7 to degrade MCL-1.

2. A method of treating T-cell acute lymphoblastic leukemia (T-ALL), the method comprising administering a Mcl-1 BH3 helix Stabilized Alpha-Helix of BCL-2 (SAHB) to a human subject, wherein the subject has been determined to have decreased FBW7 expression level or a mutation in the FBW7 gene, wherein the mutation is a deletion, frameshift mutation, nonsense mutation, or point mutation, wherein the point mutation is a G423V mutation, a R456C mutation, a R456H mutation, a R479L mutation, a R479Q mutation, a R505C mutation, or a D527G mutation, wherein the mutation causes a loss of function of FBW7, wherein the loss of function of FBW7 results in an inability of FBW7 to degrade MCL-1.

* * * * *

UNITED STATES PATENT AND TRADEMARK OFFICE
CERTIFICATE OF CORRECTION

| | |
|---|---|
| PATENT NO. | : 10,006,089 B2 |
| APPLICATION NO. | : 14/001970 |
| DATED | : June 26, 2018 |
| INVENTOR(S) | : Wei |

It is certified that error appears in the above-identified patent and that said Letters Patent is hereby corrected as shown below:

On the Title Page

(74) Attorney, Agent, or Firm – "Wolf, Greenfield & Socks, P.C." should read --Wolf, Greenfield & Sacks, P.C.--

Signed and Sealed this
Twenty-first Day of August, 2018

Andrei Iancu
*Director of the United States Patent and Trademark Office*

SEQUENCE LISTING

```
<160> NUMBER OF SEQ ID NOS: 39

<210> SEQ ID NO 1
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 1

Gly Asn Asn Thr Ser Thr Asp Gly Ser Leu Pro Ser Thr Pro Pro Pro
1               5                   10                  15

Ala

<210> SEQ ID NO 2
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 2

Gly Asn Asn Thr Ser Thr Asp Gly Ser Leu Pro Ser Thr Pro Pro Pro
1               5                   10                  15

Ala

<210> SEQ ID NO 3
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 3

Gly Asn Ser Pro Ser Thr Asp Gly Ser Leu Pro Ser Thr Pro Pro Pro
1               5                   10                  15

Ala

<210> SEQ ID NO 4
<211> LENGTH: 17
<212> TYPE: PRT
<213> ORGANISM: Artificial Sequence
```

<220> FEATURE:
<223> OTHER INFORMATION: synthetic polypeptide

<400> SEQUENCE: 4

Ser Ser Gly Pro Gly Met Asp Gly Ser Leu Pro Ser Thr Pro Pro Pro
1               5                   10                  15
Ala

<210> SEQ ID NO 5
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 5

Asn Asn Ser Pro Gly Ser Asp Gly Ser Leu Pro Ser Thr Pro Pro Pro
1               5                   10                  15
Ala

<210> SEQ ID NO 6
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 6

Ser Ser Gly Pro Gly Thr Asp Gly Ser Leu Pro Ser Thr Pro Pro Pro
1               5                   10                  15
Ala

<210> SEQ ID NO 7
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 7

Ala Lys Ser Ser Gly Ala Asp Gly Ser Leu Pro Ser Thr Pro Pro Pro
1               5                   10                  15
Pro

<210> SEQ ID NO 8
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 8

Ala Lys Ser Ser Gly Ala Asp Gly Ser Leu Pro Ser Thr Pro Pro Pro
1               5                   10                  15
Pro

<210> SEQ ID NO 9
<211> LENGTH: 6
<212> TYPE: PRT
<213> ORGANISM: Artificial Sequence
<220> FEATURE:
<223> OTHER INFORMATION: synthetic polypeptide

```
<400> SEQUENCE: 9

Thr Pro Pro Leu Ser Pro
1               5

<210> SEQ ID NO 10
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 10

Gly Glu Thr Pro Pro Leu Ser Pro
1               5

<210> SEQ ID NO 11
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 11

Leu Pro Thr Pro Pro Leu Ser Pro
1               5

<210> SEQ ID NO 12
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 12

Leu Leu Thr Pro Pro Gln Ser Gly
1               5

<210> SEQ ID NO 13
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 13

Asp Gly Ser Leu Pro Ser Thr Pro
1               5

<210> SEQ ID NO 14
<211> LENGTH: 33
<212> TYPE: PRT
<213> ORGANISM: Artificial Sequence
<220> FEATURE:
<223> OTHER INFORMATION: synthetic polypeptide

<400> SEQUENCE: 14

Ala Thr Glu Lys Glu Ala Ser Ala Arg Arg Glu Ile Gly Gly Gly Glu
1               5                   10                  15

Ala Gly Ala Val Ile Gly Gly Ser Ala Gly Ala Ser Pro Pro Ser Thr
                20                  25                  30

Leu
```

```
<210> SEQ ID NO 15
<211> LENGTH: 34
<212> TYPE: PRT
<213> ORGANISM: Artificial Sequence
<220> FEATURE:
<223> OTHER INFORMATION: synthetic polypeptide

<400> SEQUENCE: 15

Ala Pro Thr Arg Arg Ala Pro Leu Glu Glu Met Glu Ala Pro Ala Ala
1               5                   10                  15

Asp Ala Ile Met Ser Pro Glu Glu Glu Leu Asp Gly Tyr Glu Pro Glu
            20                  25                  30

Pro Leu

<210> SEQ ID NO 16
<211> LENGTH: 18
<212> TYPE: PRT
<213> ORGANISM: Artificial Sequence
<220> FEATURE:
<223> OTHER INFORMATION: synthetic polypeptide

<400> SEQUENCE: 16

Ser Leu Pro Ser Thr Pro Pro Pro Ala Glu Glu Glu Glu Asp Glu Leu
1               5                   10                  15

Tyr Arg

<210> SEQ ID NO 17
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 17

Gly Asn Asn Thr Ser Thr Asp Gly Ser Leu Pro Ser Thr Pro Pro Pro
1               5                   10                  15

Ala

<210> SEQ ID NO 18
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 18

Val Ile Gly Gly Ser Ala Gly Ala Ser Pro Pro Ser Thr Leu Thr Pro
1               5                   10                  15

Asp

<210> SEQ ID NO 19
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 19

Ala Pro Ala Ala Asp Ala Ile Met Ser Pro Glu Glu Glu Leu Asp Gly
1               5                   10                  15

Tyr
```

```
<210> SEQ ID NO 20
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 20

Pro Leu Leu Glu Leu Val Gly Glu Ser Gly Asn Asn Thr Ser Thr Asp
1               5                   10                  15

Gly

<210> SEQ ID NO 21
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 21

Thr Pro Pro Leu Ser Pro
1               5

<210> SEQ ID NO 22
<211> LENGTH: 33
<212> TYPE: PRT
<213> ORGANISM: Artificial Sequence
<220> FEATURE:
<223> OTHER INFORMATION: synthetic polypeptide

<400> SEQUENCE: 22

Ala Thr Glu Lys Glu Ala Ser Ala Arg Arg Glu Ile Gly Gly Glu
1               5                   10                  15

Ala Gly Ala Val Ile Gly Gly Ser Ala Gly Ala Ser Pro Pro Ser Thr
            20                  25                  30

Leu

<210> SEQ ID NO 23
<211> LENGTH: 34
<212> TYPE: PRT
<213> ORGANISM: Artificial Sequence
<220> FEATURE:
<223> OTHER INFORMATION: synthetic polypeptide

<400> SEQUENCE: 23

Ala Pro Thr Arg Arg Ala Pro Leu Glu Glu Met Glu Ala Pro Ala Ala
1               5                   10                  15

Asp Ala Ile Met Ser Pro Glu Glu Glu Leu Asp Gly Tyr Glu Pro Glu
            20                  25                  30

Pro Leu

<210> SEQ ID NO 24
<211> LENGTH: 18
<212> TYPE: PRT
<213> ORGANISM: Artificial Sequence
<220> FEATURE:
<223> OTHER INFORMATION: synthetic polypeptide

<400> SEQUENCE: 24

Ser Leu Pro Ser Thr Pro Pro Pro Ala Glu Glu Glu Glu Asp Glu Leu
1               5                   10                  15

Tyr Arg
```

<210> SEQ ID NO 25
<211> LENGTH: 350
<212> TYPE: PRT
<213> ORGANISM: Artificial Sequence
<220> FEATURE:
<223> OTHER INFORMATION: synthetic polypeptide

<400> SEQUENCE: 25

```
Met Phe Gly Leu Lys Arg Asn Ala Val Ile Gly Leu Asn Leu Tyr Cys
1               5                   10                  15

Gly Gly Ala Gly Leu Gly Ala Gly Ser Gly Gly Ala Thr Arg Pro Gly
            20                  25                  30

Gly Arg Leu Leu Ala Thr Glu Lys Glu Ala Ser Ala Arg Arg Glu Ile
        35                  40                  45

Gly Gly Gly Glu Ala Gly Ala Val Ile Gly Ser Ala Gly Ala Ser
    50                  55                  60

Pro Pro Ser Thr Leu Thr Pro Asp Ser Arg Arg Val Ala Arg Pro Pro
65                  70                  75                  80

Pro Ile Gly Ala Glu Val Pro Asp Val Thr Ala Thr Pro Ala Arg Leu
                85                  90                  95

Leu Phe Phe Ala Pro Thr Arg Arg Ala Ala Pro Leu Glu Glu Met Glu
            100                 105                 110

Ala Pro Ala Ala Asp Ala Ile Met Ser Pro Glu Glu Glu Leu Asp Gly
        115                 120                 125

Tyr Glu Pro Glu Pro Leu Gly Lys Arg Pro Ala Val Leu Pro Leu Leu
    130                 135                 140

Glu Leu Val Gly Glu Ser Gly Asn Asn Thr Ser Thr Asp Gly Ser Leu
145                 150                 155                 160

Pro Ser Thr Pro Pro Pro Ala Glu Glu Glu Glu Asp Glu Leu Tyr Arg
                165                 170                 175

Gln Ser Leu Glu Ile Ile Ser Arg Tyr Leu Arg Glu Gln Ala Thr Gly
            180                 185                 190

Ala Lys Asp Thr Lys Pro Met Gly Arg Ser Gly Ala Thr Ser Arg Lys
        195                 200                 205

Ala Leu Glu Thr Leu Arg Arg Val Gly Asp Gly Val Gln Arg Asn His
    210                 215                 220

Glu Thr Ala Phe Gln Gly Met Leu Arg Lys Leu Asp Ile Lys Asn Glu
225                 230                 235                 240

Asp Asp Val Lys Ser Leu Ser Arg Val Met Ile His Val Phe Ser Asp
                245                 250                 255

Gly Val Thr Asn Trp Gly Arg Ile Val Thr Leu Ile Ser Phe Gly Ala
            260                 265                 270

Phe Val Ala Lys His Leu Lys Thr Ile Asn Gln Glu Ser Cys Ile Glu
        275                 280                 285

Pro Leu Ala Glu Ser Ile Thr Asp Val Leu Val Arg Thr Lys Arg Asp
    290                 295                 300

Trp Leu Val Lys Gln Arg Gly Trp Asp Gly Phe Val Glu Phe Phe His
305                 310                 315                 320

Val Glu Asp Leu Glu Gly Gly Ile Arg Asn Val Leu Leu Ala Phe Ala
                325                 330                 335

Gly Val Ala Gly Val Gly Ala Gly Leu Ala Tyr Leu Ile Arg
            340                 345                 350
```

<210> SEQ ID NO 26
<211> LENGTH: 271
<212> TYPE: PRT
<213> ORGANISM: Artificial Sequence
<220> FEATURE:
<223> OTHER INFORMATION: synthetic polypeptide

<400> SEQUENCE: 26

```
Met Phe Gly Leu Lys Arg Asn Ala Val Ile Gly Leu Asn Leu Tyr Cys
1               5                   10                  15

Gly Gly Ala Gly Leu Gly Ala Gly Ser Gly Gly Ala Thr Arg Pro Gly
            20                  25                  30

Gly Arg Leu Leu Ala Thr Glu Lys Glu Ala Ser Ala Arg Arg Glu Ile
        35                  40                  45

Gly Gly Gly Glu Ala Gly Ala Val Ile Gly Gly Ser Ala Gly Ala Ser
    50                  55                  60

Pro Pro Ser Thr Leu Thr Pro Asp Ser Arg Arg Val Ala Arg Pro Pro
65                  70                  75                  80

Pro Ile Gly Ala Glu Val Pro Asp Val Thr Ala Thr Pro Ala Arg Leu
                85                  90                  95

Leu Phe Phe Ala Pro Thr Arg Arg Ala Ala Pro Leu Glu Glu Met Glu
            100                 105                 110

Ala Pro Ala Ala Asp Ala Ile Met Ser Pro Glu Glu Glu Leu Asp Gly
        115                 120                 125

Tyr Glu Pro Glu Pro Leu Gly Lys Arg Pro Ala Val Leu Pro Leu Leu
    130                 135                 140

Glu Leu Val Gly Glu Ser Gly Asn Asn Thr Ser Thr Asp Gly Ser Leu
145                 150                 155                 160

Pro Ser Thr Pro Pro Ala Glu Glu Glu Asp Glu Leu Tyr Arg
                165                 170                 175

Gln Ser Leu Glu Ile Ile Ser Arg Tyr Leu Arg Glu Gln Ala Thr Gly
            180                 185                 190

Ala Lys Asp Thr Lys Pro Met Gly Arg Ser Gly Ala Thr Ser Arg Lys
        195                 200                 205

Ala Leu Glu Thr Leu Arg Arg Val Gly Asp Gly Val Gln Arg Asn His
    210                 215                 220

Glu Thr Ala Phe Gln Gly Trp Val Cys Gly Val Leu Pro Cys Arg Gly
225                 230                 235                 240

Pro Arg Arg Trp His Gln Glu Cys Ala Ala Gly Phe Cys Arg Cys Cys
                245                 250                 255

Trp Ser Arg Ser Trp Phe Gly Ile Ser Asn Lys Ile Ala Leu Leu
            260                 265                 270
```

<210> SEQ ID NO 27
<211> LENGTH: 707
<212> TYPE: PRT
<213> ORGANISM: Artificial Sequence
<220> FEATURE:
<223> OTHER INFORMATION: synthetic polypeptide

<400> SEQUENCE: 27

```
Met Asn Gln Glu Leu Leu Ser Val Gly Ser Lys Arg Arg Arg Thr Gly
1               5                   10                  15

Gly Ser Leu Arg Gly Asn Pro Ser Ser Ser Gln Val Asp Glu Glu Gln
            20                  25                  30

Met Asn Arg Val Val Glu Glu Glu Gln Gln Gln Leu Arg Gln Gln
        35                  40                  45
```

Glu Glu Glu His Thr Ala Arg Asn Gly Glu Val Val Gly Val Glu Pro
            50                   55                  60

Arg Pro Gly Gly Gln Asn Asp Ser Gln Gly Gln Leu Glu Glu Asn
 65                  70                  75                  80

Asn Asn Arg Phe Ile Ser Val Asp Glu Asp Ser Ser Gly Asn Gln Glu
                    85                  90                  95

Glu Gln Glu Glu Asp Glu Glu His Ala Gly Glu Gln Asp Glu Glu Asp
            100                 105                 110

Glu Glu Glu Glu Glu Met Asp Gln Glu Ser Asp Asp Phe Asp Gln Ser
            115                 120                 125

Asp Asp Ser Ser Arg Glu Asp Glu His Thr His Thr Asn Ser Val Thr
130                 135                 140

Asn Ser Ser Ser Ile Val Asp Leu Pro Val His Gln Leu Ser Ser Pro
145                 150                 155                 160

Phe Tyr Thr Lys Thr Thr Lys Met Lys Arg Lys Leu Asp His Gly Ser
                    165                 170                 175

Glu Val Arg Ser Phe Ser Leu Gly Lys Lys Pro Cys Lys Val Ser Glu
            180                 185                 190

Tyr Thr Ser Thr Thr Gly Leu Val Pro Cys Ser Ala Thr Pro Thr Thr
                    195                 200                 205

Phe Gly Asp Leu Arg Ala Ala Asn Gly Gln Gly Gln Gln Arg Arg Arg
            210                 215                 220

Ile Thr Ser Val Gln Pro Pro Thr Gly Leu Gln Glu Trp Leu Lys Met
225                 230                 235                 240

Phe Gln Ser Trp Ser Gly Pro Glu Lys Leu Leu Ala Leu Asp Glu Leu
                    245                 250                 255

Ile Asp Ser Cys Glu Pro Thr Gln Val Lys His Met Met Gln Val Ile
            260                 265                 270

Glu Pro Gln Phe Gln Arg Asp Phe Ile Ser Leu Leu Pro Lys Glu Leu
            275                 280                 285

Ala Leu Tyr Val Leu Ser Phe Leu Glu Pro Lys Asp Leu Leu Gln Ala
            290                 295                 300

Ala Gln Thr Cys Arg Tyr Trp Arg Ile Leu Ala Glu Asp Asn Leu Leu
305                 310                 315                 320

Trp Arg Glu Lys Cys Lys Glu Glu Gly Ile Asp Glu Pro Leu His Ile
                    325                 330                 335

Lys Arg Arg Lys Val Ile Lys Pro Gly Phe Ile His Ser Pro Trp Lys
            340                 345                 350

Ser Ala Tyr Ile Arg Gln His Arg Ile Asp Thr Asn Trp Arg Arg Gly
            355                 360                 365

Glu Leu Lys Ser Pro Lys Val Leu Lys Gly His Asp Asp His Val Ile
            370                 375                 380

Thr Cys Leu Gln Phe Cys Gly Asn Arg Ile Val Ser Gly Ser Asp Asp
385                 390                 395                 400

Asn Thr Leu Lys Val Trp Ser Ala Val Thr Gly Lys Cys Leu Arg Thr
                    405                 410                 415

Leu Val Gly His Thr Gly Gly Val Trp Ser Ser Gln Met Arg Asp Asn
            420                 425                 430

Ile Ile Ile Ser Gly Ser Thr Asp Arg Thr Leu Lys Val Trp Asn Ala
            435                 440                 445

Glu Thr Gly Glu Cys Ile His Thr Leu Tyr Gly His Thr Ser Thr Val
450                 455                 460

Arg Cys Met His Leu His Glu Lys Arg Val Val Ser Gly Ser Arg Asp
465                 470                 475                 480

Ala Thr Leu Arg Val Trp Asp Ile Glu Thr Gly Gln Cys Leu His Val
            485                 490                 495

Leu Met Gly His Val Ala Ala Val Arg Cys Val Gln Tyr Asp Gly Arg
        500                 505                 510

Arg Val Val Ser Gly Ala Tyr Asp Phe Met Val Lys Val Trp Asp Pro
    515                 520                 525

Glu Thr Glu Thr Cys Leu His Thr Leu Gln Gly His Thr Asn Arg Val
530                 535                 540

Tyr Ser Leu Gln Phe Asp Gly Ile His Val Val Ser Gly Ser Leu Asp
545                 550                 555                 560

Thr Ser Ile Arg Val Trp Asp Val Glu Thr Gly Asn Cys Ile His Thr
            565                 570                 575

Leu Thr Gly His Gln Ser Leu Thr Ser Gly Met Glu Leu Lys Asp Asn
        580                 585                 590

Ile Leu Val Ser Gly Asn Ala Asp Ser Thr Val Lys Ile Trp Asp Ile
    595                 600                 605

Lys Thr Gly Gln Cys Leu Gln Thr Leu Gln Gly Pro Asn Lys His Gln
610                 615                 620

Ser Ala Val Thr Cys Leu Gln Phe Asn Lys Asn Phe Val Ile Thr Ser
625                 630                 635                 640

Ser Asp Asp Gly Thr Val Lys Leu Trp Asp Leu Lys Thr Gly Glu Phe
            645                 650                 655

Ile Arg Asn Leu Val Thr Leu Glu Ser Gly Gly Ser Gly Gly Val Val
        660                 665                 670

Trp Arg Ile Arg Ala Ser Asn Thr Lys Leu Val Cys Ala Val Gly Ser
    675                 680                 685

Arg Asn Gly Thr Glu Glu Thr Lys Leu Leu Val Leu Asp Phe Asp Val
690                 695                 700

Asp Met Lys
705

<210> SEQ ID NO 28
<211> LENGTH: 627
<212> TYPE: PRT
<213> ORGANISM: Artificial Sequence
<220> FEATURE:
<223> OTHER INFORMATION: synthetic polypeptide

<400> SEQUENCE: 28

Met Cys Val Pro Arg Ser Gly Leu Ile Leu Ser Cys Ile Cys Leu Tyr
1               5                   10                  15

Cys Gly Val Leu Leu Pro Val Leu Leu Pro Asn Leu Pro Phe Leu Thr
            20                  25                  30

Cys Leu Ser Met Ser Thr Leu Glu Ser Val Thr Tyr Leu Pro Glu Lys
        35                  40                  45

Gly Leu Tyr Cys Gln Arg Leu Pro Ser Ser Arg Thr His Gly Gly Thr
    50                  55                  60

Glu Ser Leu Lys Gly Lys Asn Thr Glu Asn Met Gly Phe Tyr Gly Thr
65                  70                  75                  80

Leu Lys Met Ile Phe Tyr Lys Met Lys Arg Lys Leu Asp His Gly Ser
                85                  90                  95

Glu Val Arg Ser Phe Ser Leu Gly Lys Lys Pro Cys Lys Val Ser Glu
            100                 105                 110

```
Tyr Thr Ser Thr Thr Gly Leu Val Pro Cys Ser Ala Thr Pro Thr Thr
            115                 120                 125

Phe Gly Asp Leu Arg Ala Ala Asn Gly Gln Gly Gln Gln Arg Arg Arg
    130                 135                 140

Ile Thr Ser Val Gln Pro Pro Thr Gly Leu Gln Glu Trp Leu Lys Met
145                 150                 155                 160

Phe Gln Ser Trp Ser Gly Pro Glu Lys Leu Leu Ala Leu Asp Glu Leu
                165                 170                 175

Ile Asp Ser Cys Glu Pro Thr Gln Val Lys His Met Met Gln Val Ile
            180                 185                 190

Glu Pro Gln Phe Gln Arg Asp Phe Ile Ser Leu Leu Pro Lys Glu Leu
        195                 200                 205

Ala Leu Tyr Val Leu Ser Phe Leu Glu Pro Lys Asp Leu Leu Gln Ala
    210                 215                 220

Ala Gln Thr Cys Arg Tyr Trp Arg Ile Leu Ala Glu Asp Asn Leu Leu
225                 230                 235                 240

Trp Arg Glu Lys Cys Lys Glu Glu Gly Ile Asp Glu Pro Leu His Ile
                245                 250                 255

Lys Arg Arg Lys Val Ile Lys Pro Gly Phe Ile His Ser Pro Trp Lys
            260                 265                 270

Ser Ala Tyr Ile Arg Gln His Arg Ile Asp Thr Asn Trp Arg Arg Gly
        275                 280                 285

Glu Leu Lys Ser Pro Lys Val Leu Lys Gly His Asp Asp His Val Ile
    290                 295                 300

Thr Cys Leu Gln Phe Cys Gly Asn Arg Ile Val Ser Gly Ser Asp Asp
305                 310                 315                 320

Asn Thr Leu Lys Val Trp Ser Ala Val Thr Gly Lys Cys Leu Arg Thr
                325                 330                 335

Leu Val Gly His Thr Gly Gly Val Trp Ser Ser Gln Met Arg Asp Asn
            340                 345                 350

Ile Ile Ile Ser Gly Ser Thr Asp Arg Thr Leu Lys Val Trp Asn Ala
        355                 360                 365

Glu Thr Gly Glu Cys Ile His Thr Leu Tyr Gly His Thr Ser Thr Val
    370                 375                 380

Arg Cys Met His Leu His Glu Lys Arg Val Val Ser Gly Ser Arg Asp
385                 390                 395                 400

Ala Thr Leu Arg Val Trp Asp Ile Glu Thr Gly Gln Cys Leu His Val
                405                 410                 415

Leu Met Gly His Val Ala Ala Val Arg Cys Val Gln Tyr Asp Gly Arg
            420                 425                 430

Arg Val Val Ser Gly Ala Tyr Asp Phe Met Val Lys Val Trp Asp Pro
        435                 440                 445

Glu Thr Glu Thr Cys Leu His Thr Leu Gln Gly His Thr Asn Arg Val
    450                 455                 460

Tyr Ser Leu Gln Phe Asp Gly Ile His Val Val Ser Gly Ser Leu Asp
465                 470                 475                 480

Thr Ser Ile Arg Val Trp Asp Val Glu Thr Gly Asn Cys Ile His Thr
                485                 490                 495

Leu Thr Gly His Gln Ser Leu Thr Ser Gly Met Glu Leu Lys Asp Asn
            500                 505                 510

Ile Leu Val Ser Gly Asn Ala Asp Ser Thr Val Lys Ile Trp Asp Ile
        515                 520                 525
```

```
Lys Thr Gly Gln Cys Leu Gln Thr Leu Gln Gly Pro Asn Lys His Gln
530                 535                 540

Ser Ala Val Thr Cys Leu Gln Phe Asn Lys Asn Phe Val Ile Thr Ser
545                 550                 555                 560

Ser Asp Asp Gly Thr Val Lys Leu Trp Asp Leu Lys Thr Gly Glu Phe
                565                 570                 575

Ile Arg Asn Leu Val Thr Leu Glu Ser Gly Ser Gly Gly Val Val
                580                 585                 590

Trp Arg Ile Arg Ala Ser Asn Thr Lys Leu Val Cys Ala Val Gly Ser
            595                 600                 605

Arg Asn Gly Thr Glu Thr Lys Leu Leu Val Leu Asp Phe Asp Val
        610                 615                 620

Asp Met Lys
625

<210> SEQ ID NO 29
<211> LENGTH: 589
<212> TYPE: PRT
<213> ORGANISM: Artificial Sequence
<220> FEATURE:
<223> OTHER INFORMATION: synthetic polypeptide

<400> SEQUENCE: 29

Met Ser Lys Pro Gly Lys Pro Thr Leu Asn His Gly Leu Val Pro Val
1               5                   10                  15

Asp Leu Lys Ser Ala Lys Glu Pro Leu Pro His Gln Thr Val Met Lys
                20                  25                  30

Ile Phe Ser Ile Ser Ile Ile Ala Gln Gly Leu Pro Phe Cys Arg Arg
            35                  40                  45

Arg Met Lys Arg Lys Leu Asp His Gly Ser Glu Val Arg Ser Phe Ser
        50                  55                  60

Leu Gly Lys Lys Pro Cys Lys Val Ser Glu Tyr Thr Ser Thr Thr Gly
65                  70                  75                  80

Leu Val Pro Cys Ser Ala Thr Pro Thr Thr Phe Gly Asp Leu Arg Ala
                85                  90                  95

Ala Asn Gly Gln Gly Gln Gln Arg Arg Arg Ile Thr Ser Val Gln Pro
            100                 105                 110

Pro Thr Gly Leu Gln Glu Trp Leu Lys Met Phe Gln Ser Trp Ser Gly
        115                 120                 125

Pro Glu Lys Leu Leu Ala Leu Asp Glu Leu Ile Asp Ser Cys Glu Pro
    130                 135                 140

Thr Gln Val Lys His Met Met Gln Val Ile Glu Pro Gln Phe Gln Arg
145                 150                 155                 160

Asp Phe Ile Ser Leu Leu Pro Lys Glu Leu Ala Leu Tyr Val Leu Ser
                165                 170                 175

Phe Leu Glu Pro Lys Asp Leu Leu Gln Ala Ala Gln Thr Cys Arg Tyr
            180                 185                 190

Trp Arg Ile Leu Ala Glu Asp Asn Leu Leu Trp Arg Glu Lys Cys Lys
        195                 200                 205

Glu Glu Gly Ile Asp Glu Pro Leu His Ile Lys Arg Arg Lys Val Ile
    210                 215                 220

Lys Pro Gly Phe Ile His Ser Pro Trp Lys Ser Ala Tyr Ile Arg Gln
225                 230                 235                 240

His Arg Ile Asp Thr Asn Trp Arg Arg Gly Glu Leu Lys Ser Pro Lys
                245                 250                 255
```

-continued

Val Leu Lys Gly His Asp Asp His Val Ile Thr Cys Leu Gln Phe Cys
                260                 265                 270

Gly Asn Arg Ile Val Ser Gly Ser Asp Asp Asn Thr Leu Lys Val Trp
            275                 280                 285

Ser Ala Val Thr Gly Lys Cys Leu Arg Thr Leu Val Gly His Thr Gly
        290                 295                 300

Gly Val Trp Ser Ser Gln Met Arg Asp Asn Ile Ile Ser Gly Ser
305                 310                 315                 320

Thr Asp Arg Thr Leu Lys Val Trp Asn Ala Glu Thr Gly Glu Cys Ile
                325                 330                 335

His Thr Leu Tyr Gly His Thr Ser Thr Val Arg Cys Met His Leu His
                340                 345                 350

Glu Lys Arg Val Val Ser Gly Ser Arg Asp Ala Thr Leu Arg Val Trp
                355                 360                 365

Asp Ile Glu Thr Gly Gln Cys Leu His Val Leu Met Gly His Val Ala
            370                 375                 380

Ala Val Arg Cys Val Gln Tyr Asp Gly Arg Arg Val Val Ser Gly Ala
385                 390                 395                 400

Tyr Asp Phe Met Val Lys Val Trp Asp Pro Glu Thr Glu Thr Cys Leu
                405                 410                 415

His Thr Leu Gln Gly His Thr Asn Arg Val Tyr Ser Leu Gln Phe Asp
                420                 425                 430

Gly Ile His Val Val Ser Gly Ser Leu Asp Thr Ser Ile Arg Val Trp
            435                 440                 445

Asp Val Glu Thr Gly Asn Cys Ile His Thr Leu Thr Gly His Gln Ser
        450                 455                 460

Leu Thr Ser Gly Met Glu Leu Lys Asp Asn Ile Leu Val Ser Gly Asn
465                 470                 475                 480

Ala Asp Ser Thr Val Lys Ile Trp Asp Ile Lys Thr Gly Gln Cys Leu
                485                 490                 495

Gln Thr Leu Gln Gly Pro Asn Lys His Gln Ser Ala Val Thr Cys Leu
            500                 505                 510

Gln Phe Asn Lys Asn Phe Val Ile Thr Ser Ser Asp Asp Gly Thr Val
        515                 520                 525

Lys Leu Trp Asp Leu Lys Thr Gly Glu Phe Ile Arg Asn Leu Val Thr
                530                 535                 540

Leu Glu Ser Gly Gly Ser Gly Gly Val Val Trp Arg Ile Arg Ala Ser
545                 550                 555                 560

Asn Thr Lys Leu Val Cys Ala Val Gly Ser Arg Asn Gly Thr Glu Glu
                565                 570                 575

Thr Lys Leu Leu Val Leu Asp Phe Asp Val Asp Met Lys
            580                 585

<210> SEQ ID NO 30
<211> LENGTH: 58
<212> TYPE: DNA
<213> ORGANISM: Artificial Sequence
<220> FEATURE:
<223> OTHER INFORMATION: synthetic polynucleotide

<400> SEQUENCE: 30
ccggaacctt ctctggagag agaaactcga gtttctctct ccagagaagg ttttttg        58

<210> SEQ ID NO 31
<211> LENGTH: 58
<212> TYPE: DNA
<213> ORGANISM: Artificial Sequence
<220> FEATURE:
<223> OTHER INFORMATION: synthetic polynucleotide

<400> SEQUENCE: 31
aattcaaaaa aaccttctct ggagagagaa actcgagttt ctctctccag agaaggtt         58

<210> SEQ ID NO 32
<211> LENGTH: 58
<212> TYPE: DNA
<213> ORGANISM: Artificial Sequence
<220> FEATURE:
<223> OTHER INFORMATION: synthetic polynucleotide

<400> SEQUENCE: 32
ccggaattgc tatgtctctg ggacactcga gtgtcccaga gacatagcaa ttttttg          58

<210> SEQ ID NO 33
<211> LENGTH: 58
<212> TYPE: DNA
<213> ORGANISM: Artificial Sequence
<220> FEATURE:
<223> OTHER INFORMATION: synthetic polynucleotide

<400> SEQUENCE: 33
aattcaaaaa aattgctatg tctctgggac actcgagtgt cccagagaca tagcaatt         58

<210> SEQ ID NO 34
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 34
aaguggaauu uguggaacau c                                                 21

<210> SEQ ID NO 35
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 35
caugccgcaa uccagacaua u                                                 21

<210> SEQ ID NO 36
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 36
aauugcuaug ucucugggac a                                                 21

<210> SEQ ID NO 37
<211> LENGTH: 23
<212> TYPE: RNA
<213> ORGANISM: Artificial Sequence
<220> FEATURE:
<223> OTHER INFORMATION: synthetic polynucleotide

```
<400> SEQUENCE: 37
aacugugcca ucugcaggaa caa                                             23

<210> SEQ ID NO 38
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 38
ggucgcuuca uaaacaacau u                                               21

<210> SEQ ID NO 39
<211> LENGTH: 23
<212> TYPE: RNA
<213> ORGANISM: Artificial Sequence
<220> FEATURE:
<223> OTHER INFORMATION: synthetic polynucleotide

<400> SEQUENCE: 39
aaacuuguga agaaucguau cuu                                             23
```